US011045502B2

(12) United States Patent
Patel et al.

(10) Patent No.: US 11,045,502 B2
(45) Date of Patent: Jun. 29, 2021

(54) METHOD OF ISOLATING CELLS FOR THERAPY AND PROPHYLAXIS

(71) Applicant: THE UNIVERSITY OF QUEENSLAND, St. Lucia (AU)

(72) Inventors: Jatin Patel, Nundah (AU); Paul Kiarash Khosrotehrani, Clayfield (AU); Nicholas Maxwell Fisk, Queensland (AU)

(73) Assignee: The University of Queensland, Queensland (AU)

( * ) Notice: Subject to any disclaimer, the term of this patent is extended or adjusted under 35 U.S.C. 154(b) by 32 days.

(21) Appl. No.: 16/185,220

(22) Filed: Nov. 9, 2018

(65) Prior Publication Data
US 2019/0151373 A1 May 23, 2019

Related U.S. Application Data

(63) Continuation of application No. 14/776,288, filed as application No. PCT/AU2014/000252 on Mar. 13, 2014, now Pat. No. 10,149,864.

(30) Foreign Application Priority Data

Mar. 13, 2013 (AU) ................................ 2013900863

(51) Int. Cl.
| | | |
|---|---|---|
| *C12N 5/073* | (2010.01) | |
| *A61L 27/38* | (2006.01) | |
| *A61L 27/54* | (2006.01) | |
| *C12N 5/071* | (2010.01) | |
| *A61K 35/50* | (2015.01) | |
| *A61K 35/28* | (2015.01) | |
| *A61L 27/18* | (2006.01) | |
| *C12N 5/0775* | (2010.01) | |
| *A61K 35/44* | (2015.01) | |
| *A61L 31/00* | (2006.01) | |
| *A61L 31/16* | (2006.01) | |

(52) U.S. Cl.
CPC ............ *A61K 35/44* (2013.01); *A61K 35/28* (2013.01); *A61K 35/50* (2013.01); *A61L 27/18* (2013.01); *A61L 27/3808* (2013.01); *A61L 27/3834* (2013.01); *A61L 27/54* (2013.01); *A61L 31/005* (2013.01); *A61L 31/16* (2013.01); *C12N 5/0605* (2013.01); *C12N 5/0668* (2013.01); *C12N 5/0692* (2013.01); *A61L 2430/34* (2013.01); *C12N 2506/025* (2013.01)

(58) Field of Classification Search
None
See application file for complete search history.

(56) References Cited

U.S. PATENT DOCUMENTS

| | | | |
|---|---|---|---|
| 2008/0095746 A1 | 4/2008 | Miyajima et al. | |
| 2008/0095749 A1* | 4/2008 | Aggarwal | A61K 35/28 |
| | | | 424/93.7 |
| 2008/0206343 A1* | 8/2008 | Edinger | C12N 5/0655 |
| | | | 424/489 |
| 2009/0104164 A1 | 4/2009 | Zhang et al. | |
| 2012/0094380 A1* | 4/2012 | Tzu-Bi Shih | C12N 5/0668 |
| | | | 435/366 |
| 2012/0148546 A1 | 6/2012 | Dar-Oaknin et al. | |
| 2016/0038545 A1 | 2/2016 | Patel et al. | |

FOREIGN PATENT DOCUMENTS

WO   WO 2011/019401 A2   2/2011

OTHER PUBLICATIONS

Kim et al, Seminars in Pediatric Surgery, 1999, vol. 8, No. 3, pp. 119-123. (Year: 1999).*
Si et al, Ageing Research Reviews, 2011, vol. 10, pp. 93-103. (Year: 2011).*
Traktuev et al, Circulation Research, 2008, vol. 102, pp. 77-85 (Supplemental Data included) (Year: 2008).*
Volarevic et al, Stem Cells Regenerative Medicine, 2011, vol. 29, p. 5-10. (Year: 2011).*
Bellows, Charles F., et al., "Influence of BMI on Level of Circulating Progenitor Cells," Obesity Research, vol. 19, No. 8, Aug. 2011.
Daquinag, Alexes C., "An Isoform of Decorin Is a Resistin Receptor on the Surface of Adipose Progenitor Cells," Cell Stem Cell 9, 74-86, Jul. 8, 2011.
In 't Anker et al., "Isolation of Mesenchymal Stem Cells of Fetal or Maternal Origin from Human Placenta," Stem Cells, 2004, 22:1338-1345.
Tran, Tu Cam et al., "Identification of Human Placenta-Derived Mesenchymal Stem Cells Involved in Re-Endothelialization," J. Cell. Physiol., 226: 224-235, 2010.

(Continued)

*Primary Examiner* — Allison M Fox
(74) *Attorney, Agent, or Firm* — Nixon & Vanderhye, PC

(57) ABSTRACT

Disclosed are methods for isolating endothelial progenitor cells (EPC). More particularly, the present invention discloses methods for isolating endothelial progenitor cells that exhibit self-renewal and differentiation capacity. The isolated cellular population of the present invention is useful in a wide range of clinical and research setting including inter alia, the in vitro or in vivo generation of endothelial cells and the therapeutic or prophylactic treatment of a range of conditions via the administration of these cells. Also facilitated is the isolation of endothelial progenitor cells for research purposes such as in vitro based screening systems for testing the therapeutic impact and/or toxicity of potential treatment or culture regimes to which these cells may be exposed to. The present invention also discloses methods for isolating mesenchymal stem cells, in particular mesenchymal stem cells of fetal and/or maternal origin. These cells are also useful in a range of in vitro and in vivo therapeutic, prophylactic and research applications.

5 Claims, 19 Drawing Sheets

(56) References Cited

OTHER PUBLICATIONS

Wagner, Wolfgang et al., "Comparative Characteristics of Mesenchymal Stem Cells from Human Bone Marrow, Adipose Tissue, and Umbilical Cord Blood," Experimental Hematology, 33 (2005) 1402-1416.
Medina et al., "Molecular analysis of endothelial progenitor cell (EPC) subtypes reveals two distinct cell populations with different identities," BMC Medical Genomics 3:18 (2010).
Patel et al., "Prospective surface marker-based isolation and expansion of fetal endothelial colony-forming cells from human term placenta," Stem Cells Trans. Med. 2:839-847 (2013).
International Preliminary Report on Patentability and Written Opinion of the International Searching Authority dated Sep. 14, 2015, issued in corresponding International Application No. PCT/AU2014/000252.
Marchal et al., "Purification and Long-Term Expansion of Multipotent Endothelial-Like Cells with Potential Cardiovascular Regeneration," Stem Cells and Development 21(4):562-574, XP-002764138 (2012).
Oshima-Sudo et al., "Optimized method for culturing outgrowth endothelial progenitor cells," Inflammation and Regeneration 31(2):219-227, XP-002764139 (2011).
Solder et al., "Isolation and characterization of CD133 + CD34 + VEGFR-2 + CD45—fetal endothelial cells from human term placenta," Microvascular Research 84(1):65-73, XP-002764137 (2012).
Asai et al., "Topical application of ex vivo expanded endothelial progenitor cells promotes vascularisation and wound healing in diabetic mice," Int Wound J 10:527-533 (2013).
Atesok et al., "Endothelial Progenitor Cells Promote Fracture Healing in a Segmental Bone Defect Model," J Orthop Res 28:1007-1014 (2010).
Chang et al., "Application of peripheral-blood-derived endothelial progenitor cell for treating ischemia-reperfusion injury and infarction: a preclinical study in rat models," J Cardiothor Surg 8:33, 10 pages (2013).
Cheng et al., "Transplantation of bone marrow-derived endothelial progenitor cells attenuates myocardial interstitial fibrosis and cardiac dysfunction in streptozotocin-induced diabetic rats," Int J Mol Med 30:870-876 (2012).
Edelberg et al., "Young Adult Bone Marrow-Derived Endothelial Precursor Cells Restore Aging-Impaired Cardiac Angiogenic Function," Circ Res 90:e89-e93 (2002).
Fan et al., "Endothelial progenitor cell transplantation improves long-term outcome in mice," Ann Neurol 67(4):488-497 (2010).
Kamei et al., "Contribution of Bone Marrow-Derived Endothelial Progenitor Cells to Neovascularization and Astrogliosis Following Spinal Cord Injury," J Neurosci Res 90:2281-2292 (2012).
Kamei et al., "Endothelial Progenitor Cells Promote Astrogliosis following Spinal Cord Injury through Jagged1-Dependent Notch Signaling," J Neurotrauma 29:1758-1769 (2012).
Kang et al., "Endothelial Progenitor Cell Cotransplantation Enhances Islet Engraftment by Rapid Revascularization," Diabetes 61:866-876 (2012).
Nakamura et al., "Significance and Therapeutic Potential of Endothelial Progenitor Cell Transplantation in a Cirrhotic Liver Rat Model," Gastroenterology 133:91-107 (2007).
Nasser et al., "Fetal microchimerism in skin wound healing," Chimerism 3:45-47 (2012).
Putman et al., "Umbilical Cord Blood-Derived Aldehyde Dehydrogenase-Expressing Progenitor Cells Promote Recovery from Acute Ischemic Injury," Stem Cells 30:2248-2260 (2012).
Ratliff et al., "Delivery of EPC embedded in HA-hydrogels for treatment of acute kidney injury," Biomatter 3(1):e23284, 35-41 (2013).
Raval and Losordo, "Cell Therapy of Peripheral Arterial Disease," Circ Res 112:1288-1302 (2013).
Schwarz et al., "Vascular Incorporation of Endothelial Colony-Forming Cells Is Essential for Functional Recovery of Murine Ischemic Tissue Following Cell Therapy," Arterioscler Thromb Vasc Biol 32:e13-e21 (2012).
Lee et al., "In vitro evaluation of a poly(lactide-co-glycolide)-collagen composite scaffold for bone regeneration," Biomaterials 27:3466-3472 (2006).
Reagan et al., "Distinct phenotypes and regenerative potentials of early endothelial progenitor cells and outgrowth endothelial progenitor cells derived from umbilical cord blood," J Tissue Eng Regen Med 5:620-628 (2011).
"Cartilage," Encyclopedia Britannica. Encyclopedia Britannica Online. Encyclopedia Britannica Inc. 2017. Web Jul. 30, 2017 <https://www.britannica.com/science/cartilage.>.
Ingram et al., "Identification of a novel hierarchy of endothelial progenitor cells using human peripheral and umbilical cord blood," Blood 104:2752-2760 (2004).
Mayo Clinic "Heart Disease," Web Jul. 30, 2017 <http://mayoclinic.org/diseases-conditions/heart-failure/basics/causes/con-20029801?p=1>.
Urbich et al., "Endothelial Progenitor Cells: Characterization and Role in Vascular Biology," Circ Res 95:343-353 (2004).

* cited by examiner

FIGURE 6
A
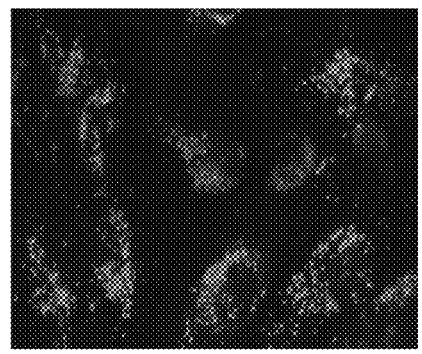
Acetylated-LDL uptake
B
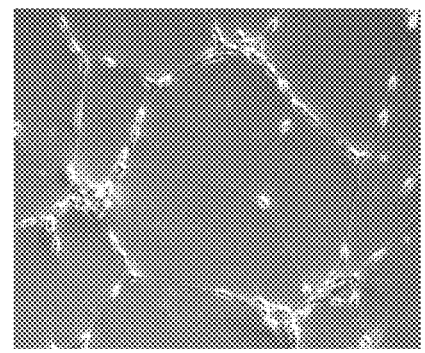
MATRIGEL Assay

FIGURE 9

|            | Fetal Bone marrow | Term Placenta | fMSC |
|------------|-------------------|---------------|------|
| CD90       | Y                 | Y             | Y    |
| CD44       | Y                 | Y             | Y    |
| CD105      | Y                 | Y             | Y    |
| CD29       | Y                 | Y             | Y    |
| CD73       | Y                 | Y             | Y    |
| CD45       | N                 | N             | N    |
| CD31       | N                 | N             | N    |
| CD34       | N                 | N             | N    |
| CD11B      | N                 | N             | N    |
| CD73+CD105 | Y                 | Y             | Y    |
| CD44+CD29  | Y                 | Y             | Y    |

FIGURE 10
A
fMSC - Osteo
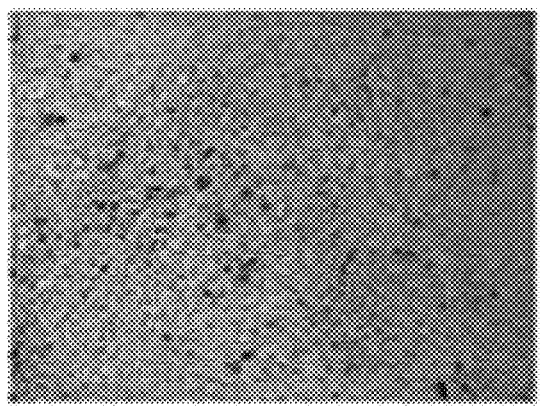
B
fBM-MSC - Osteo
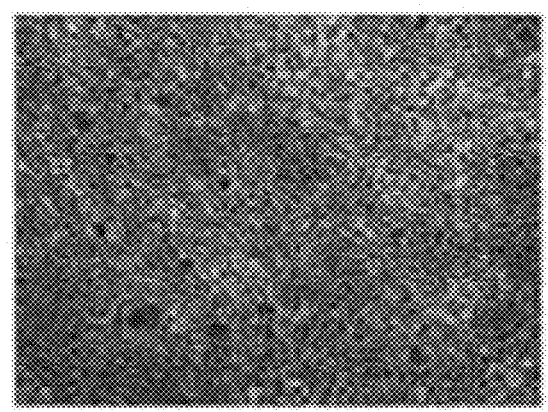
C
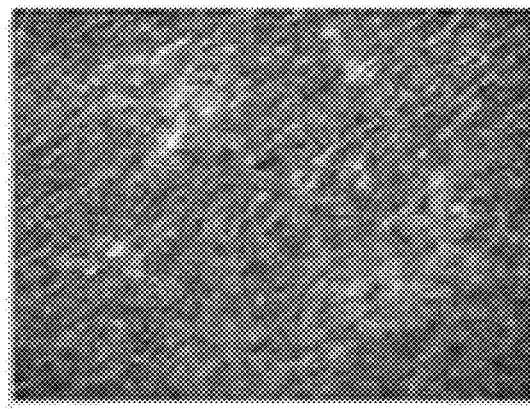
fMSC - Adipo
D
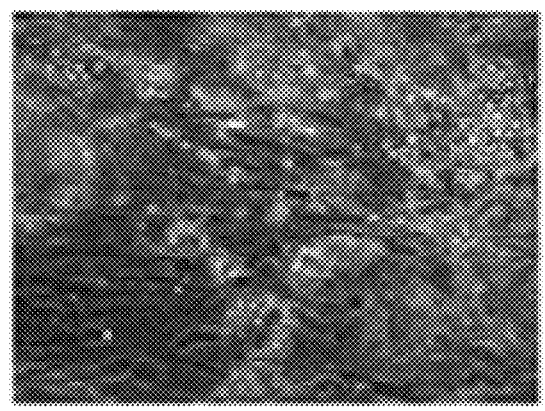
fBM-MSC - Adipo

FIGURE 15
A
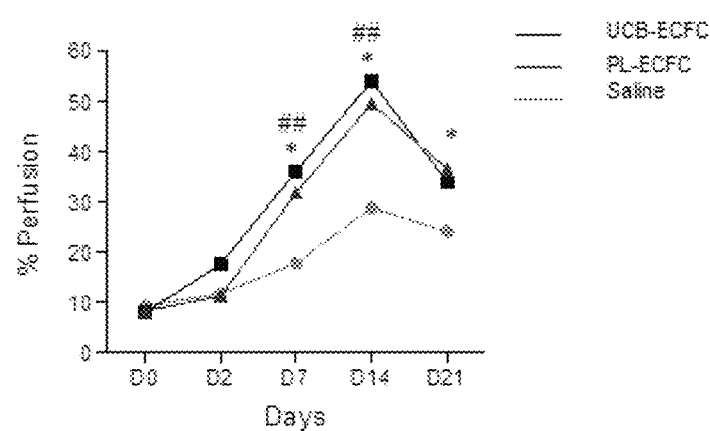
B
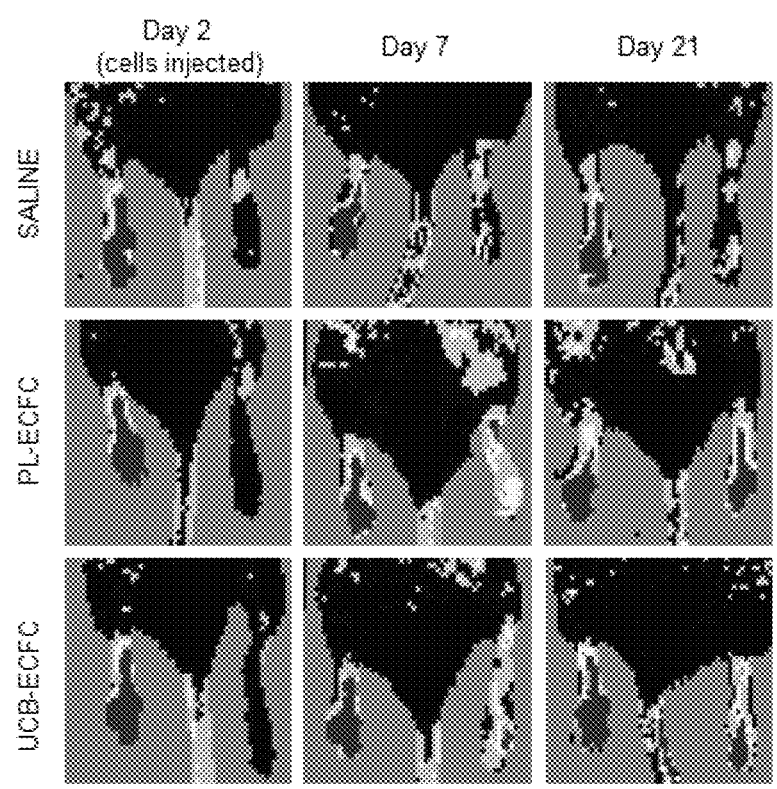

METHOD OF ISOLATING CELLS FOR THERAPY AND PROPHYLAXIS

CROSS REFERENCE TO RELATED APPLICATIONS

This application is a divisional of U.S. patent application Ser. No. 14/776,288, § 371 date of Sep. 14, 2015, now allowed, which is a U.S. National Phase of International Application No. PCT/AU2014/000252, filed Mar. 13, 2014, which claims priority to Australian Patent Application No. 2013900863, filed Mar. 13, 2013, each of which is incorporated herein by reference.

FIELD OF THE INVENTION

The present invention relates to a method of isolating endothelial progenitor cells (EPC). More particularly, the method of the present invention is directed to a method of isolating endothelial progenitor cells that exhibit self-renewal and differentiation capacity. The isolated cellular population of the present invention is useful in a wide range of clinical and research setting including inter alia, the in vitro or in vivo generation of endothelial cells and the therapeutic or prophylactic treatment of a range of conditions via the administration of these cells. Also facilitated is the isolation of endothelial progenitor cells for research purposes such as in vitro based screening systems for testing the therapeutic impact and/or toxicity of potential treatment or culture regimes to which these cells may be exposed to. In a related aspect, the method of the present invention also enables the isolation of mesenchymal stem cells, in particular mesenchymal stem cells of fetal and/or maternal origin. These cells are also useful in a range of in vitro and in vivo therapeutic, prophylactic and research applications. The design of a protocol, which in a single run can enable the efficient isolation of multiple distinct cellular populations, is unprecedented.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge in Australia.

The vascular system is essential for embryonic development and adult life (see, Flamme, I., et al.; Patan, S.). Once in place, endothelial cells have to maintain blood vessels for life. The natural turnover of endothelial cells is not homogenous throughout the vasculature but concentrated in areas of shear stress (see, Schwartz, S. M. & Benditt, E. P.; Xu, Q,). Based on animal data, endothelial cells in areas resistant to atherosclerosis have a lifespan of 12 months, whereas cells at lesion-prone sites live only for weeks, and even less as animals age. Endothelial cells thus undergo replication many times in some areas of the arterial wall (see, Xu, Q.). This turnover is increased by atherosclerosis and its risk factors, such as stress and age, resulting in endothelial senescence (see, Minamino, T. & Komuro, I.).

As the endothelial layer is at continuous risk of defects, repair mechanisms are permanently active via endothelial progenitors. These cells may be resident endothelial progenitor cells already in the vessel intima, which divide to produce additional cells. Indeed, highly proliferative endothelial cells can be identified within blood vessels. Vessel-derived resident endothelial cells such as human umbilical vein endothelial cells (HUVECs) and human aortic endothelial cells (HAECs) can be passaged in vitro for >40 population doublings—a fact that stands in contrast to the widely held belief that these are terminally-differentiated, mature endothelial cells. Alternatively, endothelial progenitor cells can come from distant sources. A mathematical model estimated that without distant endothelial progenitor cell homing, at least 4.6% (SD 1.0%) of defects in the endothelium could not be repaired by age 65 years (Op den Buijs, J., et al.). This shows however that resident cells undertake the vast majority of vascular repair. This resident endothelial self-renewal capacity depends on age: in murine models 15% of aortic endothelial cells undergo cell division at birth compared to only 0.6% at 6 months (see, Schwartz, S. M. & Benditt, E. P.). The relative contribution of distant endothelial progenitor cells to the vascular endothelium is thus small, but becomes increasingly apparent with advancing age (Op den Buijs, J., et al.). This sheds light on the need for endothelial progenitor cell therapy to maintain adult vascular homeostasis.

The identification of endothelial progenitor cells stimulated numerous clinical trials using different cell types to promote vascular repair, largely on myocardial infarction and critical limb ischemia. The most frequent sources utilized were early outgrowth endothelial progenitor cells from the peripheral circulation and bone marrow mononuclear cells (MNC). Significant improvement was observed after treatment of critical limb ischemia such as reduced limb loss, increased pain-free walking distance and healing of ischemic leg ulcers (see, Kawamoto, A., et al.; Tateishi-Yuyama, E., et al.). The benefits of endothelial progenitor cell therapy in myocardial infarction effects were modest, with improvement of left ventricular ejection fraction (LVEF) by 2-8% (see, Assmus, B., et al.; Stamm, C., et al.) associated with a reduction in the infarction size. However, no study reported any impact of endothelial progenitor cell therapy on major cardiovascular outcomes such as death, re-infarction or stroke (see, Kumar, A. H. & Caplice, N. M.).

A major limitation in these early clinical studies relate to how endothelial progenitor cells were defined. Flow cytometry with CD34, VEGFR2 (KDR/FLK-1) and/or CD133 is conventionally used to identify the number of circulating endothelial progenitor cells, in addition to more classical endothelial markers such as vascular endothelial (VE)-cadherin or CD31. However, no combination of markers has produced a reliable or discriminatory marker set. A recent controlled trial compared the efficacy of sorted or unsorted bone-marrow cells in patients who had recently suffered a myocardial infarction and found no differences in outcomes as both groups improved left ventricle ejection fraction in similar modest proportions (3%) (see, Tendera, M., et al.). An alternate approach to isolate endothelial progenitor cells is employing partially differentiated endothelial progenitor cells after short term culture on fibronectin, resulting in spindle shaped cells able to digest acetylated low density lipoprotein and stain for several specific lectins appearing within 3 days. Both methods however result in considerable contamination by hematopoietic cells. Asahara et al. reported that the CD34-enriched population was almost exclusively (97%) hematopoietic as they expressed CD45. CD34, VEGFR2 and CD133, significantly enrich for hematopoietic stem cells and are not specific for endothelial progenitor cells (see, Case, J., et al.). Of interest, monocytes ($CD34^+CD14^+$) when used in clinical trials have been implicated in the restenosis of revascularized coronary arteries and contribute to atherosclerotic plaques in vessels (see, Kumar, A. H. & Caplice, N. M.; Bartunek, J., et al.). Thus contaminating cells may negate the benefit of pure endothelial progenitor cell therapy.

Another major issue identified in previous trials was the difficulty in achieving adequate cell numbers for therapy. Most regimens used a single injection, whereas continuous delivery would be expected to be advantageous. Circulating endothelial cells isolated by FACS or magnetic sorting (hematopoietic contaminated) have been estimated at 0 to 10 cells/mL blood (see, Woywodt, A., et al.). However, the majority of these peripherally derived cells has limited expansion capacity (17 fold) and the only cells with high proliferative potential (1000 fold) are bone marrow-derived (see, Lin, Y., et al.). Accordingly, these cells are not currently a reliable source for therapies.

In a related aspect, it has also been determined that the isolation method of the present invention, in addition to enabling the isolation of endothelial progenitor cells, enables the isolation of mesenchymal stem cells, in particular fetal mesenchymal stem cells which are not contaminated with maternal mesenchymal stem cells. In fact, two populations of mesenchymal stem cells can be obtained, one that comprises only fetal mesenchymal stem cells and another that upon culturing results in maternal mesenchymal stem cells. Specifically, in the context of a single isolation protocol, multiple distinct and rare precursor cell populations are able to be effectively isolated by virtue of their separation into distinct fractions during the isolation protocol. The development of this protocol therefore provides, for the first time, a reliable and routine means of isolating multiple distinct precursor cell populations.

There is a need therefore to identify an accessible, reliable and abundant source of endothelial progenitor cells if progenitor cell-based vascular therapy is to become a reality. In work leading up to the present invention, an isolation method has been developed which can efficiently and reliably isolate a more pure endothelial progenitor cell population, than has been available to date, which population does not contain the degree of cellular contamination that has characterized prior art isolation methods. This finding thereby provides, for the first time, means to routinely and reliably isolate a pure endothelial cell population for use either in vitro or in vivo. In a further aspect, it has also been determined that the placenta in fact provides a rich source of endothelial cells and that the specific application of this method to the placenta enables isolation of endothelial progenitor cells of both a level of purity and abundance that has not been previously achievable. Accordingly, the application of the isolation method of the present invention on placental tissue, in particular, provides an abundant source of endothelial progenitor cells that exhibit both self-renewal and differentiation capacity. This finding has therefore now enabled the realistic development of endothelial progenitor cell based therapies.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

One aspect of the present invention is directed to a method of isolating mammalian endothelial progenitor cells said method comprising the steps of:
(i) isolating a mammalian cellular population;
(ii) enriching for a subpopulation of the cells of step (i), which subpopulation expresses a $CD45^-$ phenotypic profile;
(iii) enriching for a subpopulation of the $CD45^-$ cells derived from step (ii) which express a $CD34^+$ phenotypic profile; and
(iv) isolating the subpopulation of $CD34^+$ cells derived from step (iii) which express a $CD31^{lo/-}$ phenotypic profile, to thereby isolate the endothelial progenitor cells.

In another aspect there is provided a method of isolating mammalian endothelial progenitor cells said method comprising the sequential steps of:
(i) isolating a mammalian cellular population;
(ii) enriching for a subpopulation of the cells of step (i), which subpopulation expresses a $CD45^-$ phenotypic profile;
(iii) enriching for a subpopulation of the $CD45^-$ cells derived from step (ii) which express a $CD34^+$ phenotypic profile; and
(iv) isolating the subpopulation of $CD34^+$ cells derived from step (iii) which express a $CD31^{lo/-}$ phenotypic profile, to thereby isolate the endothelial progenitor cells.

In a related aspect of the present invention is directed to a method of isolating mammalian mesenchymal stem cells said method comprising the steps of:
(i) isolating a mammalian cellular population;
(ii) enriching for a subpopulation of the cells of step (i), which subpopulation expresses a $CD45^-$ phenotypic profile; and
  (a) enriching for a subpopulation of the $CD45^-$ cells derived from step (ii) which express a $CD34^+$ phenotypic profile and isolating the subpopulation of said $CD34^+$ cells which express a $CD31^-$ phenotypic profile and/or
  (b) isolating the subpopulation of $CD45^-$ cells derived from step (ii) which express a $CD34^-$ phenotypic profile, to thereby isolate the mesenchymal stem cells.

In still another aspect there is provided a method of isolating mammalian mesenchymal stem cells said method comprising the sequential steps of:
(i) isolating a mammalian cellular population;
(ii) enriching for a subpopulation of the cells of step (i), which subpopulation expresses a $CD45^-$ phenotypic profile; and
  (a) enriching for a subpopulation of the $CD45^-$ cells derived from step (ii) which express a $CD34^+$ phenotypic profile and isolating the subpopulation of said $CD34^+$ cells which express a $CD31^-$ phenotypic profile; and/or (b) isolating the subpopulation of CD45⁻ cells derived from step (ii) which express a CD34⁻ phenotypic profile, to thereby isolate the mesenchymal stem cells.

In yet another aspect there is provided a method of isolating mammalian endothelial progenitor cells said method comprising the steps of:
(i) isolating a mammalian cellular population;
(ii) enriching for a subpopulation of the cells of step (i), which subpopulation expresses a CD45⁻ phenotypic profile;
(iii) enriching for a subpopulation of the CD45⁻ cells derived from step (ii) which express a CD34⁺ phenotypic profile; and
(iv) isolating the subpopulation of CD34⁺ cells derived from step (iii) which express a CD31$^{lo/-}$ phenotypic profile, to thereby isolate the endothelial progenitor cells, wherein said endothelial progenitor cells are capable of differentiating to a vascular endothelial cell.

In still another aspect there is provided a method of isolating monopotent or multipotent mammalian endothelial progenitor cells said method comprising the steps of:
(i) isolating a mammalian cellular population;
(ii) enriching for a subpopulation of the cells of step (i), which subpopulation expresses a CD45⁻ phenotypic profile;
(iii) enriching for a subpopulation of the CD45⁻ cells derived from step (ii) which express a CD34⁺ phenotypic profile; and
(iv) isolating the subpopulation of CD34⁺ cells derived from step (iii) which express a CD31$^{lo/-}$ phenotypic profile, to thereby isolate the monopotent or multipotent endothelial progenitor cells.

In yet still another aspect there is provided a method of isolating mammalian endothelial progenitor cells said method comprising the steps of:
(i) isolating a mammalian placenta-derived cellular population;
(ii) enriching for a subpopulation of the cells of step (i), which subpopulation expresses a CD45⁻ phenotypic profile;
(iii) enriching for a subpopulation of the CD45⁻ cells derived from step (ii) which express a CD34⁺ phenotypic profile; and
(iv) isolating the subpopulation of CD34⁺ cells derived from step (iii) which express a CD31$^{lo/-}$ phenotypic profile, to thereby isolate the endothelial progenitor cells.

In still yet another aspect, the present invention is directed to a method of isolating mammalian mesenchymal stem cells said method comprising the steps of:
(i) isolating a mammalian placenta-derived cellular population;
(ii) enriching for a subpopulation of the cells of step (i), which subpopulation expresses a CD45⁻ phenotypic profile; and
  (a) enriching for a subpopulation of the CD45⁻ cells derived from step (ii) which express a CD34⁺ phenotypic profile and isolating the subpopulation of said CD34⁺ cells which express a CD31⁻ phenotypic profile; and/or
  (b) isolating the subpopulation of CD45⁻ cells derived from step (ii) which express a CD34⁻ phenotypic profile, to thereby isolate the mesenchymal stem cells.

In another aspect there is provided a method of isolating mammalian endothelial progenitor cells said method comprising the steps of:
(i) isolating mammalian placenta cotyledon cellular material;
(ii) enriching for a subpopulation of the cells of step (i), which subpopulation expresses a CD45⁻ phenotypic profile;
(iii) enriching for a subpopulation of the CD45⁻ cells derived from step (ii) which express a CD34⁺ phenotypic profile; and
(iv) isolating the subpopulation of CD34⁺ cells derived from step (iii) which express a CD31$^{lo/-}$ phenotypic profile, to thereby isolate the endothelial progenitor cells.

In still another aspect there is provided a method of isolating mammalian mesenchymal stem cells said method comprising the steps of:
(i) isolating mammalian placenta cotyledon cellular material;
(ii) enriching for a subpopulation of the cells of step (i), which subpopulation expresses a CD45⁻ phenotypic profile; and
  (a) enriching for a subpopulation of the CD45⁻ cells derived from step (ii) which express a CD34⁺ phenotypic profile and isolating the subpopulation of said CD34⁺ cells which express a CD31⁻ phenotypic profile; and/or
  (b) isolating the subpopulation of CD45⁻ cells derived from step (ii) which express a CD34⁻ phenotypic profile, to thereby isolate the mesenchymal stem cells.

In a further aspect there is therefore provided a method of isolating mammalian endothelial progenitor cells said method comprising the sequential steps of:
(i) isolating a mammalian cellular population;
(ii) enriching by negative selection for a subpopulation of the cells of step (i) which express a CD45⁻ phenotypic profile;
(iii) enriching by positive selection for a subpopulation of the CD45⁻ cells derived from step (ii) which express a CD34⁺ phenotypic profile; and
(iv) isolating by positive selection the subpopulation of CD34⁺ cells derived from step (iii) which express a CD31$^{lo/-}$ phenotypic profile, to thereby isolate the endothelial progenitor cells.

In further aspect the present invention is directed to a method of isolating mammalian mesenchymal stem cells said method comprising the steps of:
(i) isolating a mammalian cellular population;
(ii) enriching by negative selection for a subpopulation of the cells of step (i), which subpopulation expresses a CD45⁻ phenotypic profile; and
  (a) enriching by positive selection for a subpopulation of the CD45⁻ cells derived from step (ii) which express a CD34⁺ phenotypic profile and isolating by positive selection the subpopulation of said CD34⁺ which express a CD31⁻ phenotypic profile; and/or
  (b) isolating the subpopulation of CD45⁻ cells derived from step (ii) which express a CD34⁻ phenotypic profile, to thereby isolate the mesenchymal stem cells.

In one embodiment, said CD31⁻ population is a fetal CD31⁻ population and said mesenchymal stem cells are fetal mesenchymal stem cells.

In another embodiment, said CD45⁻/CD34⁻ mesenchymal stem cells are maternal stem cells.

Another further aspect of the present invention is directed to a method of therapeutically and/or prophylactically treating a condition in a mammal, said method comprising administering to said mammal an effective number of endothelial progenitor cells or partially or fully differentiated EPC-derived cells, which endothelial progenitor cells have been isolated according to the method of the present invention.

In related aspect of the present invention there is provided a method of facilitating the generation of a mammalian MSC-derived cell, said method comprising contacting the mesenchymal stem cells isolated in accordance with the method of the present invention with a stimulus to direct the differentiation of said mesenchymal stem cells to a mesenchymal phenotype.

Yet another further aspect of the present invention is directed to the use of a population of endothelial progenitor cells or EPC-derived cells, which cells have been isolated in accordance with the method of the present invention, in the manufacture of a medicament for the treatment of a condition in a mammal.

In another aspect, the present invention is directed to a method of therapeutically and/or prophylactically treating a condition in a mammal, said method comprising administering to said mammal an effective number of mesenchymal stem cells or partially or fully differentiated MSC-derived cells, which mesenchymal stem cells have been isolated according to the method of the present invention.

Still another aspect of the present invention is directed to an isolated population of endothelial progenitor cells or EPC-derived cells which endothelial progenitor cells have been isolated in accordance with the method of the present invention.

Another aspect of the present invention is directed to the use of a population of mesenchymal stem cells or MSC-derived cells, which cells have been isolated in accordance with the method of the present invention, in the manufacture of a medicament for the treatment of a condition in a mammal.

Yet another aspect of the present invention is directed to an isolated population of mesenchymal stem cells or MSC-derived cells, which mesenchymal stem cells have been isolated in accordance with the method of the present invention.

In still another aspect of the present invention, there is provided a method of assessing the effect of a treatment or culture regime on the phenotypic or functional state of mesenchymal stem cells or MSC-derived cells said method comprising subjecting said mesenchymal stem cells or MSC-derived cells, which mesenchymal stem cells have been isolated in accordance with the method hereinbefore defined, to said treatment regime and screening for an altered functional or phenotypic state.

The present inventors have also determined that EPC isolated in accordance with the methods broadly described above and elsewhere herein are qualitatively different than EPC derived from umbilical cord blood (UCB) with reference to the genes they express. Specifically, they have determined that the subject EPC express one or more marker genes at a level that is at least 10% different (e.g., higher or lower) than the expression level of a corresponding marker gene in an EPC derived from UCB.

Accordingly, another aspect of the present invention provides an isolated endothelial progenitor cell that expresses at least one marker gene (e.g., at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or 33 marker genes) selected from the group consisting of MFGE8, MATN2, ELN, IGFBP2, SERPINH1, P4HA3, FN1, PKNOX2, FOXC1, NFIX, SMAD6, PRRX2, LRRC17, CTSK, PLA2G4A, DIRAS3, PDLIM3, ABCA8, CFB, PTK7, PTGFRN, SETBP1, LOC652900, SLC22A17, TANC2, SEZ6L2, ARRDC4, PODXL, MEOX2, MMP4, FAM107A, LOC647543 and SCAMPS at a level that is at least 10% different (e.g., higher or lower) than the expression level of a corresponding marker gene in an endothelial progenitor cell derived from umbilical cord blood (UCB).

In a related aspect, the present invention provides an isolated endothelial progenitor cell that expresses at least one marker gene (e.g., at least 1, 2, 3, 4, 5, 6, 7, 8, 9, 10, 11, 12, 13, 14, 15, 16, 17, 18, 19, 20, 21, 22, 23, 24, 25, 26 or 27 marker genes) selected from the group consisting of MFGE8, MATN2, ELN, IGFBP2, SERPINH1, P4HA3, FN1, PKNOX2, FOXC1, NFIX, SMAD6, PRRX2, LRRC17, CTSK, PLA2G4A, DIRAS3, PDLIM3, ABCA8, CFB, PTK7, PTGFRN, SETBP1, LOC652900, SLC22A17, TANC2, SEZ6L2 and ARRDC4 at a level that is at least 10% (and at least 11% to at least 1000% and all integer percentages in between) higher than the expression level of a corresponding marker gene in an endothelial progenitor cell derived from umbilical cord blood (UCB).

In another related aspect, the present invention provides an isolated endothelial progenitor cell that expresses at least one marker gene (e.g., at least 1, 2, 3, 4, 5 or 6 marker genes) selected from the group consisting of PODXL, MEOX2, MMP4, FAM107A, LOC647543 and SCAMPS at a level that is less than 90% (and less than 89% to less than 0.001% and all integer and decimal percentages in between) of the expression level of a corresponding marker gene in an endothelial progenitor cell derived from umbilical cord blood (UCB).

Suitably, the isolated endothelial progenitor cell is derived from placenta.

In some embodiments, the isolated endothelial progenitor cell expresses a $CD31^{lo}$ phenotypic profile. Suitably, in these embodiments, the isolated endothelial progenitor cell additionally expresses at least one phenotypic profile (at least 1, 2 or 3 phenotypic profiles) selected from the group consisting of a $CD45^-$ phenotypic profile and a $CD34^+$ phenotypic profile.

In some embodiments, the isolated endothelial progenitor cell further expresses at least one phenotypic profile (at least 1, 2, 3, 5, 6 or 7 phenotypic profiles) selected from the group consisting of a $CD105^+$ phenotypic profile, a $CD144^+$ phenotypic profile, a $CD146^+$ phenotypic profile, a $VEGFR2^+$ phenotypic profile, a $HLA-ABC^+$ phenotypic profile, a $CD73^-$ phenotypic profile and a $HLA-DR^-$ phenotypic profile.

Yet another aspect of the present invention provides an isolated population of cells enriched for endothelial progenitor cells as broadly described above and elsewhere herein.

Still another aspect of the present invention provides a biocompatible implant comprising an endothelial progenitor cell or cell population as broadly described above and elsewhere herein.

In some embodiments, the implant is selected from vascular prostheses, vascular grafts, fixtures for connecting prosthetic organs to vascular circulation, stents including vascular and nonvascular stents (e.g., gastrointestinal, pulmonary or biliary stents), covered stents, artificial heart valves, artificial hearts, cardiac prosthesis (e.g., an artificial heart valve), a biological heart valve prosthesis (e.g., derived from animals such as pigs—xenografts can be coated with EPC to render them more biocompatible and less thrombic), venous valves, abdominal aortic aneurysm grafts, vascular filters (e.g., vena cava filter), catheters, guide wires, balloons, devices to protect against pulmonary embolism (e.g., embolic coils, embolic materials for vascular embolization, etc.), orthopedic implants (e.g., bone or joint prostheses), vascular sutures, scaffolds, smooth or porous implants, intraluminal devices, vascular prosthetic filters, pacemakers, pacemaker lead, electrodes, defibrillators, subcutaneous and/or intramuscular implants, vascular occlude, ventricular shunt, vascular sheath, drug delivery devices and ports, septal closure devices, sutures, neurological stimulators, implantable wireless sensors (e.g., blood glucose and blood pressure monitors), artificial filtration systems or other artificial organs, insulin pumps, artificial oxygenators and the like. In illustrative examples of this type, the implant further comprises at least one bioactive agent. Suitably, the implant is biodegradable or non-biodegradable.

The endothelial progenitor cells of the present invention are useful for repairing or regenerating a tissue in a subject. Accordingly, in another aspect, the present invention provides a method of repairing or regenerating a tissue in a subject, the method comprising contacting the tissue with an endothelial progenitor cell, cell population or implant as broadly described above and elsewhere herein, thereby repairing or regenerating the tissue.

In a related aspect, the present invention provides a method for enhancing angiogenesis in a subject, the method comprising contacting a tissue of the subject (which suitably requires angiogenesis) with an endothelial progenitor cell, cell population or implant as broadly described above and elsewhere herein, thereby enhancing angiogenesis.

In another related aspect, the present invention provides a method for enhancing vasculogenesis in a subject, the method comprising contacting a tissue of the subject (which suitably requires vasculogenesis) with an endothelial progenitor cell, cell population or implant as broadly described above and elsewhere herein, thereby enhancing vasculogenesis.

Suitably, the tissue is a muscle tissue, skeletal muscle tissue, cardiac tissue, neural tissue, liver tissue, pancreatic tissue, bone tissue, cartilage, renal tissue, eye tissue, skin tissue or a tissue characterized by excess cell death.

In some embodiments, the subject has or is at risk of developing a disease selected from the group consisting of myocardial infarction, congestive heart failure, peripheral vascular obstructive disease, ischemia, limb ischemia, stroke, transient ischemia, reperfusion injury, and wounds, inclusive of skin wounds, diabetic foot or ulcers, gangrene and diabetic wounds.

In a related aspect, the present invention provides a method for ameliorating ischemia related tissue damage in a subject, the method comprising: (a) administering to the subject an endothelial progenitor cell, cell population or implant as broadly described above and elsewhere herein; and (b) enhancing angiogenesis or vasculogenesis in a tissue of the subject, thereby ameliorating ischemia related tissue damage in the subject.

In some embodiments, the ischemia related tissue damage is associated with heart failure, myocardial infarction, other ischemic heart diseases, limb ischemia, stroke, transient ischemia, or reperfusion injury.

In another related aspect, the present invention provides a method for ameliorating heart failure in a subject, the method comprising: (a) administering to a cardiac tissue of the subject an endothelial progenitor cell, cell population or implant as broadly described above and elsewhere herein; and (b) enhancing angiogenesis or vasculogenesis in the cardiac tissue of the subject, thereby ameliorating heart failure in the subject.

Yet another aspect of the present invention provides a method for enhancing wound healing in a tissue of a subject, the method comprising: (a) administering to the tissue an endothelial progenitor cell, cell population or implant as broadly described above and elsewhere herein; and (b) increasing angiogenesis or vasculogenesis thereby increasing wound healing.

In the treatment methods of the present invention broadly described above and elsewhere herein, the endothelial cell or cell population is suitably isolated or derived from a donor subject (e.g., a donor subject that is histocompatible with the treated subject).

In a further aspect, the present invention provides a pharmaceutical composition comprising an endothelial progenitor cell or cell population as broadly described above and elsewhere herein, and a pharmaceutically acceptable carrier.

Yet another aspect of the present invention provides a kit for repairing or regenerating a tissue in a subject, the kit comprising a therapeutically effective amount of an endothelial progenitor cell or cell population as broadly described above and elsewhere herein, and instructions for repairing or regenerating the tissue.

In some embodiments, the subject has or is at risk of developing a disease selected from the group consisting of myocardial infarction, congestive heart failure, peripheral vascular obstructive disease, ischemia, limb ischemia, stroke, transient ischemia, reperfusion injury, and wounds, inclusive of skin wounds, diabetic foot or ulcers, gangrene and diabetic wounds and the kit suitably includes instructions for the treatment of the disease.

BRIEF DESCRIPTION OF THE DRAWINGS

FIG. 6: Endothelial cells were obtained upon culture of placental EPC as indicated by our isolation method. Cells were incubated with acetylated low density lipoprotein (Ac-LDL) labeled with DiI (red) that they were able to uptake as expected from an endothelial population. (B) HPP-ECFC cultured on MATRIGEL were able to form tubes, again demonstrating functional endothelial properties.

FIG. 9: Cell surface characteristics of MSC populations isolated from the placental $CD45^-CD34^+CD31^-$ (fMSC) fraction as compared to other known sources of maternal or fetal MSC. At passage 4, the fMSC fraction was analyzed by flow cytometry for characteristic cell surface molecules found on MSC. The results were compared to a fetal source of MSC (fetal bone marrow) and a source of adult MSC (whole placenta). Indeed whole placenta culture always results in pure populations of maternal MSC. Both fractions generated fibroblastic type cells that had the required cell surface expression as defined by the international society of cell therapy to be qualified as MSC.

FIG. 10: Differentiation characteristics of fMSC fractions. MSC obtained from the fMSC fraction as well as the $CD45^-CD34^-$ fractions were subjected to osteo-(A, B) or adipogenic (C, D) conditions. All fractions tested showed their capacity to form osteoblasts and adipocytes as depicted by alizarin (upper panels) or oil Red O staining respectively (lower panels). $CD45^-CD34^-$ is not depicted. Compared to fetal bone marrow derived MSC, all fractions revealed reduced osteogenic but similar or increased adipogenic differentiation capacity.

(FIG. 13A): By extrapolating obtained HPP colonies per sample, 1,230 HPP colonies are obtained from an entire placenta (about 500-600 g), compared with 45 HPP from whole UBC (about 60 mL) ($p<0.001$, PL-ECFC vs. UCB-ECFC, HPP; $p<0.001$, PL-ECFC vs. UCB-ECFC, total colonies). (FIG. 13B-G): In culture an HPP-ECFC colony was identical in morphology between PL-ECFC and UCB-ECFC and displayed the same in vitro colony hierarchy when an HPP colony was replated (scale bars=100 μm). They possessed almost identical cell proliferations over time (passages 2-10) and population doubling time. Using an enzyme-linked immunosorbent assay system, integrin expression was measured, and again no difference was observed between PL-ECFC and UCB-ECFC. Bars indicate SD, and the Wilcoxon-Mann-Whitney test was used for statistical analysis.

FIG. 15: Assessment of PL-ECFC function using the murine hind limb ischemia model. (A): Following femoral artery ligation in one limb and injection of either saline (n=16), PL-ECFC (n=8), or UCB-ECFC (n=10), leg perfusion was measured by Doppler at specific time points (represented by median values). By day 7 there was a significant improvement in perfusion in ischemic legs treated with PL-ECFC (1.85-fold increase vs. saline), $p<0.02$) or UCB-ECFC (2.1-fold increase vs. saline, $p<0.007$) compared with saline controls. This same pattern was observed at day 14 (1.75-fold increase vs. saline), $p<0.02$) and day 21 (1.5-fold increase in PL-ECFC vs. saline, $p<0.05$; 1.4-fold increase in UCB-ECFC vs. saline, $p<0.03$, respectively). Green, saline; red, PL-ECFC; black, UCB-ECFC. (B): Representative Doppler images displaying the level of perfusion at day 2 and day 21 of the three experimental groups. Red, blood flow in limb, blue, no blood flow in limb.

DETAILED DESCRIPTION OF THE INVENTION

Figure 1:
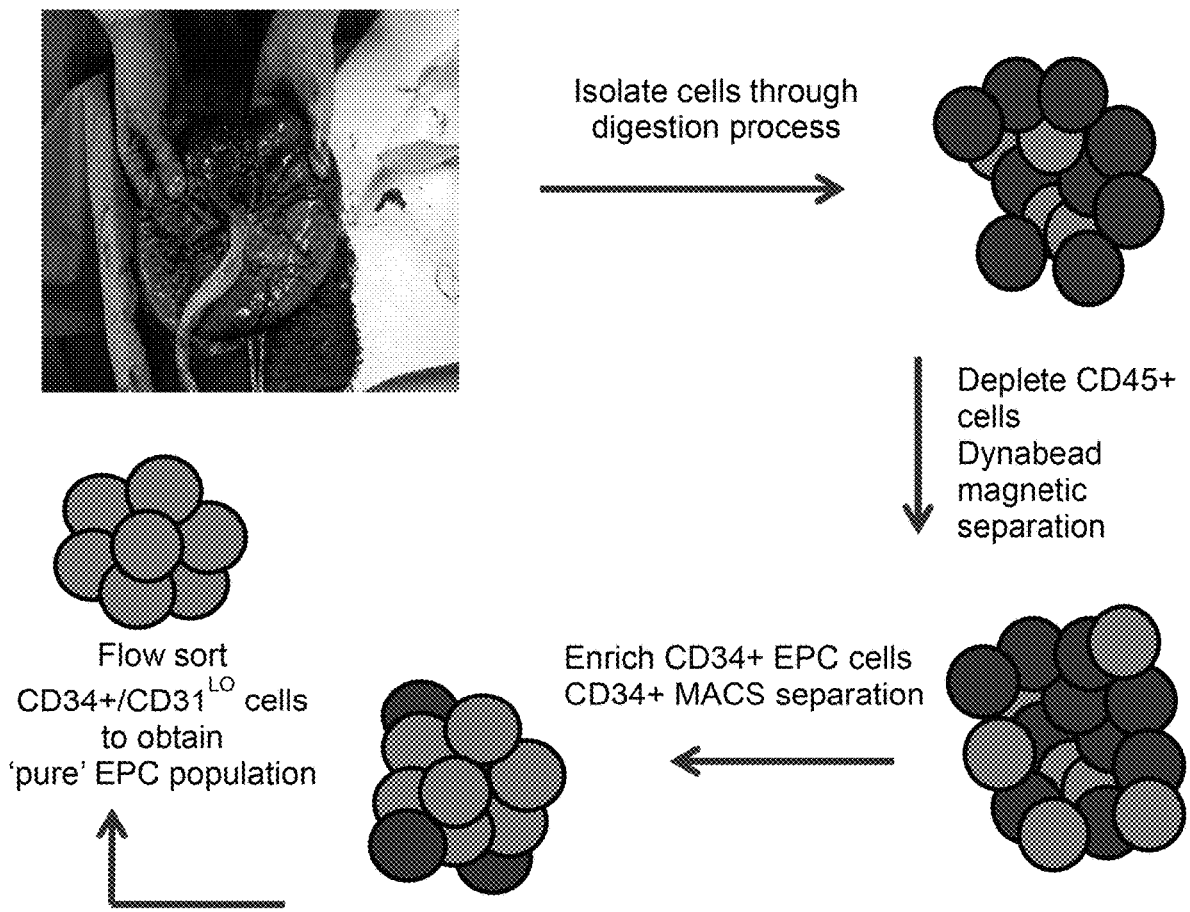
FIG. 1: is a schematic depiction of the placental digestion and sorting strategy.

The present invention is predicated, in part, on the development of a novel method of routinely and reliably isolating higher quantities of a significantly more pure population of endothelial progenitor cells than has previously been enabled. This method is based on a unique multistep combination of positive and negative selection steps directed to targeting a specific sequence of cell surface markers. Accordingly, where it was not previously possible to efficiently and reliably isolate the relatively rare population of endothelial progenitor cells at the level of purity which is desirable for effective therapeutic and prophylactic treatment regimes, this finding has now overcome this significant obstacle. Still further, in the context of this protocol, a population of pure fetal mesenchymal stem cells can also be isolated separately to a population of mesenchymal stem cells that comprise the maternal mesenchymal stem cell population. Accordingly, there has been developed a single multi-step protocol that conveniently and reliably isolates and yields multiple precursor cell populations that are present in the starting biological material. To this end, it has also been determined that the placenta in fact provides a rich source of endothelial progenitor cells which exhibit self-renewal capacity and has therefore enabled the routine and efficient detection and isolation of abundant numbers of endothelial progenitor cells, thereby enabling in vitro and in vivo applications which have not previously been clinically feasible due to limited cell availability. Also facilitated are means of routinely assessing the effectiveness and/or toxicity of potential treatment or culture regimes to which endothelial or mesenchymal derived cells may be exposed.

Accordingly one aspect of the present invention is directed to a method of isolating mammalian endothelial progenitor cells said method comprising the steps of:
(i) isolating a mammalian cellular population;
(ii) enriching for a subpopulation of the cells of step (i), which subpopulation expresses a $CD45^-$ phenotypic profile;
(iii) enriching for a subpopulation of the $CD45^-$ cells derived from step (ii) which express a $CD34^+$ phenotypic profile; and
(iv) isolating the subpopulation of $CD34^+$ cells derived from step (iii) which express a $CD31^{lo/-}$ phenotypic profile, to thereby isolate the endothelial progenitor cells.

More particularly there is provided a method of isolating mammalian endothelial progenitor cells said method comprising the sequential steps of:
(i) isolating a mammalian cellular population;
(ii) enriching for a subpopulation of the cells of step (i), which subpopulation expresses a $CD45^-$ phenotypic profile;
(iii) enriching for a subpopulation of the $CD45^-$ cells derived from step (ii) which express a $CD34^+$ phenotypic profile; and
(iv) isolating the subpopulation of $CD34^+$ cells derived from step (iii) which express a $CD31^{lo/-}$ phenotypic profile, to thereby isolate the endothelial progenitor cells.

In a related aspect of the present invention is directed to a method of isolating mammalian mesenchymal stem cells said method comprising the steps of:
(i) isolating a mammalian cellular population;
(ii) enriching for a subpopulation of the cells of step (i), which subpopulation expresses a $CD45^-$ phenotypic profile; and
  (a) enriching for a subpopulation of the $CD45^-$ cells derived from step (ii) which express a $CD34^+$ phenotypic profile and isolating the subpopulation of said $CD34^+$ cells which express a $CD31^-$ phenotypic profile; and/or
  (b) isolating the subpopulation of $CD45^-$ cells derived from step (ii) which express a $CD34^-$ phenotypic profile, to thereby isolate the mesenchymal stem cells.

More particularly, there is provided a method of isolating mammalian mesenchymal stem cells said method comprising the sequential steps of:
(i) isolating a mammalian cellular population;
(ii) enriching for a subpopulation of the cells of step (i), which subpopulation expresses a $CD45^-$ phenotypic profile; and
  (a) enriching for a subpopulation of the $CD45^-$ cells derived from step (ii) which express a $CD34^+$ phenotypic profile and isolating the subpopulation of said $CD34^+$ cells which express a $CD31^-$ phenotypic profile; and/or
  (b) isolating the subpopulation of $CD45^-$ cells derived from step (ii) which express a $CD34^-$ phenotypic profile, to thereby isolate the mesenchymal stem cells.

Endothelial progenitor cells are a population of rare cells that circulate in the blood with the ability to differentiate into endothelial cells. Without limiting the present invention to any one theory or mode of action, endothelial progenitor cells were first believed to be angioblasts, these being stem cells that form blood vessels during embryogenesis. While embryonic angioblasts have been known to exist for many years, adult endothelial progenitor cells were first believed to be characterized in the 1990s after Asahara and colleagues published that a purified population of $CD34^+$ cells isolated from the blood of adult mice could purportedly differentiate into endothelial cells in vitro. Accordingly, reference to "endothelial progenitor cell" should be understood as a reference to any cell that exhibits the potentiality to develop to a cell exhibiting one or more of the functional or structural characteristics that are exhibited by an endothelial cell. Still without limiting the present invention in any way, reference to "endothelial cell" should be understood as a reference to the squamous epithelial cells that line the blood vessels, lymphatics or other serous cavities such as fluid-filled cavities. The phrase "endothelial cells" should also be understood as a reference to cells that exhibit one or more of the morphology, phenotype and/or functional activity of endothelial cells and is also a reference to mutants or variants thereof. Said endothelial cells may be at any differentiative stage of development subsequent to the endothelial progenitor cell stage. "Variants" include, but are not limited to, cells exhibiting some but not all of the morphological or phenotypic features or functional activities of endothelial cells. "Mutants" include, but are not limited to, endothelial cells which are genetically modified, such as endothelial cells derived from endothelial progenitor cells which are genetically modified subsequently to isolation by the method of the present invention but prior to undergoing directed differentiation along the endothelial cell lineage. Preferably, the subject endothelial cells are blood vessel endothelial cells (i.e., endothelial cells which form blood vessels) or are an immature form of endothelial cells which would proliferate and differentiate to form a blood vessel but which are nevertheless more mature than an endothelial progenitor cell.

According to this embodiment, there is provided a method of isolating mammalian endothelial progenitor cells said method comprising the steps of:
(i) isolating a mammalian cellular population;
(ii) enriching for a subpopulation of the cells of step (i), which subpopulation expresses a $CD45^-$ phenotypic profile;
(iii) enriching for a subpopulation of the $CD45^-$ cells derived from step (ii) which express a $CD34^+$ phenotypic profile; and
(iv) isolating the subpopulation of $CD34^+$ cells derived from step (iii) which express a $CD31^{lo/-}$ phenotypic profile, to thereby isolate the endothelial progenitor cells.

and wherein said endothelial progenitor cell is capable of differentiating to a vascular endothelial cell.

In one embodiment steps (ii) to (iv) are performed sequentially. Without limiting the present invention to any one theory or mode of action, in addition to the bone marrow stroma comprising hematopoietic stem cells it is also known to comprise other non-hematopoietic stem cells, termed mesenchymal stem cells, the latter cell type being mesodermally derived and also being capable of both self renewal and differentiation, inter alia, to bone, cartilage, muscle, tendon, ligament, stroma, marrow, fat, neurons and astrocytes. Mesenchymal stem cells are also similar to hematopoietic stem cells in that they are very rare, existing at an estimated frequency of 1 in 100,000 bone marrow cells. Mature, fully differentiated mesenchymal-derived cells are the result of a step-wise maturation process termed mesogenesis. In addition to their localization to the bone marrow, mesenchymal stem cells are also found in a variety of other tissues including, but not limited to fat, bone, dental pulp and uterus.

Still without limiting the present invention in any way, the mature cell types to which mesenchymal stem cells give rise can contribute to the formation of the connective tissue of the organ in issue. "Connective tissue" is a generalized term for mesodermally derived tissue which may be more or less specialized. For example, cartilage and bone are forms of specialized connective tissue, as is blood. Other forms of less specialized connective tissue includes the tissues which are rich in extracellular matrix and surround other more highly ordered tissues and organs. Connective tissue therefore comprises many cell types that exhibit a variety of functions.

Reference to a "mesenchymal stem cell" should therefore be understood as a reference to any cell which exhibits the potentiality to develop to a cell exhibiting one or more of the functional or structural characteristics which are exhibited by a mesenchymal or mesenchymal-derived cell but not a non-mesenchymal-derived cell such as an endodermal or mesodermal derived cell type. Mesenchymal stem cells are also alternatively known as "stromal stem cells", "fetal stem cells", "adult stem cells", "adipose derived stem cells", "lipoaspirate derived stem cells" and "post natal stem cells". To this end, reference to "mesenchymal-derived cell" should be understood as a reference to cell types that are more differentiated than a pluripotent mesenchymal cell and which have arisen from a mesenchymal stem cell. These cells will correspond to cells of the tissues to which mesenchymal cells are known to give rise and which have been detailed hereinbefore. For example, the subject mesenchymal-derived cell may be a cell which is irreversibly committed to differentiating along a particular cell lineage, such as a myocytic precursor cell or adipocytic precursor cell, or it may correspond to a partially or terminally differentiated form of a specific cellular subtype of one of these lineages. Accordingly, mesenchymal stem cells exhibit the ability to differentiate to a cell type of one or more of the mesenchymal lineages under appropriate conditions The mesenchymal stem cells that are identified in accordance with the method of the invention are defined as cells that are not terminally differentiated. Accordingly, although it is a preferred embodiment that the subject cells are capable of differentiating along any mesenchymal lineage or even some non-mesenchymal lineages such as neuroectodermal cells (i.e., pluripotent mesenchymal cells), they may also correspond to cells that are capable of differentiating along just some of the mesenchymal lineages.

By "progenitor cell" and "stem cell" is meant that the cell is not fully differentiated but requires further differentiation to achieve maturation. Such cells also typically exhibit a higher degree of proliferation capacity than is exhibited by a fully differentiated cell. This proliferation capacity is also referred to as self-renewal capacity. Progenitor cells are capable of forming bigger colonies (i.e. they undergo a high level of proliferation) while more differentiated cells form smaller colonies. Fully differentiated cells do not form colonies. Progenitor cells and stem cells are also sometimes referred to as "precursor" cells "multipotent" cells, or "pluripotent" cells (although the latter term is generally reserved for cells which exhibit extensive potentiality). In this regard, stem cells are also generally regarded as a cell which exhibits wider potentiality than progenitor cells, as is exemplified herein where a mesenchymal stem cell has the potential to differentiate into a wider range of somatic cell types than an endothelial progenitor cell. It should be understood that the endothelial progenitor cell of the present invention may be monopotent or multipotent. A monopotent cell is one that can differentiate along only the endothelial cell lineage. A multipotent progenitor cell is one that can differentiate along either an endothelial or non-endothelial cell lineage. Without limiting the present invention in any way, it is generally thought that endothelial progenitor cells are monopotent. However, it would be appreciated by the person of skill in the art that under appropriate artificial conditions, particularly in vitro, a progenitor cell can sometimes be forced to differentiate along a lineage that would not occur naturally in vivo. It should therefore be understood that even if the isolated endothelial progenitor cells of the present invention are found to be capable of directed differentiation along non-endothelial cell lineages, provided that they have been isolated in accordance with the present invention and exhibit endothelial potential, they fall within the scope of the "endothelial progenitor cells" herein defined.

It should be understood that the endothelial progenitor cell populations and mesenchymal stem cell populations of the present invention may exhibit some variation in differentiative status within a single phenotypic profile. That is, within a single phenotypic profile, although the cells comprising that profile may substantially exhibit similar phenotypic and/or functional characteristics, there may nevertheless exhibit some differences. This may be apparent, for example, in terms of differences in the transcriptome profile or cell surface marker expression (other than the markers defined herein) of the cells that comprise the phenotypic profile in issue. For example, the $CD45^-/CD34^+/CD31^{lo/-}$, the $CD45^-/CD34^+/CD31^-$ or the $CD45^-/CD34^-$ cells may not represent a highly specific and discrete stage, but may be characterized by a number of discrete cellular subpopulations which reflect a transition or phase if one were to compare cells which have differentiated into this stage versus cells which are on the cusp of maturing out of this stage. This is typically characteristic, for example, by the onset of a sequential series of changes to gene expression, two or more of which are required to occur before the characteristic phenotypic profile defined herein is changed. Accordingly, the existence of cellular subpopulations within a single phenotypic profile of the present invention is encompassed.

According to this embodiment there is provided a method of isolating monopotent or multipotent mammalian endothelial progenitor cells said method comprising the steps of:

(i) isolating a mammalian cellular population;
(ii) enriching for a subpopulation of the cells of step (i), which subpopulation expresses a CD45$^-$ phenotypic profile;
(iii) enriching for a subpopulation of the CD45$^-$ cells derived from step (ii) which express a CD34$^+$ phenotypic profile; and
(iv) isolating the subpopulation of CD34$^+$ cells derived from step (iii) which express a CD31$^{lo/-}$ phenotypic profile, to thereby isolate the endothelial progenitor cells.

In another embodiment, said endothelial progenitor cell is capable of differentiating to a vascular endothelial cell.

The subject endothelial progenitor cell and mesenchymal stem cells may be derived from any suitable mammalian tissue source including embryonic, cord, fetal, placental or post-natal tissue, such as adult tissue. To this end, reference to "mammal" includes humans, primates, livestock animals (e.g. horses, cattle, sheep, pigs, donkeys), laboratory test animals (e.g. mice, rats, guinea pigs), companion animals (e.g. dogs, cats) and captive wild animal (e.g. kangaroos, deer, foxes). Preferably, said mammal is a human.

Reference to a "mammalian cellular population" should be understood as a reference to a population of cells derived from a mammalian tissue source as defined above. The isolated cellular population (or "tissue sample" or "biological sample"—these terms being used interchangeably) should be understood as a reference to any sample of biological material which comprises cells and is derived from a mammal such as, but not limited to, cellular material (e.g. bone marrow or adipose aspirates), biological fluids (e.g. blood), tissue biopsy specimens (e.g. uterine biopsies), surgical specimens (e.g. hysterectomy tissue) or placental tissue.

The biological sample that is tested according to the method of the present invention may be tested directly or may require some form of treatment prior to testing. For example, a biopsy or surgical sample may require homogenization or other form of cellular dispersion prior to testing. Further, to the extent that the biological sample is not in liquid form, it may require the addition of a reagent, such as a buffer, to mobilize the sample and create a cell suspension. Alternatively, it may require some other form of pretreatment such a heparinization, where the sample is a whole blood sample, in order to prevent clotting.

The subject tissue (which includes reference to "cells") may be a single cell suspension or a cell aggregate which has been freshly isolated from an individual (such as an individual who may be the subject of treatment) or it may have been sourced from a non-fresh source, such as from a culture (for example, where cell numbers were expanded and/or the cells were cultured so as to render them receptive to differentiative signals) or a frozen stock of cells which had been isolated at some earlier time point either from an individual or from another source. It should also be understood that the subject cells, prior to undergoing analysis in accordance with the present method, may have undergone some other form of treatment or manipulation, such as but not limited to enrichment or purification, modification of cell cycle status or the formation of a cell line. Accordingly, the subject cell may be a primary cell or a secondary cell. A primary cell is one that has been isolated from an individual. A secondary cell is one which, following its isolation, has undergone some form of in vitro manipulation prior to the application of the method of the invention.

In one particular embodiment, said mammalian cellular population is derived from umbilical cord blood or placenta, in particular post-parturition placenta.

According to this embodiment there is provided a method of isolating mammalian endothelial progenitor cells said method comprising the steps of:
(i) isolating a mammalian placenta-derived cellular population;
(ii) enriching for a subpopulation of the cells of step (i), which subpopulation expresses a CD45$^-$ phenotypic profile;
(iii) enriching for a subpopulation of the CD45$^-$ cells derived from step (ii) which express a CD34$^+$ phenotypic profile; and
(iv) isolating the subpopulation of CD34$^+$ cells derived from step (iii) which express a CD31$^{lo/-}$ phenotypic profile, to thereby isolate the endothelial progenitor cells.

In a related embodiment, the present invention is directed to a method of isolating mammalian mesenchymal stem cells said method comprising the steps of:
(i) isolating a mammalian placenta-derived cellular population;
(ii) enriching for a subpopulation of the cells of step (i), which subpopulation expresses a CD45$^-$ phenotypic profile; and
  (a) enriching for a subpopulation of the said CD45$^-$ cells derived from step (ii) which express a CD34$^+$ phenotypic profile and isolating the subpopulation of said CD34$^+$ cells which express a CD31$^-$ phenotypic profile and/or
  (b) isolating the subpopulation of CD45$^-$ cells derived from step (ii) which express a CD34$^-$ phenotypic profile, to thereby isolate the mesenchymal stem cells.

In another embodiment, step (ii)-(iv) are performed sequentially.

Reference to "placenta-derived" cellular material should be understood as a reference to some or all of the heterogeneous population of cells that make up the placenta. Without limiting the present invention to any one theory or mode of action, in humans the placenta averages 22 cm in length and 2-2.5 cm in thickness, with the center being the thickest and the edges being the thinnest. It typically weighs approximately 500 grams. It exhibits a dark reddish-blue or crimson color and connects to the fetus by an umbilical cord of approximately 55-60 cm in length. The umbilical cord contains two umbilical arteries and one umbilical vein. The umbilical cord inserts into the chorionic plate. Vessels branch out over the surface of the placenta and further divide to form a network covered by a thin layer of cells. This results in the formation of villous tree structures. On the maternal side, these villous tree structures are grouped into lobules called cotyledons. In humans, the placenta usually has a disc shape, but size varies vastly between different mammalian species.

The placenta begins to develop upon implantation of the blastocyst into the maternal endometrium. The outer layer of the blastocyst becomes the trophoblast, which forms the outer layer of the placenta. This outer layer is divided into two further layers: the underlying cytotrophoblast layer and the overlying syncytiotrophoblast layer. The syncytiotrophoblast is a multinucleated continuous cell layer that covers the surface of the placenta. It forms as a result of differentiation and fusion of the underlying cytotrophoblast cells, a process that continues throughout placental development. The syncytiotrophoblast (otherwise known as syncytium) thereby contributes to the barrier function of the placenta. The placenta grows throughout pregnancy. Development of the maternal blood supply to the placenta is complete by the end of the first trimester of pregnancy (approximately 12-13 weeks).

In one embodiment, said placenta-derived cellular population is the cellular population of the cotyledons. Without limiting the present invention in any way, in one embodiment a post-parturition placenta is used, such as an intact placenta obtained following a caesarean section. The decidual component is dissected away in order to isolate the placental cotyledons. These cotyledons are then digested in a cocktail of enzymes, such as collagenase, dispase and DNAse, and thereafter filtered in order to obtain the starting population of cells for treatment in accordance with the method of the present invention.

It should be understood that in accordance with this particular embodiment of the present invention, one may use placenta at any stage of development. Although post-parturition placenta is most conveniently obtained, placentas from earlier stages of pregnancy may also be used, such as where a miscarriage or other termination of pregnancy occurs. As is discussed in more detail hereafter, placenta in particular and umbilical cord blood provide a good source of endothelial progenitor cells and mesenchymal stem cells which can now be efficiently isolated in accordance with the method developed by the present inventors. Accordingly, this provides the possibility of women routinely isolating and storing either placental/umbilical cord tissue or blood (for example) for future endothelial progenitor cell harvesting or else freshly harvesting and then freezing endothelial progenitor cells for future use. This therefore provides the possibility of either autologous endothelial progenitor cell treatment or, for individuals related to the donor, more closely MHC-matched endothelial progenitor cells than might otherwise be accessible. In both of these cases the donor endothelial progenitor cells are defined as being histocompatible with respect to the recipient of those cells.

In one embodiment there is therefore provided a method of isolating mammalian endothelial progenitor cells said method comprising the steps of:
  (i) isolating mammalian placenta cotyledon cellular material;
  (ii) enriching for a subpopulation of the cells of step (i), which subpopulation expresses a $CD45^-$ phenotypic profile;
  (iii) enriching for a subpopulation of the $CD45^-$ cells derived from step (ii) which express a $CD34^+$ phenotypic profile; and
  (iv) isolating the subpopulation of $CD34^+$ cells derived from step (iii) which express a $CD31^{lo/-}$ phenotypic profile, to thereby isolate the endothelial progenitor cells.

In still another embodiment there is provided a method of isolating mammalian mesenchymal stem cells said method comprising the steps of:
  (i) isolating mammalian placenta cotyledon cellular material;
  (ii) enriching for a subpopulation of the cells of step (i), which subpopulation expresses a $CD45^-$ phenotypic profile; and
    (a) enriching for a subpopulation of the $CD45^-$ cells derived from step (ii) which express a $CD34^+$ phenotypic profile and isolating the subpopulation of said $CD34^+$ cells) which express a $CD31^-$ phenotypic profile; and/or
    (b) isolating the subpopulation of $CD45^-$ cells derived from step (ii) which express a $CD34^-$ phenotypic profile, to thereby isolate the mesenchymal stem cells.

In another embodiment, said mammal is a human.

It would be appreciated that the phenotypic characterization of the cellular population of the present invention is a significant development since the identification of a reliable marker profile in the context of the endothelial cell hierarchy has been elusive. Without limiting the present invention to any one theory or mode of action:
  (i) CD45 is a protein tyrosine phosphatase, receptor type, C also known as PTPRC, which is an enzyme that, in humans, is encoded by the PTPRC gene. CD45 was originally called leukocyte common antigen or T200. The protein encoded by this gene is a member of the protein tyrosine phosphatase (PTP) family. PTP are known to be signaling molecules that regulate a variety of cellular processes including cell growth, differentiation, mitotic cycle, and oncogenic transformation. The CD45 family consists of multiple members that are all products of a single complex gene. This gene contains 34 exons and three exons of the primary transcripts are alternatively spliced to generate up to eight different mature mRNAs and after translation eight different protein products. These three exons generate the RA, RB and RC isoforms. Various isoforms of CD45 exist: CD45RA, CD45RB, CD45RC, CD45RAB, CD45RAC, CD45RBC, CD45R0, CD45R (ABC).
  (ii) CD34 is a cell surface glycoprotein and functions as a cell-cell adhesion factor. It may also mediate the attachment of stem cells to bone marrow extracellular matrix or directly to stromal cells. CD34 is also the name for the human gene that encodes the protein. The CD34 protein is a member of a family of single-pass transmembrane sialomucin proteins that show expression on early hematopoietic and vascular-associated tissue. Cells expressing CD34 are normally found in the umbilical cord and bone marrow as hematopoietic cells, a subset of mesenchymal stem cells, endothelial progenitor cells, endothelial cells of blood vessels but not lymphatics (except pleural lymphatics), mast cells, a sub-population dendritic cells (which are factor XIIIa negative) in the interstitium and around the adnexa of dermis of skin, as well as cells in soft tissue tumors like DFSP, GIST, SFT, HPC.
  (iii) Platelet endothelial cell adhesion molecule (PECAM-1) also known as CD31 is a protein that in humans is encoded by the PECAM1 gene found on chromosome 17. PECAM-1 is found on the surface of platelets, monocytes, neutrophils, and some types of T-cells, and makes up a large portion of endothelial cell intercellular junctions. The encoded protein is a member of the immunoglobulin superfamily and is likely involved in leukocyte migration, angiogenesis, and integrin activation. CD31 is normally found on endothelial cells, platelets, macrophages and Küpffer cells, granulocytes, T/NK cells, lymphocytes, megakaryocytes, osteoclasts and neutrophils.

In the context of the present invention, it should be understood that reference to "CD45", "CD34" and "CD31" is a reference to all forms of these molecules and to functional fragments, mutants or variants thereof. It should also be understood to include reference to any isoform that may arise from alternative splicing of CD45, CD34 and CD31 mRNA or isomeric or polymorphic forms of these molecules.

Reference to "phenotypic profile" should be understood as a reference to the presence or absence of the transcription of the genes encoding the subject markers and/or the cell surface expression of the expression product translated therefrom. It should be appreciated that although most cells falling within the scope of the claimed endothelial progenitor cell populations will be characterized by the presence or absence of the subject marker as a cell surface anchored expression product, some cells falling within the defined populations may initially exhibit changes only at the transcriptome level, such as when the transcription of a given marker has been upregulated but may not yet have resulted in a cell surface anchored expression product. In general, cells which progress to a new differentiative stage will transiently exhibit gene expression changes which are not yet evident in the context of changes to levels of an expression product. However, these cells nevertheless fall within the scope of the claimed cellular populations, although they will not be isolatable by the method defined herein until such time as cell surface marker expression occurs.

It should also be appreciated that although the endothelial progenitor and mesenchymal stem cell populations of the present invention are characterized by the defined phenotypic profiles, these cells will express a range of other intracellular and/or cell surface markers which are not relevant in terms of phenotypically characterizing and isolating the cellular population of interest. Still further, to the extent that a given endothelial progenitor cell population of the present invention comprises a range of subpopulations, these subpopulations may exhibit variations in the expression of intracellular or cell surface markers other than those of the profiles defined herein.

Although the CD45 and CD34 cell surface markers are defined by reference to the presence or absence of the marker on the cell surface, the expression of CD31 is defined by reference to the level of expression, specifically a low level of expression (herein referred to as "CD31$^{lo/-}$"). In the embodiment of the invention exemplified herein, the "CD31$^{lo/-}$" subpopulation is based on defining a FACS gate based on an isotype control. In this exemplified embodiment, only the isotype control for CD31 is used and all other antibodies are kept equal. Three populations are seen based on CD31 level of expression. The first is negative for CD31 that gives rise to the fetal mesenchymal stem cells. The second population that gives rise to the endothelial progenitor cells is where the positive gate starts. Finally there is a CD31$^+$ population that has limited proliferative capacity. It would be appreciated by the skilled person that the specific manner in which the analysis is set up and the logs that are used can vary according to the voltage of the FACS. However, these parameters can be established as a matter of routine procedure by the skilled person.

The term "lo/−" as used in relation to CD31$^{lo/-}$ is well known in the art and refers to the expression level of CD31, in that the expression level of this cell surface marker is low by comparison with the expression level of that marker in the population of cells being analyzed as a whole. The term "lo" in relation to CD31$^{lo}$ refers to a distinct cell or population of cells that expresses CD31 at a lower level than one or more other distinct cells or populations of cells. Thus, the terms CD31$^{lo/-}$ and CD31$^{lo}$ are used interchangeably herein to refer to the endothelial progenitor cells resulting from the subject isolation methods.

In specific embodiments, the level of CD31 expressed by a CD31$^{lo}$ cell or population of cells is less than 50% (and less than 49% to no less than 1% and all integer percentages in between, suitably less than 40% to no less than 1% and all integer percentages in between, suitably less than 30% to no less than 1% and all integer percentages in between, suitably less than 20% to no less than 1% and all integer percentages in between, even more suitably less than 10% to no less than 1% and all integer percentages in between) of the level of CD31 expressed by a HUVEC or HUVEC population.

The terms "+" and "−" are well known in the art and refer to the expression level of the cell marker of interest, in that the expression level of the cell marker corresponding to "+" is high or intermediate and the expression level of the cell marker corresponding to "−" is null. Cells in the top 2, 3, 4, or 5% of staining intensity are often designated "hi", with those falling in the top half of the population categorized as being "+". Those cells falling below 50% of fluorescence intensity are designated as "lo" cells and below 1% as "−" cells.

The term "high" or "hi" or "bright" is well known in the art and refers to the expression level of the cell marker of interest, in that the expression level of the cell marker is high by comparison with the expression level of that cell marker in the population of cells being analyzed as a whole.

In terms of the CD45/CD34$^-$ mesenchymal stem cell population, this population gives rise to a significant population of maternal mesenchymal stem cells. Without limiting the present invention to any one theory or mode of action, it is thought that this cellular fraction is in fact heterogeneous. However, upon in vitro culture of these cells under conditions appropriate for mesenchymal stem cells, cells other than mesenchymal cells do not grow, thereby leading to the generation of a population of predominantly mesenchymal stem cells which are of maternal origin.

The present invention also encompasses an isolated population of cells containing endothelial progenitor cells and/or mesenchymal stem cells as broadly described above and elsewhere herein. As used herein, "and/or" refers to and encompasses any and all possible combinations of one or more of the associated listed items, as well as the lack of combinations when interpreted in the alternative (or). In specific embodiments, the isolated cell population is a population in which the EPC and/or MSC are enriched over a starting cell population, i.e., that the EPC and/or MSC are present in number or as a percentage of the cells that is greater than a starting cell population or sample. Cell populations enriched for EPC are suitably produced using the methods for producing EPC and/or MSC as described herein.

In certain embodiments, the EPC in the isolated population are 10% or more of the cells in the population, including 20% or more, 30% or more, 40% or more, 50% or more, 70% or more, 80% or more, 90% or more, 97% or more, up to and include 100% of the cells in the isolated population.

In certain embodiments, the MSC in the isolated population are 10% or more of the cells in the population, including 20% or more, 30% or more, 40% or more, 50% or more, 70% or more, 80% or more, 90% or more, 97% or more, up to and include 100% of the cells in the isolated population.

The EPC of the subject invention, which are suitably derived from placenta, can be characterized by their gene expression pattern relative to the pattern of gene expression in EPC derived from umbilical cord blood (UCB). The terms "expression" or "gene expression" refer to production of RNA only or production of RNA and translation of RNA into proteins or polypeptides. Detection of either types of gene expression is encompassed by the present invention.

In particular, the EPC of the present invention differentially express the genes set out in Table 1 relative to the expression of the corresponding genes in UBC-derived EPC.

TABLE 1

| Gene name | Fold change | p value | Function |
| --- | --- | --- | --- |
| MFGE8 | 2.44 | 0.01 | VEGF-dependent neovascularization |
| MATN2 | 5.45 | 0.01 | Von Willebrand factor A domain |
| ELN | 3.92 | 0.01 | Supports vessel stability |
| PODXL | −2.02 | 0.02 | Cell adhesion |
| IGFBP2 | 17.86 | 0.01 | Mediator of cell growth and development |
| SERPINH1 | 2.43 | 0.03 | Collagen biosynthesis |
| P4HA3 | 1.73 | 0.04 | Collagen biosynthesis |
| FN1 | 2.23 | 0.04 | Fibronectin biosynthesis |
| PKNOX2 | 2.80 | 0.03 | Transcription factor |
| FOXC1 | 2.52 | 0.02 | Transcription factor |
| NFIX | 2.68 | 0.05 | Transcription factor |
| SMAD6 | 2.20 | 0.03 | Transcriptional mediator |
| MEOX2 | −2.67 | 0.04 | Mesoderm induction |
| PRRX2 | 2.96 | 0.01 | Activates fetal fibroblasts |
| LRRC17 | 5.54 | 0.03 | Bone homeostasis |
| CTSK | 5.81 | 0.01 | Bone homeostasis |
| PLA2G4A | 2.52 | 0.04 | Cytosolic enzyme |
| DIRAS3 | 1.92 | 0.03 | Tumor suppressor |
| MPP4 | −2.31 | 0.04 | Retina development |
| PDLIM3 | 2.75 | 0.01 | Muscular stability |
| ABCA8 | 4.64 | 0.00 | Drug transporter |
| CFB | 2.28 | 0.04 | Complement system |
| PTK7 | 2.51 | 0.02 | Wnt signalling pathways |
| PTGFRN | 3.13 | 0.04 | Prostaglandin pathways |
| FAM107A | −3.43 | 0.04 | Other |
| SETBP1 | 1.78 | 0.04 | Other |
| LOC647543 | −3.64 | 0.04 | Other |
| LOC652900 | 2.39 | 0.01 | Other |
| SLC22A17 | 4.05 | 0.01 | Other |
| SCAMP5 | −2.44 | 0.03 | Other |
| TANC2 | 1.79 | 0.04 | Other |
| SEZ6L2 | 3.06 | 0.00 | Other |
| ARRDC4 | 2.19 | 0.04 | Other |

Thus, the subject EPC may be characterized by expressing one or marker genes as set out in Table 1 at a level that is at least 10% different (e.g., higher or lower) than the expression level of a corresponding marker gene in an EPC derived from UCB. In specific embodiments, the EPC of the present invention express at least one marker gene (e.g., at least 1, 2, 3, 4, 5, 6, 7, 8, 9, 10, 11, 12, 13, 14, 15, 16, 17, 18, 19, 20, 21, 22, 23, 24, 25, 26 or 27 marker genes) selected from the group consisting of MFGE8, MATN2, ELN, IGFBP2, SERPINH1, P4HA3, FN1, PKNOX2, FOXC1, NFIX, SMAD6, PRRX2, LRRC17, CTSK, PLA2G4A, DIRAS3, PDLIM3, ABCA8, CFB, PTK7, PTGFRN, SETBP1, LOC652900, SLC22A17, TANC2, SEZ6L2 and ARRDC4 at a level that is at least 10% (and at least 11% to at least 1000% and all integer percentages in between) higher than the expression level of a corresponding marker gene in UCB-derived EPC. In certain embodiments, the EPC of the present invention express at least one marker gene (e.g., at least 1, 2, 3, 4, 5 or 6 marker genes) selected from the group consisting of PODXL, MEOX2, MMP4, FAM107A, LOC647543 and SCAMPS at a level that is less than 90% (and less than 89% to less than 0.001% and all integer and decimal percentages in between) of the expression level of a corresponding marker gene in UCB-derived EPC.

The method of the present invention is predicated on a multistep isolation method that effectively and efficiently achieves the isolation of endothelial progenitor cells and mesenchymal stem cells. This is achieved through a series of enrichment and isolation steps that are based on screening for the expression of the cell surface markers CD45, CD34 and CD31. As detailed hereinbefore, it has been determined that endothelial progenitor cells, which are a very rare cell, can only be effectively and efficiently isolated where CD45, CD34 and CD31 screening is performed in a specific linear sequence of steps which progressively refine the starting population of cells and enable both these rare cells to be isolated and the maternal and fetal mesenchymal stem cell populations to be isolated. As would be appreciated by the person of skill in the art, where a cell type of interest is in low numbers in a biological sample, the process of its purification becomes significantly more difficult due to the fact that these cells are easily non-specifically lost during a cell surface marker-based purification process.

In the context of the present invention, it has been determined that endothelial progenitor and mesenchymal stem cell isolation can be effectively achieved where a biological sample is initially subjected to a CD45$^-$ enrichment step. This is most conveniently achieved via a negative selection or depletion step wherein the subpopulation of cells expressing CD45 are identified and removed from the biological sample, typically using a CD45 binding molecule such as an anti-CD45 antibody. This then leaves in the original sample the CD45$^-$ subpopulation of cells that were not selected and removed by the CD45 binding molecule. In another example, this step can be achieved by gradient separation. This enriched cellular population is then further enriched for either the CD34$^+$ or the CD34$^-$ subpopulation of cells. This is conveniently performed as a positive selection step using a molecule that specifically interacts with CD34. If a cell surface separation method such as flow cytometry (e.g., FACS), microfluidic or magnetic based sorting is used, the CD34$^-$ cellular population and the CD34$^+$ cellular population can be simultaneously sorted and collected.

In terms of these two steps, which are preferably performed sequentially, reference to "enriching" should be understood as a reference to increasing the ratio of cells expressing the desired phenotype relative to the cells not expressing the desired phenotype in the starting sample. This is achieved by removing or otherwise reducing the number of cells that do not express the desired phenotype. It should be understood that reference to enrichment is not limited to an enrichment step that removes all the cells not expressing the desired phenotype from the sample. Rather, it is a reference to decreasing the concentration of these suitably undesired cells in the test sample. The decrease in concentration may therefore be of varying degrees. The method of the present invention should be understood to extend to conducting one or more repeated sequential enrichment steps in order to improve the purity of the desired subpopulation (such as by performing two or more sequential CD45$^-$ enrichment steps or two or more CD34$^+$ or CD34$^-$ enrichment steps). The decision as to whether one or more enrichment steps are required to be performed at any given stage can be made by a person skilled in the art on a case by case basis. When target endothelial progenitor cell numbers are relatively high (such as in a placenta lobe sample), a single enrichment step may be sufficient to enrich for the desired subpopulation. However, where a sample such as blood is used (with very low numbers of endothelial progenitor cells), it may be desirable to perform two or more of each enrichment step in order to maximize the purity of the desired cellular subpopulation.

Subsequently to the CD45$^-$ and CD34$^+$ enrichment steps, the subpopulation of cells derived therefrom is screened for the level of CD31 expression. Three distinct subpopulations of cells (fetal mesenchymal stem cells (fMSC), fetal endothelial progenitor cells and differentiated endothelial progenitor cells) are isolated. Where FACS analysis is used, for example, a single analysis step simultaneously classifies all cells in the sample in terms of their level of CD31 expression, thereby enabling the $CD31^-CD31^{lo/-}$ and $CD31^+$ populations to be separately identified and discretely isolated. To this end, reference to "isolation" should be understood as a reference to separating the $CD31^-$, $CD31^{lo/-}$ and $CD31^+$ cells from each other and from those cells that do not express this phenotype. To the extent that subsequently to the $CD45^-$ enrichment step, the population of $CD34^+$ cells is isolated, this reference to "isolation" should be understood to have a corresponding meaning to that of $CD31^-$ isolation. This can be achieved by any suitable method, such as FACS sorting. However, it should be understood that this reference to "isolation" is effectively a reference to achieving a highly enriched population of cells. Although it is desirable if this isolated cell population is pure, this may not be achievable since in any biological system cellular contamination may occur. Accordingly, there may still be a small proportion of contaminating cells. However, it has been determined by the present inventors that the level of contamination that may exist is so low as to be a very significant improvement on the endothelial progenitor cell populations which were obtained by the prior art methods and which contained significant numbers of contaminating cells, such as hematopoietic stem cells and mesenchymal stem cells. In context of the mesenchymal stem cell population, the contaminating maternal mesenchymal stem cells can be removed. These contaminating cells adversely impacted upon the therapeutic utility of the endothelial progenitor cell population. However, these maternal mesenchymal stem cells are now able to be discretely isolated by virtue of their $CD45^-/CD34^-$ phenotype.

According to this embodiment there is therefore provided a method of isolating mammalian endothelial progenitor cells said method comprising the sequential steps of:
(i) isolating a mammalian cellular population;
(ii) enriching by negative selection for a subpopulation of the cells of step (i) which express a $CD45^-$ phenotypic profile;
(iii) enriching by positive selection for a subpopulation of the $CD45^-$ cells derived from step (ii) which express a $CD34^+$ phenotypic profile; and
(iv) isolating by positive selection the subpopulation of $CD34^+$ cells derived from step (iii) which express a $CD31^{lo/-}$ phenotypic profile, to thereby isolate the endothelial progenitor cells.

In another embodiment the present invention is directed to a method of isolating mammalian mesenchymal stem cells said method comprising the steps of:
(i) isolating a mammalian cellular population;
(ii) enriching by negative selection for a subpopulation of the cells of step (i), which subpopulation expresses a $CD45^-$ phenotypic profile; and
  (a) enriching by positive selection for a subpopulation of the $CD45^-$ cells derived from step (ii) which express a $CD34^+$ phenotypic profile and isolating by positive selection the subpopulation of said $CD34^+$ cells which express a $CD31^-$ phenotypic profile; and/or
  (b) isolating the subpopulation of $CD45^-$ cells derived from step (ii) which express a $CD34^-$ phenotypic profile, to thereby isolate the mesenchymal stem cells.

In one embodiment, said $CD34^+CD31^-$ population is a population of fetal mesenchymal stem cells.

In another embodiment, said $CD34^-$ population comprises maternal mesenchymal stem cells.

In still another embodiment, said cellular population is a placenta-derived population.

In terms of isolating these cell populations in accordance with the method of the invention, various well-known techniques can be performed. Antibodies and other CD45, CD34 and/or CD31 specific cell surface binding molecules are particularly useful. For example, antibodies may be attached to a solid support to allow for separation. Procedures for separation may include magnetic separation, using antibody magnetic beads, affinity chromatography, "panning" with antibody attached to a solid matrix or any other convenient technique such as Laser Capture Microdissection. Other techniques providing particularly accurate separation include fluorescence activated cell sorting. In yet another example, but specifically in the context of the CD45 negative selection step, rather than physically separating the $CD45^-$ cellular subpopulation from the $CD45^+$ cellular population, one may utilize a method which labels the $CD45^+$ cells and then delivers a targeted lysis signal which lyses the labeled $CD45^+$ cells, such as a cytolytic, apoptotic or toxic signal. In another example, opsonization with an antibody followed by complement administration may achieve the same outcome.

In a related aspect, it should be understood that the cells derived in accordance with the application of the method of the present invention can be manipulated or used in any desirable manner. For example, one may elect to direct the differentiation of these cells, in vitro, in order to generate a differentiated population of somatic cells. In another example, one may seek to administer the endothelial progenitor cells in vivo such that maturation of these progenitor cells occurs in situ. In yet another example, one may seek to store the endothelial progenitor cells, such as in a frozen state in liquid nitrogen, for future use. In yet another example, one may seek to maintain these cells in culture either simply to maintain their viability and immature status or, further, to induce their self-renewal and expansion, while maintaining their endothelial progenitor cell status, so as to provide a larger cell number for use either in vitro or in vivo.

To this end, in one particular application, the endothelial progenitor cells or mesenchymal stem cells isolated by the method of the present invention are maintained in long-term culture. Such culture methods have not traditionally been successful or available but a more recently developed method, which induces endothelial colony forming cells (ECFC) has been developed to maintain viability and effect the self-renewal and/or expansion of endothelial progenitor cells in vitro (Ingram, D. A., et al., Identification of a novel hierarchy of endothelial progenitor cells using human peripheral and umbilical cord blood, *Blood* 104: 2752-2760 (2004)). This method represents a new gold standard in the field. Without limiting the present invention to any one theory or mode of action, ECFC express cell surface antigens found in primary endothelium, clonally propagate and replate into secondary and tertiary ECFC, are not hematopoietic and form tube-like structures in vitro. These cells are capable of forming blood vessels that incorporate with host vasculature. This culture method provides a reliable method of maintaining and expanding endothelial progenitor cells. In a typical example, the $CD34^+/CD31^{lo/-}/CD45^-$ cells obtained in accordance with the method of the present invention are plated onto pre-coated collagen tissue culture plates with EGM-2 supplemented with 10% fetal bovine serum. The cells are cultured over ten days which leads to the formation of high proliferative endothelial colony forming cell colonies which are the same as those obtained from cord blood (Fisk, N. M. & Atun, R., Public-private partnership in cord blood banking, BMJ 336, 642-644 (2008))

In addition to maintaining in culture or storing the cells isolated in accordance with the method of the present invention, the present invention can also be adapted to subsequently induce the differentiation of the endothelial progenitor cells (EPC) or mesenchymal stem cells (MSC) which are isolated by the method of the present invention. For example, in the context of one embodiment of the present invention, endothelial progenitor cells give rise to endothelial cells, these being the cells that line the blood vessels, lymphatics and serous cavities. In another embodiment, the mesenchymal stem cells may be differentiated to bone, fat or cartilage, either alone or mixed with specific matrices. To the extent that it is one or more of these more fully differentiated cell types which is the subject of interest, the method of the invention can be adapted, either in vitro or in vivo, to include a further step which introduces the subject endothelial progenitor cells to the specific stimuli required to effect partial or full differentiation along the lineage of interest. Alternatively, the endothelial progenitor cells may be exposed to specific stimuli that effect dedifferentiation along the lineage of interest (e.g., induced pluripotent stem cells (iPS cells)).

As described above, although this additional directed differentiation event is conveniently performed in vitro, it could also be achieved in vivo. This is discussed in more detail hereinafter. However, a specific in situ environment may conveniently provide the necessary range of signals required to direct the differentiation of the endothelial progenitor cells along a particular lineage.

Reference to "EPC-derived cells" should therefore be understood as a reference to cell types that are more differentiated or less differentiated than endothelial progenitor cells and that have arisen from the endothelial progenitor cells isolated by the method of the present invention. These cells will correspond to cells of the lineages to which endothelial progenitor cells are known to give rise, such as vasculature. It should be understood that the subject EPC-derived cell may be a more differentiated precursor cell or it may be a somatic cell. It should therefore be understood that the cells falling within the scope of this aspect of the present invention may be at any post-endothelial progenitor cells stem cell differentiative stage of development. As detailed hereinbefore, this further differentiation may occur constitutively or it may require one or more further signals. These signals may be provided either in vitro, such as in the context of small scale in vitro tissue culture or large scale bioreactor production, or in an in vivo microenvironment, such as if an endothelial progenitor cell is transplanted into an appropriate tissue microenvironment to enable its further differentiation. A corresponding definition applies in relation to "MSC-derived cells", albeit in the context of the differentiative lineages to which mesenchymal stem cells are known to give rise, as detailed earlier.

Accordingly, in a related aspect of the present invention there is provided a method of facilitating the generation of a mammalian EPC-derived cell, said method comprising contacting the endothelial progenitor cells isolated in accordance with the method of the present invention with a stimulus to direct the differentiation of said endothelial progenitor cells to an endothelial phenotype.

In another embodiment, said EPC-derived cell is a vascular, lymphatic or serous cavity squamous epithelial cell.

Accordingly, in related aspect of the present invention there is provided a method of facilitating the generation of a mammalian MSC-derived cell, said method comprising contacting the mesenchymal stem cells isolated in accordance with the method of the present invention with a stimulus to direct the differentiation of said mesenchymal stem cells to a mesenchymal phenotype.

In the context of this aspect of this invention, it should be understood that there may be produced both cellular aggregates such as tissues (for example, vasculature, bone, fat or cartilage), or cell suspensions.

It should be understood that the culture system of this aspect of the invention may result in the production of a heterogeneous population of cells. This may occur, for example, if not all the cells of the starting precursor cell population are induced to differentiate to a more mature and homogeneous phenotype. This being the case, since not all the cells of the starting population may necessarily differentiate to the EPC- or MSC-derived phenotype, and the EPC- or MSC-derived cellular output which is obtained may itself be heterogeneous, the method of the invention may require the application of a screening and selection step to identify and isolate cells exhibiting the desired phenotype. Identification methods would be well known to the person of skill in the art and include, but are not limited to:

(i) Detection of cell lineage specific structures.
  Detection of cell lineage specific structures can be performed, for example, via light microscopy, fluorescence affinity labeling, fluorescence microscopy or electron microscopy, depending on the type of structure to be identified. Light microscopy can be used to detect morphologic characteristics. Electron microscopy can be used to detect structures such as sarcomeres, X-bands, Z-bodies, intercalated discs, gap junctions or desmosomes. Fluorescence affinity labeling and fluorescence microscopy can be used to detect cell lineage specific structures by fluorescently labeling a molecule, commonly an antibody, which specifically binds to the structure in issue, and which is either directly or indirectly conjugated to a fluorophore. Automated quantitation of such structures can be performed using appropriate detection and computation systems.

(ii) Detection of cell lineage specific proteins.
  Detection of cell lineage specific proteins, such as cell surface proteins or intracellular proteins, may be conveniently effected via fluorescence affinity labeling and fluorescence microscopy, for example. Specific proteins can be detected in both whole cells and tissues. Alternatively, techniques such as Western immunoblotting or hybridization micro arrays ("protein chips") may be employed. The proteins that can be detected via this method may be any protein that is characteristic of a specific population of cells. For example, classes of precursor/progenitor cell types can be distinguished via the presence or absence of expression of one or more cell surface molecules. In this regard, this method can be utilized to identify cell types via either a positive or negative selection step based on the expression of any one or more molecules. More mature cells can usually be characterized by virtue of the expression of a range of specific cell surface or intracellular proteins which are well defined in the literature.

(iii) Detection of cell lineage specific RNA or DNA.
  This method is preferably effected using RT-PCR or real-time (qRT-PCR). Alternatively, other methods that can be used include hybridization microarray ("RNA chip") or Northern blotting or Southern blotting. RT- PCR can be used to detect specific RNAs encoding essentially any protein, such as the proteins detailed in point (ii) above, or proteins that are secreted or otherwise not conveniently detectable via the methodology detailed in point (ii).

(iv) Detection of cell lineage specific functional activity.

Although the analysis of a cell population in terms of its functioning is generally regarded as a less convenient method than the screening methods of points (i)-(iii), in some instances this may not be the case.

It should be understood that in the context of characterizing the population of cells obtained via application of this aspect of the method of the present invention, any one or more of the techniques detailed above may be utilized.

In terms of isolating or enriching an in vitro EPC- or MSC-derived population there are, again, various well-known techniques which can be performed. As detailed hereinbefore, antibodies and other cell surface binding molecules, such as lectins, are particularly useful for identifying markers associated with particular cell lineages and/or stages of differentiation. The antibodies may be attached to a solid support to allow for separation. However, other cell separation techniques include those based on differences in physical characteristics (density gradient centrifugation and counter-flow centrifugal elutriation) and vital staining properties (mitochondria-binding dye rhodamine 123 and DNA-binding dye Hoechst 33342).

Procedures for separation may include magnetic separation, using antibody or lectin-coated magnetic beads, affinity chromatography, "panning" with antibody attached to a solid matrix or any other convenient technique. Other techniques providing particularly accurate separation include fluorescence activated cell sorting, this technique also being applicable to the separation of cells based on morphological characteristics which are discernible by forward vs side light scatter. Whereas these techniques can be applied in the context of either positive or negative selection, additional negative selection techniques include, but are not limited to, the site-directed administration of a cytolytic, apoptotic or otherwise toxic agent. This may be most conveniently achieved via the coupling of such an agent to a monoclonal antibody in order to facilitate its directed delivery. In another example, opsonization with an antibody followed by complement administration may achieve the same outcome.

These techniques can be performed as either a single-step or multi-step protocol in order to achieve the desired level of purification or enrichment.

Since the proliferative capacity of the cells and tissues of the present invention may be essential to a given use, for example to repair damaged vasculature, or to test the effects of a therapeutic treatment regime, it may be desirable to screen for cells which are displaying an adequate level of proliferative capacity. Determining the proliferative capacity of cells can be performed by numerous standard techniques. Preferably, determination of proliferation is effected via $^3$[H]-thymidine or $^{125}$I-iododeoxyuridine uptake assay. Alternatively, colorimetric assays employing metabolic dyes such as XTT or direct cell counting may be employed to ascertain proliferative capacity. Proliferation capacity can also be evaluated via the expression of cell cycle markers such as Ki-67.

As detailed hereinbefore, the method of the present invention can be performed either in vitro or in vivo. In terms of in vitro technology, there is now provided means of routinely and reliably producing EPC- or MSC-derived cells on either a small scale or on a larger scale. In terms of small-scale production, which may be effected in tissue culture flasks for example, this may be particularly suitable for producing populations of cells for a given individual and in the context of a specific condition. In terms of large-scale production, one means of achieving such production in accordance with the method of the invention is via the use of a bioreactor.

Bioreactors are designed to provide a culture process that can deliver medium and oxygenation at controlled concentrations and rates that mimic nutrient concentrations and rates in vivo. Bioreactors have been available commercially for many years and employ a variety of types of culture technologies. Of the different bioreactors used for mammalian cell culture, most have been designed to allow for the production of high density cultures of a single cell type and as such find use in the present invention. Typical application of these high-density systems is to produce as the end product, a conditioned medium produced by the cells. This is the case, for example, with hybridoma production of monoclonal antibodies and with packaging cell lines for viral vector production. However, these applications differ from applications where the therapeutic end product is the harvested cells themselves, as in the present invention.

Once operational, bioreactors provide automatically regulated medium flow, oxygen delivery, and temperature and pH controls, and they generally allow for production of large numbers of cells. Bioreactors thus provide economies of labour and minimization of the potential for mid-process contamination, and the most sophisticated bioreactors allow for set-up, growth, selection and harvest procedures that involve minimal manual labour requirements and open processing steps. Such bioreactors optimally are designed for use with a homogeneous cell mixture or aggregated cell populations as contemplated by the present invention. Suitable bioreactors for use in the present invention include but are not limited to those described in U.S. Pat. Nos. 5,763,194, 5,985,653 and 6,238,908, 5,512,480, 5,459,069, 5,763,266, 5,888,807 and 5,688,687.

With any large volume cell culture, several fundamental parameters require almost constant control. Cultures must be provided with the medium that allows for, in the present invention, stem cell maintenance, endothelial progenitor cell proliferation, endothelial progenitor cell differentiation (perhaps in the context of several separate differentiation cultures and conditions) as well as final cell culture/preservation. Typically, the various media are delivered to the cells by a pumping mechanism in the bioreactor, feeding and exchanging the medium on a regular basis. The exchange process allows for by-products to be removed from the culture. Growing cells or tissue also requires a source of oxygen. Different cell types can have different oxygen requirements. Accordingly, a flexible and adjustable means for providing oxygen to the cells is a desired component.

Depending on the particular culture, even distribution of the cell population and medium supply in the culture chamber can be an important process control. Such control is often achieved by use of a suspension culture design, which can be effective where cell-to-cell interactions are not important. Examples of suspension culture systems include various tank reactor designs and gas-permeable plastic bags. For cells that do not require assembly into a three-dimensional structure or require proximity to a stromal or feeder layer such suspension designs may be used.

Efficient collection of the cells at the completion of the culture process is an important feature of an effective cell culture system. One approach for production of cells as a product is to culture the cells in a defined space, without physical barriers to recovery, such that simple elution of the cell product results in a manageable, concentrated volume of cells amenable to final washing in a commercial, closed system cell washer designed for the purpose. Optimally, the system would allow for addition of a pharmaceutically acceptable carrier, with or without preservative, or a cell storage compound, as well as provide efficient harvesting into appropriate sterile packaging. Optimally the harvest and packaging process may be completed without breaking the sterile barrier of the fluid path of the culture chamber.

With any cell culture procedure, a major concern is sterility. When the product cells are to be transplanted into patients (often at a time when the patient is ill or immunocompromised), absence of microorganisms is mandated. An advantage of the present cell production device over manual processes is that, as with many described bioreactor systems, once the culture is initiated, the culture chamber and the fluid pathway is maintained in a sterile, closed environment.

If desired, the cells of the present invention (e.g., EPC and/or MSC) can be genetically engineered or molecularly modified to express an heterologous gene, illustrative examples of which include factors or proteins that, for example, directly or indirectly inhibit thrombogenesis, restenosis or platelet adhesion, or that enhance cell viability or that have anti-inflammatory properties. For example, a vector (e.g., a viral vector, such as an adenoviral vector, an adeno-associated viral vector, an AAV chimeric vector or a retroviral vector or pseudotyped viral vector) can be constructed comprising an expression cassette containing a gene, pseudogene, mutant gene, such as dominant negative gene, or a gene-silencing construct, e.g., short hairpin RNA (shRNA) or microRNA (miRNA). Suitable expression cassettes can be constructed using an array of conventional cloning methods. While the use of gene delivery via viral vectors is preferred, non-viral methodologies can also be used, e.g., plasmid or cosmid DNA delivery via liposomal reagents, lipoplexes or polyplexes, electroporation, sonoporation, hydrodynamic gene delivery, use of a 'gene gun', and nucleofector techniques and nanoparticle delivery.

As used herein, the term "gene" refers to any and all discrete coding regions of a genome, as well as associated non-coding and regulatory regions. The gene is also intended to mean an open reading frame encoding one or more specific polypeptides, and optionally comprising one or more introns, and adjacent 5' and 3' non-coding nucleotide sequences involved in the regulation of expression. In this regard, the gene may further comprise control signals such as promoters, enhancers, termination and/or polyadenylation signals that are naturally associated with a given gene, or heterologous control signals. Accordingly, the term "gene" includes and encompasses a nucleic acid molecule capable of being used to produce mRNA, antisense RNA, siRNA, shRNA, miRNA and the like. Genes may or may not be capable of being used to produce a functional protein. Genes can include both coding and non-coding regions.

The term "heterologous gene" is used herein to describe genetic material that has been or is about to be artificially introduced into a genome of a host cell (e.g., the EPC or MSC of the present invention) and that is transmitted to the progeny of that host cell. The heterologous gene will typically comprise a polynucleotide that is capable of being transcribed into RNA and optionally, translated and/or expressed under appropriate conditions. In some embodiments, it confers a desired property to the recombinant host cell into which it is introduced, or otherwise leads to a desired therapeutic or diagnostic outcome. In some embodiments, it is transcribed into a molecule that interferes with transcription or translation (e.g., antisense molecule) or mediates RNA interference (e.g., siRNA or shRNA).

In specific embodiments, the cells of the present invention (e.g., EPC and/or MSC) are advantageously engineered to over-express thrombomodulin (TM) in view of its properties as an anticoagulant and as an anti-inflammatory molecule. TM participates in one of the most important anticoagulant feedback loops in blood coagulation, whereby the proteolytic activity of thrombin is harnessed to prevent further thrombin generation. Additionally, TM-induced generation of activated protein C exerts anti-inflammatory and anti-apoptotic functions on endothelial cells (Dahlback and Villoutreix (2005) Arterioscler. Thromb. Vasc. Biol. 25(7): 1311-1320).

In some embodiments, the invention includes cells (e.g., EPC and/or MSC) that are genetically engineered to express other polypeptides/proteins, including, but not limited to, the endothelial cell protein C receptor (EPCR), which increases the protein C (PC) activation rate by thrombin-TM complexes (Fukudome et al. (1994) J Biol Chem 269:26486-91); endothelial nitric oxide synthase, which synthesizes the L-arginine derivative nitric oxide and, therefore, acts as a potent platelet adhesion and aggregation inhibitor and reduces cytokine and endotoxin-induced expression of tissue factor (Yang et al. (2002) Circulation 101:2144-8); heparin-like molecules, which through their interaction with antithrombin and heparin cofactor II counteract prothrombotic proteins (Stern et al. (1985) J Exp Med 162:1223-35); subspecies of heparin cofactor II, which act by inhibiting the procoagulant thrombin molecule (Shirk et al. (1996) Arterioscler Thromb Vasc Biol 16:1138-46); plasminogen activators (e.g., tissue plasminogen activator and urokinase-type plasminogen activator), which convert plasminogen to plasmin and, therefore, allow for fibrin breakdown; tissue factor pathway inhibitor, which inhibits the activated coagulation factor VIIa in combination with tissue factor (Osterud et al. (1995) Thromb Haemost 73:873-5); annexin V, which, as a nonglycosylated protein with high affinity to negatively charged membrane phospholipids, acts by displacing coagulation factors and inhibiting platelet adhesion (He et al. (2008) J Biol Chem 283:19192-200); prostacyclin (PGI2), which, through upregulating cyclic adenosine monophosphate, inhibits platelet aggregation (Willis et al. (1986) Lancet 2:682-3); anti-inflammatory proteins, such as transforming growth factor-beta 1 (Smith et al. (1996) J Immunol 157:360-8); Interleukin-10 (Mulligan et al. (1993) J Immunol 151:5666-74); Interleukin-4 (Mulligan et al. (1993) supra); high-density lipoprotein (Cockerill et al. (2001) Circulation 103:108-12); Protein Z, which forms a complex with ZPI and binds to phospholipid surfaces where they inhibit activated factors IX, X and XI (Corral et al. (2007) Br. J. Haematol. 137:99-108) and other proteins, factors and receptors involved in the homing, anti-coagulation-, fibrinolytic- and anti-inflammatory pathways. In some embodiments, the genetically engineered or modified cells (e.g., EPC and/or MSC) express homing molecules that enhance homing of the cells to a target tissue or body location including target (e.g., injured or inflamed) vasculature. In illustrative examples of this type, the homing molecules are selected from chemokine receptors, integrin receptors, interleukin receptors, growth factor receptors, and hormone receptors. In specific embodiments, homing molecules for genetically modified EPC are suitably selected from chemokine (C—X—C motif) receptor 4(CXCR4), CX3C chemokine receptor 1 (CX3CR1), C—C chemokine receptor type 5 (CCR5) and insulin-like growth factor 2 receptor (IGFR2), β2-integrin and CXCR2.

The genetic engineering of the subject cells (e.g., EPC and/or MSC) is not restricted to over-expressing or addition of advantageous genes, but also includes the inhibition, down-regulation and 'knockout' of disadvantageous genes, which include but are not limited to those encoding plasminogen activator inhibitor-1, which inhibits the action of plasminogen conversion to plasmin (Rijken et al. (2009) J Thromb Haemost 7:4-13); tissue factor, which can be expressed on activated or damaged endothelial cells and plays a pivotal role in activation of the extrinsic coagulation pathway (Osterud et al. (1995) Thromb Haemost 73:873-5); platelet activating factor receptors (Derian et al. (2003) Expert Opin Investig Drugs 12:209-2); pro-inflammatory interleukins; and cell surface phospholipids, which enhance the adhesion of coagulation proteins, as well as other proteins, factors and receptors involved in the coagulation, anti-fibrinolytic and pro-inflammatory pathways.

Thus, the development of the present invention has now facilitated the development of means for therapeutically or prophylactically treating subjects. In particular, and in the context of the preferred embodiments of the present invention, means for treating patients exhibiting inadequate, insufficient or aberrant endothelial cell functioning is provided based on administering to these subjects endothelial progenitor cells or partially or fully differentiated EPC-derived cells, which endothelial progenitor cell have been isolated according to the method of the present invention. Similarly, where mesenchymal stem cell differentiation is required, the present method provides a source of fetal or maternal mesenchymal stem cells.

This method can be applied to a wide range of conditions including wound healing (e.g., healing of skin wound, diabetic foot or ulcer, gangrene or diabetic wounds), ischemia (e.g., critical leg ischemia, critical kidney ischemia, mesenteric ischemia, limb ischemia, transient ischemia) myocardial infarction, stroke, congestive heart failure, peripheral vascular obstructive disease, reperfusion injury, and any other condition in which angiogenesis or vasculogenesis is desired, for example to repair or regenerate a tissue.

Accordingly, in various aspects, the present invention contemplates methods of repairing or regenerating a tissue in a subject, comprising contacting the tissue with an EPC, population enriched for EPC or implant of the present invention, thereby repairing or regenerating the tissue. In specific embodiments, these methods are for enhancing angiogenesis and/or vasculogenesis in the subject. Suitably, the tissue is a muscle tissue, skeletal muscle tissue, cardiac tissue, neural tissue, liver tissue, pancreatic tissue, bone tissue, cartilage, renal tissue, eye tissue, skin tissue or a tissue characterized by excess cell death.

In some embodiments, the subject has or is at risk of developing a disease selected from the group consisting of myocardial infarction, congestive heart failure, peripheral vascular obstructive disease, ischemia, limb ischemia, stroke, transient ischemia, reperfusion injury, arterial dissection, aneurysm and wounds, inclusive of skin wounds, diabetic foot or ulcers, gangrene and diabetic wounds.

Thus, in related aspects, the present invention encompasses methods for ameliorating ischemia related tissue damage in a subject, which methods comprise: (a) administering to the subject an EPC, population enriched for EPC or implant of the present invention; and (b) enhancing angiogenesis or vasculogenesis in a tissue of the subject, thereby ameliorating ischemia related tissue damage in the subject. In some embodiments, the ischemia related tissue damage is associated with heart failure, myocardial infarction, other ischemic heart diseases, limb ischemia, stroke, transient ischemia, or reperfusion injury.

In other related aspects, the present invention contemplates methods for ameliorating heart failure in a subject, wherein the methods comprise: (a) administering to a cardiac tissue of the subject an EPC, population enriched for EPC or implant of the present invention; and (b) enhancing angiogenesis or vasculogenesis in the cardiac tissue of the subject, thereby ameliorating heart failure in the subject.

The present invention also resides in methods for enhancing wound healing in a tissue of a subject, wherein the methods comprise: (a) administering to the tissue an EPC, population enriched for EPC or implant of the present invention; and (b) increasing angiogenesis thereby increasing wound healing.

Methods of treatment according to the present invention may include measuring the rate of generation of endothelial cells at the desired site at one or more time points after transplantation as well as obtaining information as to the performance of the newly formed endothelial cell-containing tissues in the subject. Parameters measured can include the survival, localization, and number of administered cells present at the transplantation site in the patient. The degree cell engraftment or reconstitution may be determined using any of a variety of scanning techniques, e.g., computerized axial tomography (CAT or CT) scan, magnetic resonance imaging (MRI), Doppler imaging or positron emission tomography (PET) scans. Functional integration of transplanted cells according to the invention into a subject can be assessed by examining restoration of the function that was damaged or diseased or augmentation of a function associated with the presence of endothelial cells. Cell transplant engraftment, localization and survival can also be done by removing a portion of the target tissue and examining it visually or through a microscope (e.g., in post mortem analysis).

Also facilitated is the in vitro generation of vasculature, such as via the use of scaffolds, for use in the transplantation and repair of vasculature. Still further, the present method provides a source of cells for use in the context of inflammation, such as graft vs. host disease, tissue repair, cancer and organ failure. Also provided is means to incorporate cells in biomaterials and matrixes for the formation of orgonotypic cultures ex vivo.

Reference to a condition characterized by "aberrant endothelial cell functioning" should be understood as a reference to any condition which is due, at least in part, to a defect or unwanted or undesirable outcome in terms of the functioning or development of endothelial cells. This may correspond to either a homogeneous or heterogeneous population of cells. The subject defect should be understood as a reference to any structural or functional feature of the cell that is either not normal or otherwise undesirable, including the production of insufficient numbers of these cells. A corresponding definition applies to "aberrant mesenchymal-derived cell functioning".

Accordingly, another aspect of the present invention is directed to a method of therapeutically and/or prophylactically treating a condition in a mammal, said method comprising administering to said mammal an effective number of endothelial progenitor cells or partially or fully differentiated EPC-derived cells, which endothelial progenitor cells have been isolated according to the method of the present invention.

In another aspect, the present invention is directed to a method of therapeutically and/or prophylactically treating a condition in a mammal, said method comprising administering to said mammal an effective number of mesenchymal stem cells or partially or fully differentiated MSC-derived cells, which mesenchymal stem cells have been isolated according to the method of the present invention.

Reference to "administering" to an individual an effective number of the cells of the invention should be understood as a reference to introducing into the mammal an ex vivo population of cells which have been isolated according to the method of the invention. It should be understood that where one administers endothelial progenitor cells or mesenchymal stem cells in vivo the stimulus necessary to induce differentiation may be present in situ or it may be necessary to administer additional stimuli, such as appropriate cytokines, in order to achieve endothelial cell differentiation.

Preferably, said method is performed by in vivo administration of endothelial progenitor cells to a localized site in need of vasculogenesis. To this end, one may harvest autologous tissue, isolate the endothelial progenitor cells, optionally store the cells (e.g., cryopreservation) and thereafter implant these cells at the site in need of vasculogenesis.

In accordance with these treatment methods, the subject cells are preferably autologous cells that are identified, isolated and/or differentiated to the requisite phenotype ex vivo and transplanted back into the individual from which they were originally harvested. However, it should be understood that the present invention nevertheless extends to the use of cells derived from any other suitable source where the subject cells exhibit the same major histocompatability profile as the individual who is the subject of treatment. Accordingly, such cells are effectively autologous in that they would not result in the histocompatability problems that are normally associated with the transplanting of cells exhibiting a foreign MHC profile. Such cells should be understood as falling within the definition of "autologous". For example, under certain circumstances it may be desirable, necessary or of practical significance that the subject cells are isolated from a genetically identical twin. The cells may also have been engineered to exhibit the desired major histocompatability profile. The use of such cells overcomes the difficulties that are inherently encountered in the context of tissue and organ transplants. However, where it is not possible or feasible to isolate or generate autologous cells, it may be necessary to utilize allogeneic stem cells. "Allogeneic" cells are those that are isolated from the same species as the subject being treated but that exhibit a different MHC profile. Although the use of such cells in the context of therapeutics would likely necessitate the use of immunosuppression treatment, this problem can nevertheless be minimized by use of cells which exhibit an MHC profile exhibiting similarity to that of the subject being treated, such as a cellular population which has been isolated/generated from a relative such as a sibling, parent or child. The present invention should also be understood to extend to xenogeneic transplantation. That is, the cells that are isolated in accordance with the method of the invention and introduced into a patient, are isolated from a species other than the species of the subject being treated.

Without limiting the present invention to any one theory or mode of action, even partial restoration of the vascular functioning which is not being provided by the aberrant cellular population will act to ameliorate the symptoms of many conditions. Accordingly, reference to an "effective number" means that number of cells necessary to at least partly attain the desired effect, or to delay the onset of, inhibit the progression of, or halt altogether the onset or progression of the particular condition being treated. Such amounts will depend, of course, on the particular conditions being treated, the severity of the condition and individual patient parameters including age, physical conditions, size, weight, physiological status, concurrent treatment, medical history and parameters related to the disorder in issue. One skilled in the art would be able to determine the number of cells and tissues of the present invention that would constitute an effective dose, and the optimal mode of administration thereof without undue experimentation, this latter issue being further discussed hereinafter. These factors are well known to those of ordinary skill in the art and can be addressed with no more than routine experimentation. It is preferred generally that a maximal cell number be used, that is, the highest safe number according to sound medical judgment. It will be understood by those of ordinary skill in the art, however, that a lower cell number may be administered for medical reasons, psychological reasons or for any other reasons.

As hereinbefore discussed, it should also be understood that although the method of the present invention encompasses within its scope the introduction of transitioned or fully or partially differentiated cells to an individual suffering a condition as herein defined, it is not necessarily the case that every cell of the population introduced to the individual will have acquired the EPC- or MSC-derived phenotype of interest. For example, where an endothelial progenitor cell or mesenchymal stem cell population has undergone transition to a somatic endothelial cell and is administered in total, there may exist a proportion of cells that have not undergone transition to a cell exhibiting the requisite phenotype. The present invention is therefore achieved provided that the relevant portion of the cells thereby introduced constitute the "effective number" as defined above. However, in a particularly preferred embodiment the population of cells which have undergone differentiation will be subjected to the identification of successfully differentiated cells, their isolation and introduction to the subject individual. This provides a means for selecting either a heterogeneous population of EPC- or MSC-derived cells or to select out a specific subpopulation of cells for administration. The type of method that is selected for application will depend on the nature of the condition being treated. However, it is expected that in general it will be desirable to administer a pure population of cells in order to avoid potential side effects. Alternatively, in some instances it may be feasible to subject a population of endothelial progenitor cells to differentiation and provided that this population, as a whole, is shown to exhibit the requisite functional activity, this population as a whole may be introduced into the subject individual without the prior removal of irrelevant cell types. Accordingly, reference to "an effective number", in this case, should be understood as a reference to the total number of cells required to be introduced such that the number of differentiated cells is sufficient to produce the level of activity which achieves the object of the invention, being the treatment of the subject condition.

The cells may be introduced into an individual by any suitable method. For example, cell suspensions may be introduced by direct injection or inside a blood clot whereby the cells are immobilized in the clot thereby facilitating transplantation. The cells may also be encapsulated prior to transplantation. Encapsulation is a technique that is useful for preventing the dissemination of cells which may continue to proliferate (i.e. exhibit characteristics of immortality) or for minimizing tissue incompatibility rejection issues. However, the usefulness of encapsulation will depend on the function that the transplanted cells are required to provide.

For example, if the transplanted cells are required primarily for the purpose of secreting a soluble factor, a population of encapsulated cells will likely achieve this objective. However, if the transplanted cells are required for the development of vasculature, the cells will be required to integrate with the existing vasculature. Encapsulated cells would not be able to do this efficiently.

The cells that are administered to the patient can be administered as single or multiple doses by any suitable route. Preferably, and where possible, a single administration is utilized. Administration via injection can be directed to various regions of a tissue or organ, depending on the type of repair required.

It would be appreciated that in accordance with these aspects of the present invention, the cells which are administered to the patient may take any suitable form, such as being in a cell suspension or taking the form of a tissue graft (e.g. vasculature). In terms of generating a single cell suspension, the differentiation protocol may be designed such that it favors the maintenance of a cell suspension. Alternatively, if cell aggregates or tissues form, these may be dispersed into a cell suspension. In terms of utilizing a cell suspension, it may also be desirable to select out specific subpopulations of cells for administration to a patient. To the extent that it is desired that a tissue is transplanted into a patient, this will usually require surgical implantation (as opposed to administration via a needle or catheter). Alternatively, a portion, only, of this tissue could be transplanted. In another example, engineered tissues can be generated via standard tissue engineering techniques, for example by seeding a tissue engineering scaffold having the designed form with the cells of the present invention and culturing the seeded scaffold under conditions enabling colonization of the scaffold by the seeded cells and tissues, thereby enabling the generation of the formed tissue. The formed tissue is then administered to the recipient, for example using standard surgical implantation techniques. Suitable scaffolds may be generated, for example, using biocompatible, biodegradable polymer fibers or foams, comprising extracellular matrix components, such as laminins, collagen, fibronectin, etc. Detailed guidelines for generating or obtaining suitable scaffolds, culturing such scaffolds and therapeutically implanting such scaffolds are available in the literature (for example, refer to Kim S. S. and Vacanti J. P., 1999. *Semin Pediatr Surg.* 8:119, U.S. Pat. No. 6,387,369 to Osiris, Therapeutics, Inc.; U.S. Pat. App. No. US20020094573A1 to Bell E.).

In accordance with the method of the present invention, other proteinaceous or non-proteinaceous molecules may be co-administered either with the introduction of the subject cells or prior or subsequently thereto. By "co-administered" is meant simultaneous administration in the same formulation or in different formulations via the same or different routes or sequential administration via the same or different routes. By "sequential" administration is meant a time difference of from seconds, minutes, hours or days between the introduction of these cells and the administration of the proteinaceous or non-proteinaceous molecules or the onset of the functional activity of these cells and the administration of the proteinaceous or non-proteinaceous molecule. Examples of circumstances in which such co-administration may be required include, but are not limited to:

(i) When administering non-syngeneic cells or tissues to a subject, there usually occurs immune rejection of such cells or tissues by the subject. In this situation it would be necessary to also treat the patient with an immunosuppressive regimen, preferably commencing prior to such administration, so as to minimize such rejection. Immunosuppressive protocols for inhibiting allogeneic graft rejection, for example via administration of cyclosporine A, immunosuppressive antibodies, and the like are widespread and standard practice.

(ii) Depending on the nature of the condition being treated, it may be necessary to maintain the patient on a course of medication to alleviate the symptoms of the condition until such time as the transplanted cells become integrated and fully functional. Alternatively, at the time that the condition is treated, it may be necessary to commence the long term use of medication to prevent re-occurrence of the damage. For example, where the subject damage was caused by high cholesterol (such as occurs in the context of atherosclerosis), the ongoing use of cholesterol lowering drugs may be required.

It should also be understood that the method of the present invention can either be performed in isolation to treat the condition in issue or it can be performed together with one or more additional techniques designed to facilitate or augment the subject treatment. These additional techniques may take the form of the co-administration of other proteinaceous or non-proteinaceous molecules, as detailed hereinbefore.

Another aspect of the present invention is directed to the use of a population of endothelial progenitor cells or EPC-derived cells, which cells have been isolated in accordance with the method of the present invention, in the manufacture of a medicament for the treatment of a condition in a mammal.

Yet another aspect of the present invention is directed to an isolated population of endothelial progenitor cells or EPC-derived cells which endothelial progenitor cells have been isolated in accordance with the method of the present invention.

Another aspect of the present invention is directed to the use of a population of mesenchymal stem cells or MSC-derived cells, which cells have been isolated in accordance with the method of the present invention, in the manufacture of a medicament for the treatment of a condition in a mammal.

Yet another aspect of the present invention is directed to an isolated population of mesenchymal stem cells of MSC-derived cells which mesenchymal stem cells have been isolated in accordance with the method of the present invention.

In a related aspect of the present invention, the subject undergoing treatment or prophylaxis may be any human or animal in need of therapeutic or prophylactic treatment. In this regard, reference herein to "treatment" and "prophylaxis" is to be considered in its broadest context. The term "treatment" does not necessarily imply that a mammal is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity of the onset of a particular condition. "Treatment" may also reduce the severity of an existing condition.

The development of a method for generating endothelial progenitor cells, EPC-derived cells mesenchymal stem cells and MSC-derived cells in vitro has now facilitated the development of in vitro based screening systems for testing the effectiveness and toxicity of existing or potential treatment or culture regimes.

Thus, according to yet another aspect of the present invention, there is provided a method of assessing the effect of a treatment or culture regime on the phenotypic or functional state of endothelial progenitor cells or EPC-derived cells said method comprising subjecting said endothelial progenitor cells or EPC-derived cells, which endothelial progenitor cells have been isolated in accordance with the method hereinbefore defined, to said treatment regime and screening for an altered functional or phenotypic state.

Aspects of the present invention relate to the therapeutic uses of the EPC of the present invention and in specific embodiments, the present invention provides compositions containing EPC as detailed above and elsewhere herein in a form that is therapeutically useful. As such, the subject invention includes compositions containing isolated EPC or isolated populations of cells enriched for EPC and a pharmaceutically acceptable carrier. By "pharmaceutically acceptable carrier" is meant any composition that can be combined with the isolated EPC in a manner that is compatible with the therapeutic use of the EPC. Non-limiting examples of therapeutic uses of EPC as well as pharmaceutically acceptable carriers are provided below (see, also US Patent Application Publication 2004/0009589, which is incorporated herein by reference in its entirety).

Thus, the EPC of the present invention, or cells derived therefrom, may be used in any of a number of therapeutic applications, including for example therapeutic applications that require vasculogenesis and/or angiogenesis. Angiogenesis and vasculogenesis are responsible for the development of the vascular system in embryos. Vasculogenesis refers to the de novo development of blood vessels from EPC or angioblasts that differentiate into endothelial cells. In contrast, angiogenesis refers to the formation of new vasculature from preexisting blood vessels through proliferation, migration, and remodeling of fully differentiated endothelial cells. In specific embodiments, the EPC of the present invention, or cells derived therefrom, are useful for repairing blood and/or lymphatic vasculature including for the repair of ischemic limb and heart, or as targeting vectors for delivery of therapeutic agents to vascular sites. In specific embodiments, the EPC of the present invention are useful for treating myocardial infarction, congestive heart failure, peripheral vascular obstructive disease, ischemia, limb ischemia, stroke, transient ischemia, reperfusion injury, and wounds, inclusive of skin wounds, diabetic foot or ulcers, gangrene and diabetic wounds.

EPC can be administered to a subject in any therapeutically acceptable carrier. The subject to which the EPC (or cells derived therefrom) are administered may have any condition, injury or disease for which EPC would provide a therapeutic benefit. For example, if a subject has blood vascular cell damage at a specific site, e.g., the heart, the EPC may be administered to the subject at the site of damage (or in certain embodiments, systemically, where the EPC, or cells derived therefrom, home to the site of damage).

In certain therapeutic applications, the EPC may be cultured under endothelial cell-inducing conditions prior to administering the cells to the subject, illustrative examples of which include inducing endothelial cell production prior to transplantation. For instance, EPC may be induced to form vascular endothelial cells, e.g., on a medical or surgical device, scaffold or matrix or other structure (e.g., a tube), and then be transplanted into a subject at a site in need of endothelial cells. Any convenient endothelial cell producing condition may be employed in such embodiments.

In some embodiments, the EPC of the present invention are combined with an implantable cell support substrate, device and/or pharmaceutically acceptable carrier. The cell support substrate may be a polymer matrix, illustrative examples of which include gels such as but not limited to MATRIGEL, from Becton-Dickinson, which is a solubilized basement membrane matrix extracted from the EHS mouse tumor (Kleinman et al. (1986) Biochem. 25:312). In other embodiments, the gel may be a collagen I gel. Such a gel may also include other extracellular matrix (ECM) components, such as glycosaminoglycans, fibrin, fibronectin, proteoglycans, and glycoproteins. The gel may also include basement membrane components such as collagen IV and laminin. Enzymes such as proteinases and collagenases may be added to the gel, as may cell response modifiers such as growth factors and chemotactic agents.

The EPC of the present invention (or endothelial cells derived therefrom) mixed with a gel or simply with a liquid carrier such as phosphate buffered saline (PBS), may be injected directly into a tissue site where angiogenesis/vasculogenesis is desired. For example, the cells may be injected into ischemic tissue in the heart or other muscle, where the cells will organize into tubules that will anastomose with existing cardiac vasculature to provide a blood supply to the diseased tissue. Other tissues may be vascularized in the same manner. The cells will incorporate into neovascularization sites in the ischemic tissue and accelerate vascular development and anastomosis (see, Kawamoto et al., (2001) Circulation 103: 634-7). It is intended that the cells according to the invention be used to vascularize all sorts of tissues, including connective tissue, muscle tissue, nerve tissue, and organ tissue. Non-blood duct networks may be found in many organs, such as the liver and pancreas, and the techniques of the invention may be used to engineer or promote healing in such tissues as well. For example, embryonic endothelial cells injected into the liver can develop into tubular networks around which native hepatocytes can develop other liver structures.

The EPC may also be used to help heal cardiac vasculature following angioplasty. For example, a catheter can be used to deliver embryonic endothelial cells to the surface of a blood vessel following angioplasty or before insertion of a stent. Alternatively, the stent may be seeded with embryonic endothelial cells. Blood vessels treated with adult endothelial cells exhibit accelerated re-endothelialization, preventing restenosis in the injured vessel (Parikh et al. (2000) Advanced Drug Delivery Reviews, 42:139-161). In other embodiments, embryonic endothelial cells may be seeded into a polymeric sheet and wrapped around the outside of a blood vessel that has undergone angioplasty or stent insertion (Nugent et al. (2001) J. Surg. Res., 99:228-234). The cells may also be mixed with a gel and infused into the polymer sheet instead of directly seeded onto the matrix.

The present invention also contemplates stiffer implants in which the EPC are seeded onto a polymer matrix, for example, a sponge or mesh, which is then implanted into the desired tissue site. Alternatively, the cells may be mixed with a gel which is then absorbed onto the interior and exterior surfaces of the matrix and which may fill some of the pores of a spongy or other porous matrix. Capillary forces will retain the gel on the matrix before hardening, or the gel may be allowed to harden on the matrix to become more self-supporting. Illustrative biocompatible polymer matrices include any biocompatible synthetic, semi-synthetic material, including plastics and other polymers. In some embodiments, the biocompatible polymer matrix may be made from absorbable or non-absorbable materials. Materials useful for making biocompatible polymer matrices include, for example, poly(ethylene), polyesters, poly(propylene), poly (propylene) polyesters such as poly(propylene) fumarate, polystyrene, polytetrafluoroethylene (PTFE), nylon, polypropylene/PTFE, polypropylene/cellulose, polypropylene/monochryal, polyester/collagen, poly(acrylate), poly(methyl methacrylate), poly(hydroxyethyl methacrylate), poly(vinyl alcohol), poly(carbonate), poly(trimethylene carbonate), poly(ethylene-co-vinyl acetate), poly(ether urethane), poly (ester urethane), poly(arylate), poly(imide), poly(anhydride-co-imide), poly(amino acid), polydepsipeptide, poly(phosphazene), poly(glycolic acid), poly(lactic acid), poly (lactide-co-glycolide), poly($\varepsilon$-caprolactone), poly(p-dioxanone), poly(lactide-co-glycolide), poly($\varepsilon$-caprolactone-co-glycolide), poly(glycolide-co-trimethylene carbonate), lactide/tetramethylglycolide copolymer, lactide/trimethylene carbonate copolymer, lactide-$\delta$-valerolactone copolymer, lactide ($\varepsilon$-captrolactone copolymer), poly(lactide)/polyethylene oxide copolymer, unsymmetrically 3,6-substituted poly(1,4-dioxane-2,5-dione), poly($\beta$-alkanoic acids) such as poly($\beta$-hydroxybutyrate), poly($\beta$-hydroxybutyrate)/($\beta$-hydroxyvalerate) copolymer, poly($\beta$-maleic acid) and poly($\beta$-hydroxypropionate), poly($\delta$-valerolatone), methylmethacrylate-N-vinyl pyrrolidone copolymer, polyesteramide, polyesters of oxalic acid, polydihydropyran, polyalkyl-2-cyanoacrylate, composites thereof, cellulosic materials, and combinations thereof.

In certain embodiments, the polymer matrix is biodegradable. Suitable biodegradable matrices are well known in the art and include collagen-GAG, collagen, fibrin, PLA, PGA, and PLA-PGA co-polymers. Additional biodegradable materials include poly(anhydrides), poly(hydroxy acids), poly(ortho esters), poly(propylfumerates), poly(caprolactones), polyamides, polyamino acids, polyacetals, biodegradable polycyanoacrylates, biodegradable polyurethanes and polysaccharides. Non-biodegradable polymers may also be used as well. Other non-biodegradable, yet biocompatible polymers include polypyrrole, polyanilines, polythiophene, polystyrene, polyesters, non-biodegradable polyurethanes, polyureas, poly(ethylene vinyl acetate), polypropylene, polymethacrylate, polyethylene, polycarbonates, and poly (ethylene oxide). Those skilled in the art will recognize that this is an exemplary, not a comprehensive, list of polymers appropriate for tissue engineering applications.

In some embodiments, the matrix may be formed with a microstructure similar to that of the ECM that is being replaced. Mechanical forces imposed on the matrix by the surrounding tissue will influence the cells on the artificial matrix and promote the regeneration of ECM with the proper microstructure. The cross-link density of the matrix may also be regulated to control both the mechanical properties of the matrix and the degradation rate (for degradable scaffolds). The shape and size of the final implant should be adapted for the implant site and tissue type. The matrix may serve simply as a delivery vehicle for the cells or may provide a structural or mechanical function. The matrix may be formed in any shape, for example, as particles, a sponge, a tube, a sphere, a strand, a coiled strand, a capillary network, a film, a fiber, a mesh, or a sheet.

Alternatively, the EPC may be seeded onto a tubular substrate. For example, the polymer matrix may be formed into a tube or network. Such tubes may be formed of natural or synthetic ECM materials such as PLA or collagen or may come from natural sources, for example, decellularized tubular grafts. The EPC will coat the inside of the tube, forming an artificial channel that can be used for a heart bypass. In addition, use of EPC may reduce thrombosis post-implantation (see, Kaushall et al. (2001) Nat Med. 7(9)1035-40).

The EPC may be allowed to proliferate on the polymer matrix or tubular substrate before being implanted in an animal. During proliferation, mechanical forces may be imposed on the implant to stimulate particular cell responses or to simulate the mechanical forces the implant will experience in the animal. For example, a medium may be circulated through a tubular substrate in a pulsatile manner (i.e., a hoop stress) or with sufficient speed to exert a sheer stress on cells coating the inside of the tube (Kaushal (2001) supra). Alternatively, a hydrostatic force or compressive force may be imparted on an implant that will be deposited within an organ such as the liver, or a tensile stress may be imparted on an implant that will be used in a tissue that experiences tensile forces.

In some embodiments, the EPC of the present invention are administered into a subject as part of a medical device. Medical devices that can be coated with the EPC of the present invention, or cells derived therefrom, include devices that are introduced, temporarily or permanently, into a mammal for the prophylaxis or therapy or diagnosis of a medical condition, as well as wireless monitoring of physiologic parameters. Such devices include, but are not limited to, In some embodiments, the medical device is selected from vascular prostheses, vascular grafts, fixtures for connecting prosthetic organs to vascular circulation, stents including vascular and nonvascular stents (e.g., gastrointestinal, pulmonary or biliary stents), covered stents, artificial heart valves, artificial hearts, cardiac prosthesis (e.g., an artificial heart valve), a biological heart valve prosthesis (e.g., derived from animals such as pigs—xenografts can be coated with EPC to render them more biocompatible and less thrombic), venous valves, abdominal aortic aneurysm grafts, vascular filters (e.g., vena cava filter), catheters, guide wires, balloons, devices to protect against pulmonary embolism (e.g., embolic coils, embolic materials for vascular embolization, etc.), orthopedic implants (e.g., bone or joint prostheses), vascular sutures, scaffolds, smooth or porous implants, intraluminal devices, vascular prosthetic filters, pacemakers, pacemaker lead, electrodes, defibrillators, subcutaneous and/or intramuscular implants, vascular occlude, ventricular shunt, vascular sheath, drug delivery devices and ports, septal closure devices, sutures, neurological stimulators, implantable wireless sensors (e.g., blood glucose and blood pressure monitors), artificial filtration systems or other artificial organs, insulin pumps, artificial oxygenators and the like. Other illustrative examples of suitable medical device include MCAD (e.g., a left ventricular assist device (LVAD), including its inflow and outflow cannula and adapters), hemodialysis grafts, dental implants, orthopedic implants, reconstructive prostheses, implantable wireless biosensors that measure parameters including, but not limited to, pH and blood oxygenation, blood pressure, blood glucose level (for application of blood sugar control in diabetics), implantable insulin pumps, implantable artificial oxygenators, implantable artificial kidneys or filtration systems, artificial or tissue engineered urinary bladders and/or ureters, other implantable artificial organs, implantable electric devices (e.g., pacemakers), or wireless Micro-Electro-Mechanical System (MEMS). The medical device can be made, for example, of titanium or a titanium alloy, which includes shape memory alloys (e.g., Nitinol (NiTi), aluminum and vanadium alloys (Ti6Al4V) and (Ti6Al4V ELI), as well as niobium alloys (Ti6Al7Nb), iron alloys (Ti5Al2.5Fe), including, but not limited to, titanium alloys containing Nb, Ta, Zr, Mo, Fe, Si). The device can also be made of other metals, e.g., stainless steel.

The present invention also relates to methods of coating blood-contacting surfaces of implantable medical devices, as for example described above, with the EPC of the present invention or cells derived therefrom. In order to increase the rate of cell spreading, blood-contacting surfaces of implantable devices can be pre-coated with an extracellular matrix protein, such as fibronectin, collagen, vitronectin, laminin, fibrin, or any of the following components containing molecules, proteins or constructs, including proteoglycans, such as heparan sulfate, chondroitin sulfate, keratin sulfate, or non-proteoglycan polysaccharide containing molecules, such as hyaluronic acid, or any combination thereof. Blood-contacting surfaces can also be pre-coated with gelatin or a gelatin matrix or gelatin foam, e.g., Gelfoam (Pharmacia and Upjohn, Pfizer), cellulose, microfibrillar collagen, thrombin, e.g., recombinant human thrombin (Recothrom, ZymoGenetics), a fibrin sealant, e.g. Tisseel (Baxter), or fibrin gel, fibrin glue, fibrinolytically inhibited fibrin glue, adhesive glue or sealant, hydrogel. Blood-contacting surfaces can also be pre-coated with a serum protein or other blood component, or growth factor or hormone, e.g., platelet-derived growth factor BB, basic fibroblast growth factor, acidic fibroblast growth factor, or transforming growth factor beta1. Pre-coating can also be effected using a synthetic polymer, e.g., polymer of lysine, ornithine or arginine, or polymethylmethacrylate, polyacrylic acid, or L-glutamic acid-treated construct, or glutaraldehyde-preserved cellular matrix, or a biodegradable binder or coating, such as poly (DL-lactide-co-glycolide), or biodegradable polyester, e.g., polyhydroxyalkanoate, polysorbate, or poly amino acids, e.g., poly-L-lysine, or chitosan, fetuin, or cationic silica microbeads, other types of microbeads or carbon-deposition surface coating, polyethyleneterephthalate with or without alteration by plasma discharge surface modification, or covalently-attached avidin, biotinylation, or RGD peptide sequence containing molecules, structures or constructs or peptides, which are cross-linked to RGD peptides, or molecules specific to one or more EPC specific integrin binding site or synergistic binding site, e.g., the amino acid sequence DRVPHSRN or antibodies, peptides or aptamers specific to EPC, or any combination of the above. The aforementioned molecules can be physiosorbed or covalently bound to the underlying surface, e.g., titanium/titanium alloy surface, for the latter a variety of methods are available, including silanization (e.g., linkage of steel to an aminosilane cross-linker), biotinylation, covalent linkage to dopamine, etc. In addition to the proteins, molecules, polymers, structures and artificial constructs mentioned above, other cell types can be used to pre-coat the blood-contacting device surfaces to provide for a suitable matrix for EPC, including, but not limited to, fibroblasts, smooth muscle cells, stem cells, mesothelial cells, mesenchymal cells, progenitor cells, myocytes, or other cell type. It is generally desirable to pre-coat the implantable device with autologous cells to avoid rejection. Fibroblasts, for example, can be easily harvested for this purpose from a sample of the patient's skin.

The biocompatible implants of the invention may comprise at least one bioactive agent, representative examples of which include growth factors, analgesics/antipyretics, antiasthamatics, antibiotics, antidepressants, antidiabetics, antifungal agents, antihypertensive agents, anti-inflammatories, antineoplastics, antianxiety agents, immunosuppressive agents, antimigraine agents, sedatives/hypnotics, antipsychotic agents, antimanic agents, antiarrhythmics, antiarthritic agents, antigout agents, anticoagulants, thrombolytic agents, antifibrinolytic agents, antiplatelet agents and antibacterial agents, antiviral agents, antimicrobials, anti-infectives, and combination thereof. In specific embodiments, the bioactive agent is a cell response modifier such as a growth factor or a chemotactic agent. Exemplary growth factors include epidermal growth factor, bone morphogenetic protein, TGF-β, hepatocyte growth factor, platelet-derived growth factor, TGF-α, IGF-I and II, hematopoietic growth factors, heparin binding growth factor, peptide growth factors, basic and acidic fibroblast growth factors, nerve growth factor (NGF), muscle morphogenic factor (MMP) and vascular endothelial growth factor (VEGF). The particular growth factor employed should be appropriate to the desired cell activity. For example, VEGF may be used to promote differentiation of the EPC. Alternatively, the growth factor may be selected to recruit cells to the implant or to promote or inhibit specific metabolic activities of cells recruited to the implant. The regulatory effects of a large family of growth factors are well known to those skilled in the art.

In embodiments in which it is desirable to further enhance angiogenesis, endothelial cell mitogens may also be administered to the patient in conjunction with, or subsequent to, the administration of the EPC of the present invention. Endothelial cell mitogens can be administered directly, e.g., intra-arterially, intramuscularly, or intravenously, or nucleic acid encoding the mitogen may be used. See, Baffour et al., supra (bFGF); Pu et al. (1993) Circulation, 88:208-215 (aFGF); Yanagisawa-Miwa et al., supra (bFGF); Ferrara et al. (1989) Biochem. Biophys. Res. Commun., 161:851-855 (VEGF); (Takeshita et al. (1994) Circulation, 90:228-234).

The nucleic acid encoding the EC mitogen can be administered to a blood vessel perfusing the ischemic tissue or to a site of vascular injury via a catheter, for example, a hydrogel catheter, as described for example in by U.S. Pat. No. 5,652,225.

The nucleic acid also can be delivered by injection directly into the ischemic tissue using the method described in U.S. Pat. No. 6,121,246.

As used herein the term "endothelial cell mitogen" means any protein, polypeptide, mutein or portion that is capable of, directly or indirectly, inducing endothelial cell growth. Such proteins include, for example, acidic and basic fibroblast growth factors (aFGF and bFGF), vascular endothelial growth factor (VEGF), epidermal growth factor (EGF), transforming growth factor α and β (TGF-α and TFG-β), platelet-derived endothelial growth factor (PD-ECGF), platelet-derived growth factor (PDGF), tumor necrosis factor α (TNF-α), hepatocyte growth factor (HGF), insulin like growth factor (IGF), erythropoietin, colony stimulating factor (CSF), macrophage-CSF (M-CSF), granulocyte/macrophage CSF (GM-CSF) and nitric oxide synthase (NOS). See, Klagsbrun et al. (1991) Annu. Rev. Physiol., 53, 217-239; Folkmnan et al. (1992) J. Biol. Chem., 267, 10931-10934 and Symes et al. (1994) Current Opinion in Lipidology, 5, 305-312. Muteins or fragments of a mitogen may be used as long as they induce or promote EC cell growth.

In some embodiments, the endothelial cell mitogen contains a secretory signal sequence that facilitates secretion of the protein. Proteins having native signal sequences, e.g., VEGF, are desirable. Proteins that do not have native signal sequences, e.g., bFGF, can be modified to contain such sequences using routine genetic manipulation techniques. See, Nabel et al. (1993) Nature, 362, 844.

The nucleotide sequence of numerous endothelial cell mitogens, are readily available through a number of computer databases, for example, GenBank, EMBL and Swiss-Prot. Using this information, a DNA segment encoding the desired may be chemically synthesized or, alternatively, such a DNA segment may be obtained using routine procedures in the art, e.g., PCR amplification. A DNA encoding VEGF is disclosed in U.S. Pat. No. 5,332,671.

In certain situations, it may be desirable to use nucleic acids encoding two or more different proteins in order optimize the therapeutic outcome. For example, DNA encoding two proteins, e.g., VEGF and bFGF, can be used, and provides an improvement over the use of bFGF alone. Or an angiogenic factor can be combined with other genes or their encoded gene products to enhance the activity of targeted cells, while simultaneously inducing angiogenesis, including, for example, nitric oxide synthase, L-arginine, fibronectin, urokinase, plasminogen activator and heparin.

Cell-seeded implants of the present invention may be implanted into any tissue, including connective, muscle, nerve, and organ tissues. For example, an implant placed into a bony defect will attract cells from the surrounding bone, which will synthesize ECM, while the EPC form blood vessels. The blood supply for the new bone will be provided as the new ECM is formed and mineralized. An implant placed into a skin defect will promote dermis formation and provide a vascular network to supply nutrients to the newly formed skin.

Cells that are recruited to the implant may also differentiate into other cell types. Bone cell precursors migrating into a bone implant can differentiate into osteoblasts. Mesenchymal stem cells migrating into a blood vessel can differentiate into muscle cells. Endothelial cells forming tubular networks in liver can induce the formation of liver tissue.

In some embodiment, the EPC of the present invention are mixed with another cell type before implantation. The cell mixture may be suspended in a carrier such as a culture medium or in a gel as described above. Alternatively, the cells may be co-seeded onto a polymer matrix or combined with a gel that is absorbed into the matrix. For some applications, it may be desirable to seed one cell type directly onto the matrix and add the second cell type via a gel. Any ratio of EPC to the other cell type or types may be used. One skilled in the art will recognize that this ratio may be easily optimized for a particular application. Exemplary ratios of EPC to other cells are at least 10% (e.g., 1:9), at least 25%, at least 50% (e.g., 1:1), at least 75%, and at least 90%. Smaller ratios, for example, less than 10%, may also be employed.

Any cell type, including connective tissue cells, nerve cells, muscle cells, organ cells, or other stem cells, may be combined with the EPC. For example, osteoblasts may be combined with the fetal endothelial cells to promote the co-production of bone and its vasculature in a large defect. Fibroblasts combined with fetal endothelial cells and inserted into skin will produce fully vascularized dermis. Other exemplary cells that may be combined with the fetal endothelial cells of the invention include hematopoietic cells (including hematopoietic stem cells), ligament cells, lung cells, epithelial cells, smooth muscle cells, cardiac muscle cells, skeletal muscle cells, islet cells, nerve cells, hepatocytes, kidney cells, bladder cells, and bone-forming cells.

In certain embodiments, the EPC of the present invention are used to target a therapeutic agent to a desired site in a subject. Desired sites include the vasculature at sites of neoplastic cell growth, e.g., tumor cells or abnormal vascular proliferation in retinopathies, in a subject. As well known in the art, tumors include regions of endothelial cell production, including both vascular and lymphatic endothelial cells. Tumor-associated vasculature has been shown to be important for tumor growth and maintenance. Tumor-associated lymphatic vessels have been shown to act as a conduit for disseminating tumor cells to form metastases, e.g., at lymph nodes, which is of major prognostic significance for many types of cancer. As noted above, EPC according to aspects of the present invention are bipotent, i.e., can develop into either vascular or lymphatic endothelial cells. Therefore, EPC according to aspects of the present invention find use as targeting vectors for delivering therapeutic agents to lymphatic and/or vascular endothelial cell sites in tumors. One example of employing EPC as anti-tumor or anti-angiogenic delivery vectors includes genetically modifying EPC to express one or more anti-tumor (or cell toxic) protein or factor, including: cytokines, hormones or other signal transducing agents; antibody or antibody fragments, and the like. Another example of employing EPC as anti-tumor delivery vectors includes conjugating or coating EPC with anti-tumor factors or other toxic agents, including: antibodies or antibody fragments, cytokines, hormones, radioactive agents, cytotoxic agents, chemotherapeutic agents, and the like. No limitation in this regard is intended.

The endothelial progenitor cells of the present invention are useful for regenerating or repairing tissues affected by a variety of diseases characterized by an increase in cell death or a decrease in cell number or function. In particular, transplantation of these cells is useful for repairing ischemic limb and heart. Such cells may also be used for the treatment or prevention of cardiovascular diseases, such as myocardial infarction, congestive heart failure, peripheral vascular obstructive diseases, various types of peripheral neuropathies including but not limited to diabetic, ischemic, toxic or chemical-induced neuropathies, stroke (cerebrovascular diseases), liver failure, renal failure, islet cell transplantation, bone and joint diseases or any degenerative disease which requires endothelial progenitor cell therapy.

In still another aspect of the present invention, there is provided a method of assessing the effect of a treatment or culture regime on the phenotypic or functional state of mesenchymal stem cells or MSC-derived cells said method comprising subjecting said mesenchymal stem cells or MSC-derived cells, which mesenchymal stem cells have been isolated in accordance with the method hereinbefore defined, to said treatment regime and screening for an altered functional or phenotypic state.

By "altered" is meant that one or more of the functional or phenotypic parameters that are the subject of analysis are changed relative to untreated cells. This may be a desirable outcome where the treatment regime in issue is designed to improve cellular functioning. However, where the treatment regime is associated with a detrimental outcome, this may be indicative of toxicity and therefore the unsuitability for use of the treatment regime. It is now well known that the differences that are observed in terms of the responsiveness of an individual to a particular drug are often linked to the unique genetic makeup of that individual. Accordingly, the method of the present invention provides a valuable means of testing either an existing or a new treatment regime on cells that are generated utilizing nuclear material derived from the individual in issue. This provides a unique means for evaluating the likely effectiveness of a drug on an individual's cellular system prior to administering the drug in vivo. Where a patient is extremely unwell, the physiological stress that can be caused by a treatment regime that causes an unwanted outcome can be avoided or at least minimized.

Accordingly, this aspect of the present invention provides a means of optimizing a treatment that is designed to normalize cellular functioning. However the method can also be used to assess the toxicity of a treatment, in particular a treatment with a compound. Thus, failure to generate a characteristic associated with a hematopoietic or mesenchymal phenotype, for example, in the cells and tissues of the present invention in response to treatment with a compound can be used to assess the toxicity of such a compound.

Hence the method of the present invention can be used to screen and/or test drugs, other treatment regimes or culture conditions. In the context of assessing phenotypic changes, this aspect of the present invention can be utilized to monitor for changes to the gene expression profiles of the subject cells and tissues. Thus, the method according to this aspect of the present invention can be used to determine, for example, gene expression pattern changes in response to a treatment.

Preferably, the treatment to which the cells or tissues of the present invention are subjected is an exposure to a compound. Preferably, the compound is a drug or a physiological ion. Alternatively the compound can be a growth factor or differentiation factor. To this end, it is highly desirable to have available a method which is capable of predicting such side effects on cellular populations prior to administering the drug.

Also provided by the subject invention are kits and systems for practicing the subject methods, as described above (generically referred to below as "kits"). For example, kits may contain reagents and components for producing EPC in vitro from a suitable source (e.g., placenta) for either therapeutic or research purposes. In such embodiments, the kits may include such reagents as cytokines, cell culture media, enzymes (e.g., for cell dissociation, e.g., Accutase), antibodies and/or gene probes (e.g., antibodies or gene probes specific for CD31, CD45, CD34, CD105, CD144, CD146, VEGFR2, HLA-ABC, CD73 and a HLA-DR as well as any one or more of the marker genes listed in Table 1, or expression products thereof, etc.), culture plates or flasks, stocks of EPC, etc. Any reagent that finds use in producing and/or using the EPC according to the present invention, or in performing quality control analyses on such EPC, can be included.

In some embodiments, the kit is designed for endothelial cell production and includes one or more of the EPC described herein and one or more additional components used for the propagation of the EPC and/or for inducing endothelial cell production from the EPC. Such systems and kits may be for therapeutic and/or research purposes.

The subject systems and kits may also include one or more other reagents for preparing or using EPC according to the subject methods. The reagents may include one or more matrix or scaffold (or reagents for generating the matrix/scaffolds), hydrating agents (e.g., physiologically-compatible saline solutions, prepared cell culture media), cell culture substrates (e.g., culture dishes, plates, vials, etc.), cell culture media (whether in liquid or powdered form), antibiotic compounds, hormones, additives, etc. As such, the kits may include one or more containers such as vials or bottles, with each container containing a separate component for carrying out a processing or preparing step according to the present invention.

In certain embodiments, the kit may further include components designed to facilitate the delivery of a cell population, e.g., to an experimental animal or to a patient in the need thereof, e.g., a patient in need of EPC-based therapy. In these latter embodiments, the components of the kit may be provided in a form that is suitable for therapeutic use (e.g., provided in as sterile/medical grade components). Delivery components can include those designed for encapsulating or immobilizing the cell population (e.g., a scaffold or matrix) as well as for delivering the cells, either directly or in association with other components (e.g., a scaffold or matrix), including injecting the isolated cells into the site of defect, incubating and/or culturing the embryonic progenitor cells with a suitable scaffold or matrix and implanting, incubating with bio-resorbable scaffold, etc. Any convenient scaffolds or matrices, such as bio-resorbable, bio-compatible scaffolds as described in detail above, may be employed, where a number have been employed for, or are being tested for use in, therapeutic endothelial repair, replacement or tumor targeting.

In some embodiments, the kit includes components for use in determining that the delivered/transplanted cell population locates to at least one desired site in a subject, e.g., a patient. Such components may allow the determination of the localization and even quantification of cells delivered cells to a subject.

In certain embodiments, the EPC in the kit are genetically modified. For example, as discussed above, EPC may be engineered to express a heterologous gene, e.g., a gene that imparts a therapeutic outcome or a marker gene that can be used for later identification of cells derived from the EPC (e.g., a reporter gene as is well known in the art). Reporter genes include those that are directly or indirectly detectable, e.g., fluorescent proteins, luminescent proteins, enzymes, cell surface markers, and the like. In certain embodiments, different cell lines re-engineered to express exogenous reporter genes that are discriminable from each other, e.g., fluorescent proteins having different excitation and/or emission characteristics.

In certain embodiments, the kit can include any or all components necessary for its intended use. For example, kits according to the invention may include a number of other suitable articles or components such as tubes, sutures, scalpels, needles, syringes, antiseptics for preparation of surgical sites, etc.

Additional types of kits are also provided in aspects of the present invention.

For example, kits are provided for the identification and/or isolation of EPC according to the present invention. Such kits will include reagents designed for detecting the expression of cell markers including any of the gene expression markers described herein. Such detection reagents may be formulated to detect expression products of these genes at either at the protein or nucleic acid (e.g., mRNA) level. As such, reagents may include: antibodies or specific binding portions thereof (e.g., detectably labeled antibodies), other specific protein binding agents (e.g., ligands or soluble receptors), nucleic acid probes for use in hybridization analysis, e.g., northern blot analysis, microarray analysis, and the like; primer pairs for use in PCR assays, e.g., quantitative PCR assays, etc.

The subject kits typically further include instructions for using the components of the kit to practice the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging), etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the components noted above, the kits may also include one or more control samples and reagents, e.g., two or more control samples. Such control samples may take any form, e.g., additional cell lines having known marker profiles, negative and positive control samples for use in analyzing gene expression data, etc. Any convenient control sample may be employed in the subject kits.

The present invention is further described by reference to the following non-limiting examples.

EXAMPLES

Example 1

Placental Digestion and Sorting Strategy

Human term placentas were obtained from healthy pregnant mothers undergoing elective caesarean section upon informed consent as required by our approved ethics protocol. Upon collection, the decidual tissues membrane and cord were dissected and the cotyledons kept. The cotyledons were then washed in Hanks Buffered Salt Solution (HBSS) before being subjected to digestion in 1 mg/mL collagenase I, 1 mg/mL Dnase-1 and 75 μg/mL Dispase solution for 2 hours at 37° C. Upon digestion the single cell suspension was filtered through a 100 μm sieve and spun at 750×g for 5 minutes. The supernatant was poured off and subsequent cell pellet resuspended in a red cell lysis buffer and incubated at room temperature for 10 minutes. The suspension was then spun at 510×g for 5 minutes. The supernatant was then poured off and cell pellet washed in HBSS and re-spun at 510×g for 5 minutes. Cells were resuspended in ice cold MACS buffer (phosphate buffered solution, (PBS) containing 2 mM EDTA, 0.5% BSA) then incubated with CD45 antibodies labeled with magnetic beads (DYNABEADS) for 15 minutes at 4° C., before being placed into a DYNA-MAGNET holder to deplete CD45 labeled cells. The remaining cells were then spun at 510×g for 5 minutes before being resuspended in 1 mL of MACS buffer. CD34 MACS beads were then added and incubated at 4° C. for 15 minutes. The cells were washed with MACS buffer and spun at 510×g for 5 minutes before the cell pellet was resuspended in 3 mL of MACS buffer and passed through a magnetic column to collect the labeled CD34$^+$ cells. The cells were then stained with CD34, CD31 and CD45 antibodies and incubated for 20 minutes at 4° C. (FIG. 1).

Example 2

Flow Sorting Strategy

Figure 2:
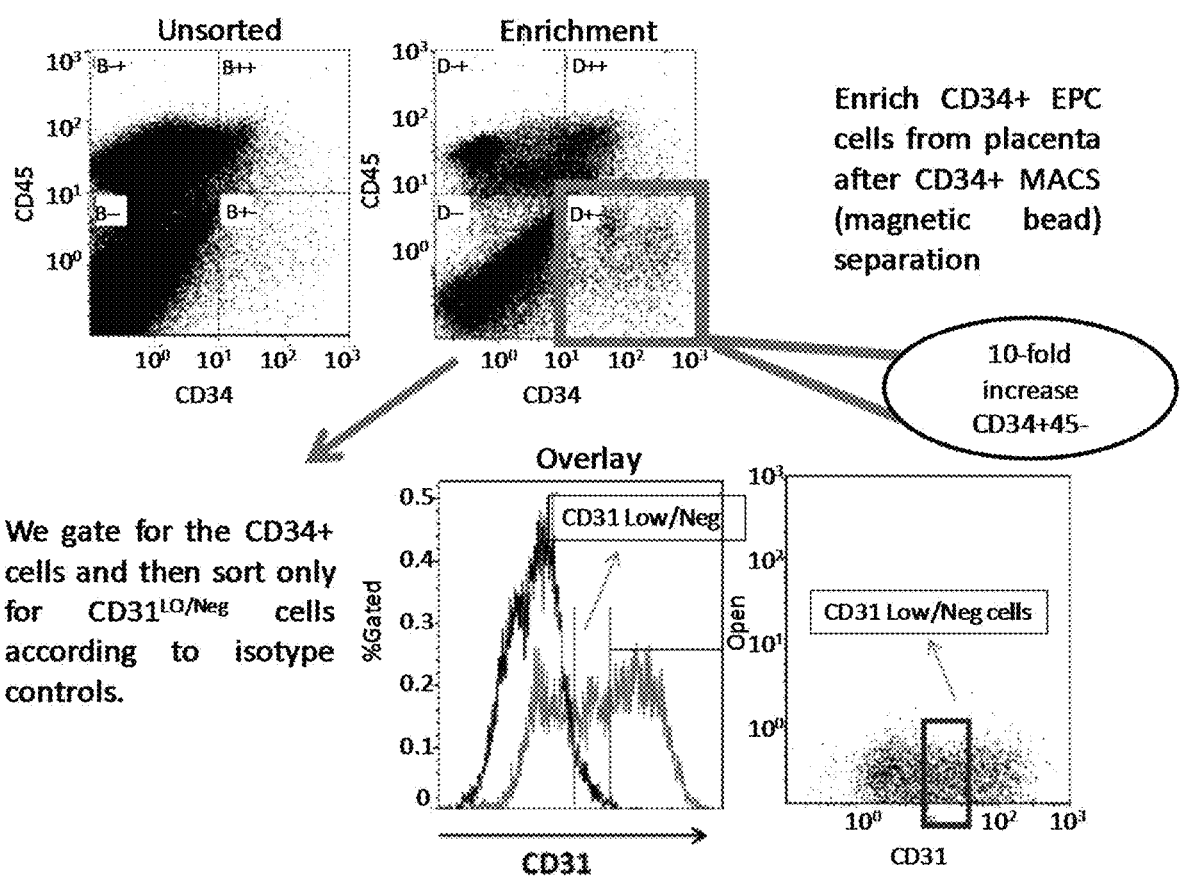
FIG. 2: Upon depletion of CD45$^+$ cells using DYNABEADS, cells are enriched for CD34 using MACS sorting. This allows a ten-fold enrichment. Using flow cytometry we can further dissect this population in three subpopulations according to CD31 expression levels. The highest endothelial stem cell activity resides in the CD31$^{lo/-}$ cells whereas CD31$^+$ cells provide only limited colony forming potential.

Through flow cytometry only CD34$^+$ cells were gated, to remove any contaminating CD45$^+$ cells. CD34$^+$ gated cells were then analyzed for their CD31 level of expression against the isotype matched control. (FIG. 2). The mean fluorescence intensity of CD31 staining for each CD45$^-$CD34$^+$ subpopulation, in a single illustrative experiment, is shown in Table 2.

TABLE 2

| Cell population among CD45$^-$CD45$^+$ | Mean fluorescence intensity of CD31 staining |
| --- | --- |
| CD31$^-$ | 4.5 |
| CD31$^{lo/-}$ | 42 |
| CD31$^{hi}$ | 868 |
| HUVEC control cells | 873 |

Notably, the mean fluorescence intensity that is observed for the HUVEC control cell line (characterized as being CD31$^{hi}$) is around 873. This is consistent with that observed for CD31$^{hi}$ CD45$^-$CD34$^+$ cells. Accordingly, cells that are CD31$^{hi}$ have around a 22-fold higher mean fluorescence intensity than CD31$^{lo/-}$ cells.

Cells that were CD34$^+$CD31$^{lo/-}$ were then sorted directly into 100% fetal bovine serum (FBS) and directly placed on ice. Cells were then spun and resuspended in EGM-2 (10% FBS) and plated onto pre-coated collagen cell culture plates.

Example 3

Colony Forming Capacity

Figure 3:
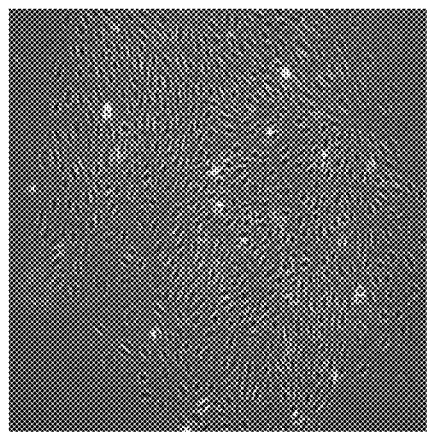
FIG. 3: Photomicrograph depicting highly proliferative potential endothelial colony forming cells (EPP-ECFC) 10 days after culture of placental EPC. These EPC have the described characteristics of ECFC. HPP colonies are counted on basis of having 50 or more cells at ten days after plating.

We are able to isolate significantly more ECFC with high proliferative potential (HPP-ECFC) using our claimed method in comparison to cord blood (FIG. 3). Colonies are counted following 10 days of in vitro culture.

Using the well-described ECFC assay, cells were maintained in EGM-2 (10% FBS) with medium changed every 2 days for a period of 14 days. At day 10 HPP-ECFC were counted and compared with HPP-ECFC colonies obtained from cord blood. Colonies with more than 50 cells in the colony were regarded as being HPP-ECFC.

Example 4

Fetal Stem Cells

Figure 4:
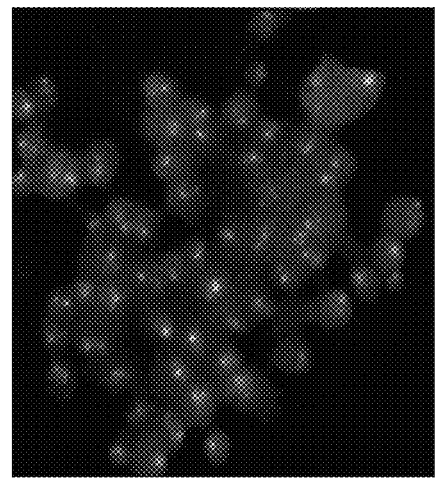
FIG. 4: Fluorescence In-situ Hybridization (FISH). Placental ECFC are fetal in origin. X=green, Y=red. Photograph depicting Fluorescence In-situ Hybridization of X and Y chromosomes on cyto-spun ECFC grown from the placenta of a male newborn. More than 95% of the cells displayed one X and one Y chromosome clearly indicating their fetal origin.

The grown colonies are 100% fetal as determined by X and Y chromosome in situ hybridization in male pregnancies (FIG. 4).

Cells were fixed using Carnoy's Fixative (75% methanol, 25% acetic acid) before a drop of cell suspension was placed onto a Superfrost Plus slide and left to dry. Slides were then placed into a 37° C. overnight to 'pre-age' the cells. Fluorescence in situ hybridization (FISH) analysis for X and Y chromosomes of these cells was then conducted as per the manufacturer's protocol (Abbott Molecular, Ill., USA). The Zeiss Axio microscope was used to analyse the slides.

Example 5

Characterization

Figure 5:
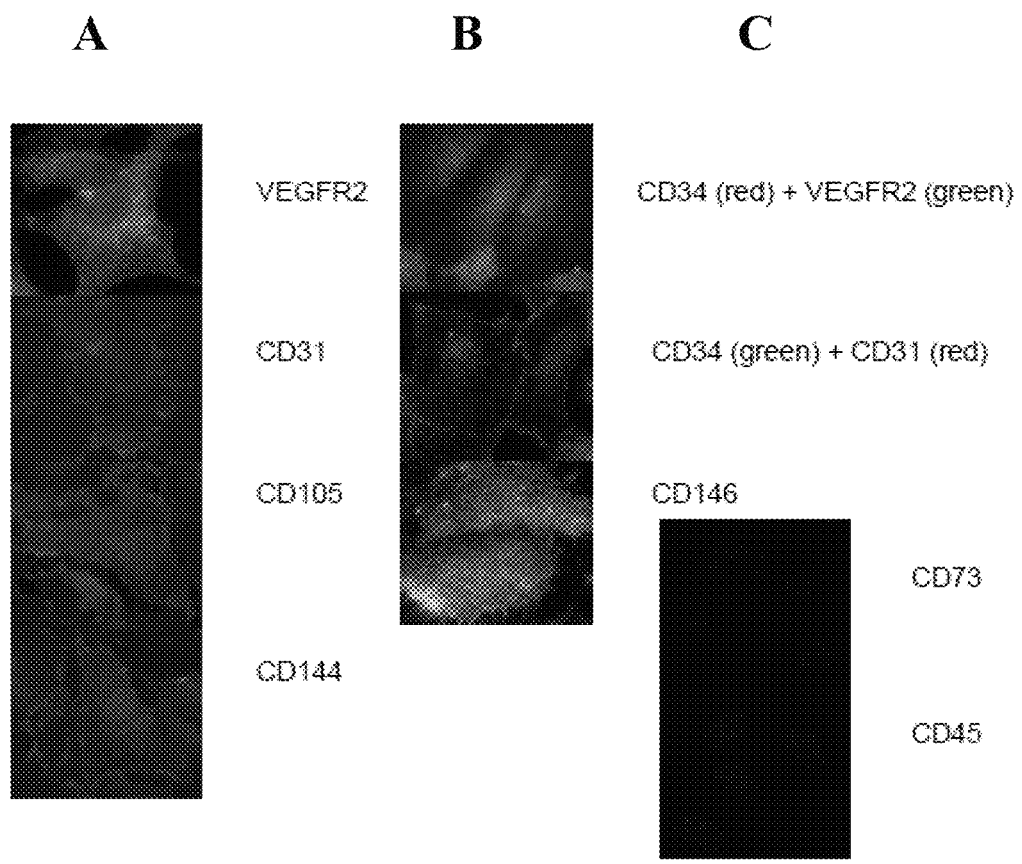
FIG. 5: Endothelial cells were obtained upon culture of placental EPC as indicated by our isolation method. Cells were then stained by immunofluorescence and compared to staining using an isotype control (not shown). Positive staining is demonstrated for endothelial markers including CD34, VEGFR2 (A and B), CD31, CD105, CD144 (A) and CD146 (B) and negative for hematopoietic marker CD45 and mesenchymal marker CD73 (C).

The resulting colonies in culture have all accepted characteristics of endothelial cells: they express CD34, CD144, CD105, CD31, VEGFR2, CD146 but do not express hematopoietic markers CD45 or mesenchymal stem cell marker CD73 as demonstrated by immunofluorescence staining (FIG. 5).

The colonies were grown as previously described using chamber slides. The cells were then fixed in ice-cold acetone for 10 minutes and washed three times using PBS. Normal goat serum, diluted at 1:250 in PBS/0.1% Tween/3% BSA, was used as a blocking agent and incubated on the cells for 20 minutes at room temperature. The following primary antibodies were used at a dilution of 1:250. Rabbit-anti-human CD34, mouse-anti-human CD144, mouse-anti-human CD105, mouse-anti-human CD31, mouse-anti-human VEGF-R2, mouse-anti-human CD146, mouse-anti-human CD45 and mouse-anti-human CD73. The following secondary antibodies were used at a dilution of 1:1000. Alexa488-goat-anti-rabbit, Alexa488-goat-anti-mouse, Alexa568-goat-anti-rabbit and Alexa568-goat-anti-mouse. Prolong Gold anti-fade reagent with DAPI was used as the mounting medium and all slides were analyzed using the Zeiss Axio microscope.

Example 6

Functional Characterization

The resulting colonies also conform to endothelial functional characteristics as observed by the uptake of acetylated low-density lipoprotein (Ac-LDL) (FIG. 6A) and forming tubes in vitro when plated onto MATRIGEL (FIG. 6B).

(A) To determine the uptake of acetylated-LDL, cells were cultured as described previously, before being serum starved for 12 hours. The cells were then incubated with Ac-LDL pre-labeled with DiI (DiI-Ac-LDL) (10 µg/mL) in serum free culture medium for 4 hours at 37° C. The cells were then washed twice with PBS. Prolong Gold anti-fade reagent with DAPI was used as the mounting medium and all slides were analyzed using the Zeiss Axio microscope.

(B) A 96-well cell culture plate was pre-coated with MATRIGEL on ice before being placed into a 37° C. incubator for 30 minutes. $2 \times 10^4$ cells were then plated per well and cultured for a period of 18 hours. Images were obtained using the Olympus-CKX41 tissue culture light microscope.

Example 7

Engraftment

The cultured cells can engraft in vivo (MATRIGEL plug assay) when injected into mice and can form de novo blood vessels.

Figure 7:
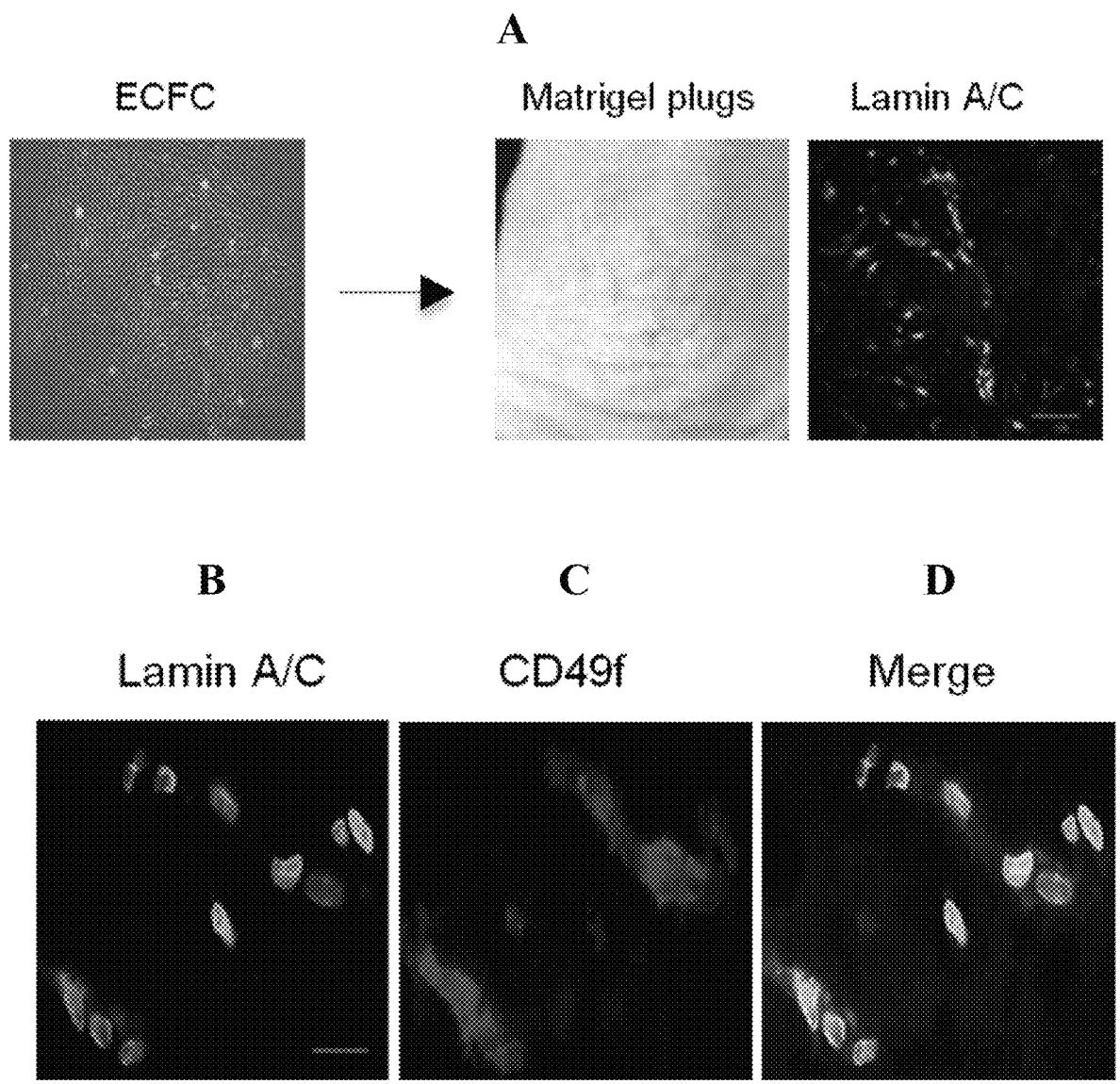
FIG. 7: (A) 0.5 million endothelial cells obtained upon culture of placental EPC as indicated by our isolation method were mixed with MATRIGEL and injected subcutaneously in nude mice. MATRIGEL plugs were recovered 7 days later and assessed by immunofluorescence. Human cells were retrieved using specific anti-human Lamin A/C antibody staining their nuclei (green). They formed tube like structures within the MATRIGEL plug. (B) ECFC were injected into MATRIGEL plugs to demonstrate engraftment through Lamin A/C staining (scale bar represents 100 μm). (C) Lamin A/C staining and vessel formation (CD49f). (D) Merge of Lamin A/C and CD49f staining. Results are presented as mean+/−SEM; n=3.

Specifically, the characteristic high proliferative ECFC colonies were observed, by labelling with α6-integrin (CD49f), as well as the human specific nuclear marker Lamin A/C (see, FIGS. 7A and B).

Materials and Methods

MATRIGEL Plug Assay and Engraftment of Human ECFC

A suspension of $1 \times 10^6$ cells with MATRIGEL (BD Biosciences) was prepared and plugs generated by subcutaneous injection into each flank of nu/nu mice. The MATRIGEL plugs were maintained for 7 days before being harvested. The plugs were fixed in 4% paraformaldehyde for 2 hours before being washed three times with PBS. The plugs were then embedded into OCT compound and frozen before sectioning. Once sectioned, the slides were stained with the primary antibody rabbit-anti-human Lamin A/C at a dilution of 1:250. A secondary antibody, Alexa-488-goat-anti-rabbit, was used at a dilution of 1:1000. Prolong Gold anti-fade reagent with DAPI was used as the mounting medium and all slides were analyzed using the Zeiss Axio microscope.

Example 8

Figure 8:
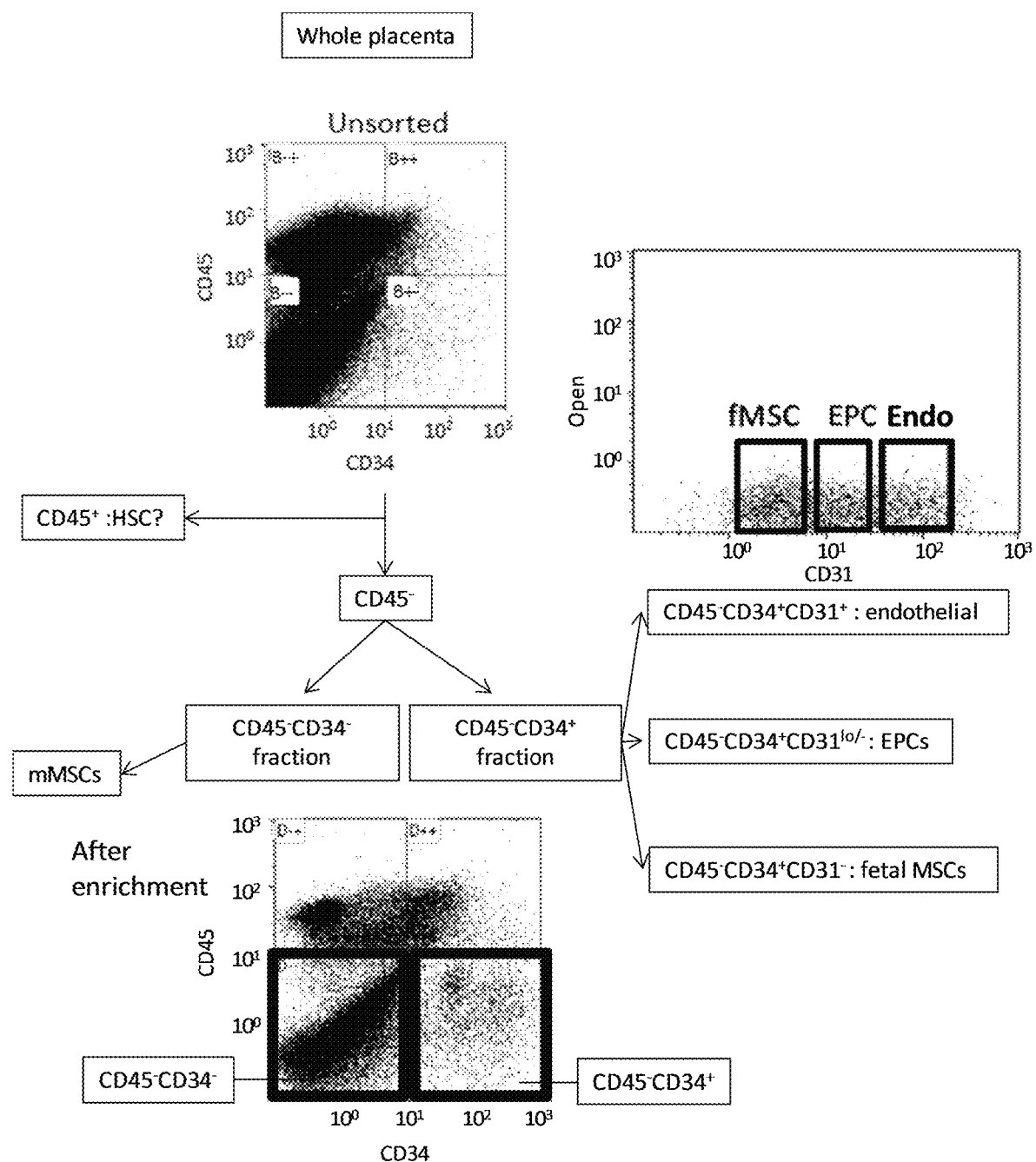
FIG. 8: Overall sorting strategy for MSC isolation. Term placenta is digested in cell suspensions as described for EPC. $CD45^+$ cells are first depleted using a magnetic sorting strategy. This is further followed by the enrichment of $CD34^+$ cells using again a magnetic sorting strategy. This enrichment gives rise to two populations a $CD34^-CD45^-$ (in blue gate on flow cytometry plot) and a $CD34^+CD45^-$ (in red gate). The $CD34^-CD45^-$ fraction results in maternal MSC once in culture. The $CD34^+CD45^-$ population is then further fractioned according to CD31 levels. $CD31^{-/lo}$ fraction gave rise to EPC as described. $CD31^-$ cells were considered and gave rise to MSC that were purely of fetal origin.
Figure 11:
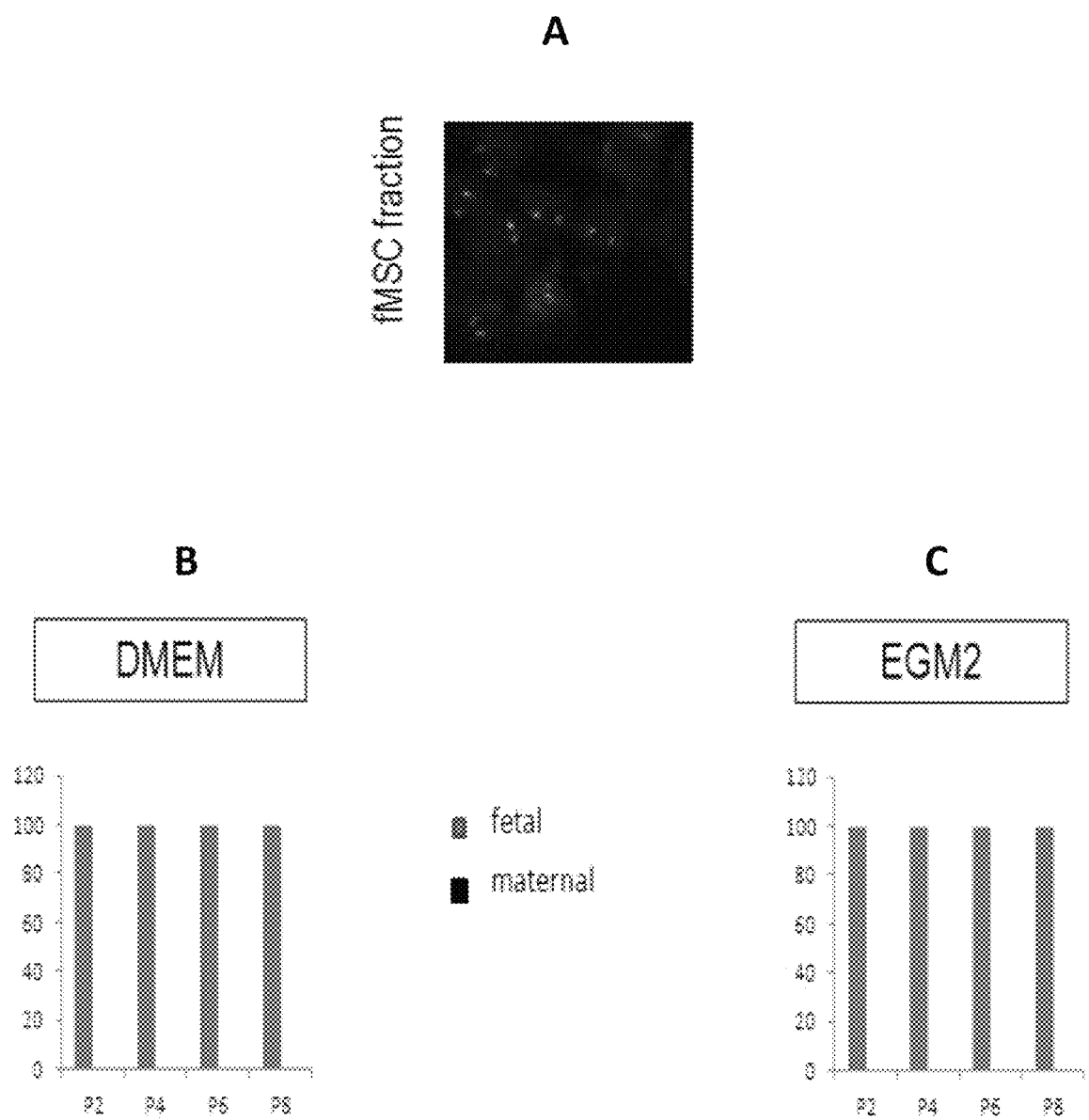
FIG. 11: fMSC fraction is purely fetal origin. A term placenta obtained from a woman carrying a boy was analyzed to distinguish maternal versus fetal origin of the different cells. $CD34^-CD45^-$ cells as well as MSC from whole placenta produced only MSC of maternal origin. (A): X and Y chromosome fluorescence in situ hybridization (FISH) was performed on carnoys fixed cells. X chromosome is depicted in red, Y chromosome in green. The fMSC fraction tested at passage 2 revealed only cells of fetal origin (100%). We next assessed if this composition would change over time. In DMEM or EGM2 culture cells remained purely fetal up to passage 8 (B, C).
Figure 12:
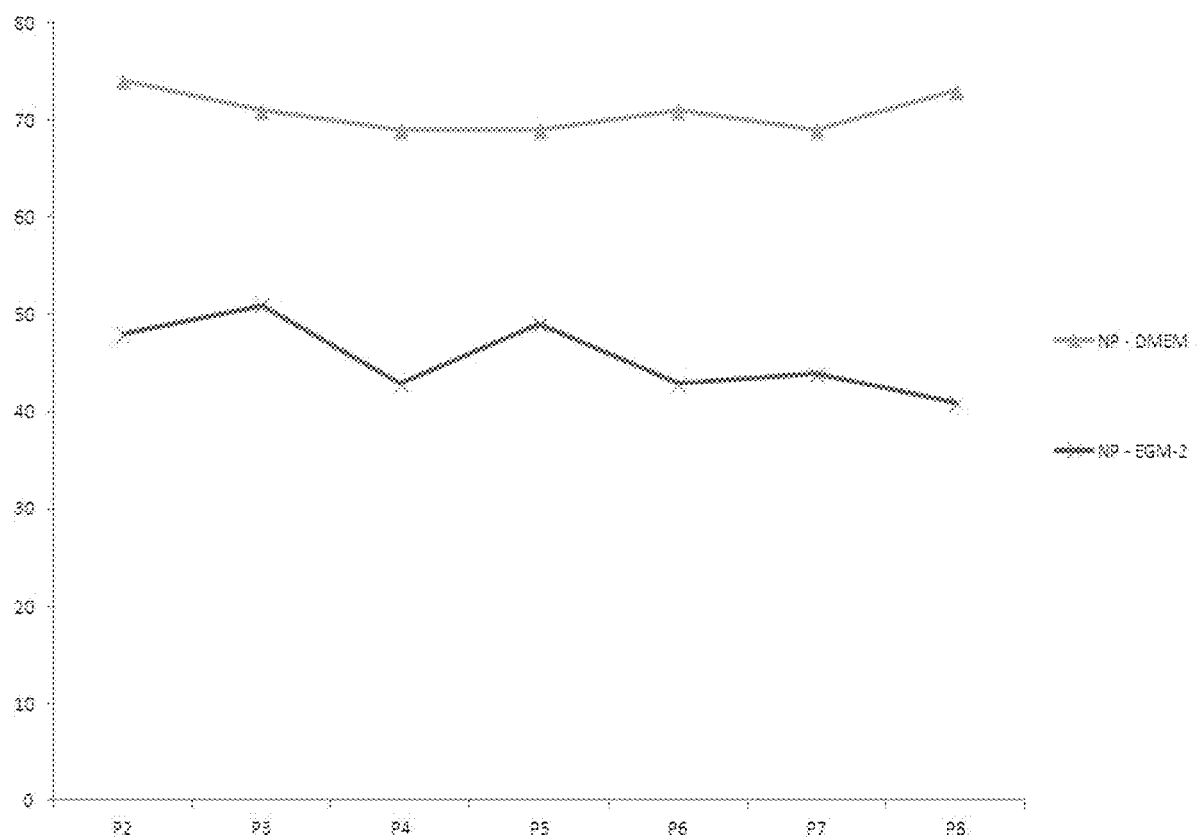
FIG. 12: fMSC derived from placental fractions can self-renew. Proliferation and population doubling over 8 passages was measured. It could be shown that fMSC population doubling was stable over time. It was faster in EGM2 medium as compared to DMEM medium.

Two of the different fractions that were tested for the presence of EPC grew significant numbers of fibroblast shaped cells even in EGM2 endothelial specific culture medium. These fibroblastic colonies rapidly overgrew any endothelial colony that was emerging. The two fractions where these fibroblastic cells could be found were the $CD34^-CD45^-$ fraction and the $CD45^-CD34^+CD31^-$ fraction (see, FIG. 8). These cells could be grown rapidly in monolayers on plastic without collagen in both DMEM or EGM2 media. They expressed characteristic cell surface molecules of mesenchymal stem cells (MSC) obtained from fetal or adult sources (FIG. 9). In addition, the cells exhibited mesenchymal differentiation potential in osteoblasts but mostly in adipocytes (FIG. 10). An important finding was the characterization of the origin of these cells. These cells were isolated from the placenta of mothers carrying boys exclusively and it could therefore be analyzed using X and Y chromosome FISH whether the cells were fetal (male) or maternal (female) in origin. The $CD34^-CD45^-$ fraction was composed of maternal MSC. However the $CD45^-CD34^+CD31^-$ fraction was fetal (FIG. 11). Previous studies have indicated that small maternal MSC contamination can completely overgrow fetal MSC upon passaging. Accordingly the fetal origin of cells was tested and confirmed over multiple passages (FIG. 11). Of note, MSC according to the accepted criteria are generally said to be $CD34^-$. However, the present data demonstrates that the presence of CD34 distinguishes fetal from maternal MSC. Finally, it was also demonstrated that the population doubling time of the fetal MSC does not change upon passaging, clearly indicating the self-renewal capacity of this population (FIG. 12). Overall, these results demonstrate the coexistence of two populations of MSC in full term placentas that can be isolated using the method of the present invention.

Example 9

Comparison Between Placenta-Derived and Umbilical Cord Blood-Derived ECFC

Figure 13A:
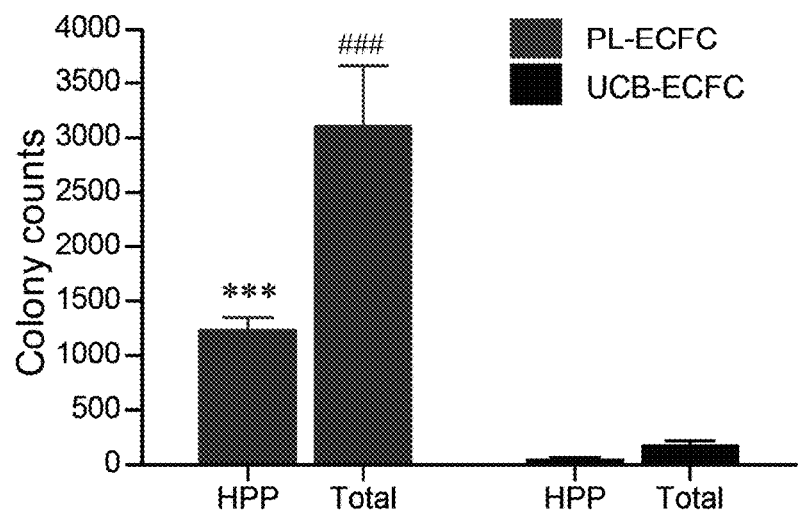
FIGS. 13A-G: Comparative in vitro analysis of PL-ECFC versus UCB-ECFC. Using the ECFC culture assay, colony formation was assessed for both placenta and umbilical cord blood (UCB). 50 g of placental villous tissue and 20 mL of UCB for each experiment (n=6). More HPP colonies (colonies with more than 50 cells) from PL-ECFC than from UCB-ECFC.
Figure 13B:
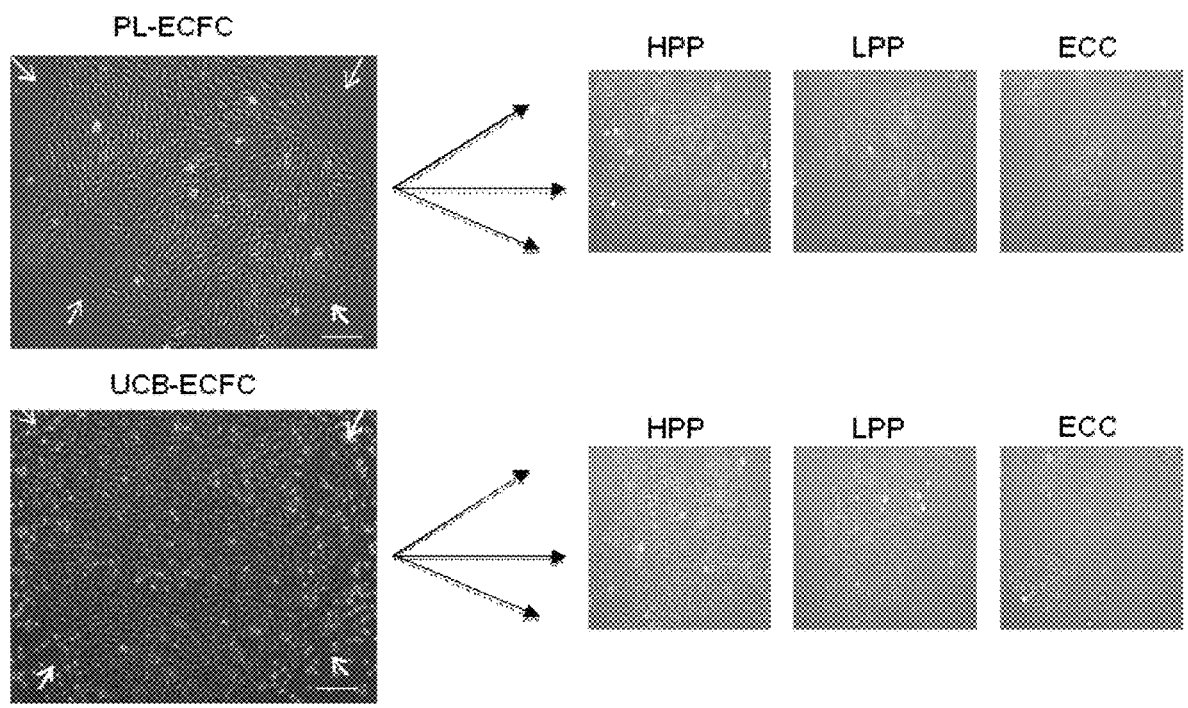

As described above, a limitation of UCB-ECFC has been the number of colonies that can be obtained and thus expanded for future clinical application. Through the use of an in vitro culture assay, it was found that 123±15 HPP colonies per 100,000 $CD34^+CD31^{lo/-}$ cells could be obtained from 50 g of placental villous tissue. This is significantly more than that achieved by plating total mononuclear cells from 20 mL of UCB, which obtained only 15±4 HPP colonies. Thus, it is estimated that per donor, 1,230 HPP colonies could be could be achieved per whole placenta (average weight, 500-600 g), wherein only 45 HPP colonies would likely be achieved per whole cord blood (average total volume=~60 mL; FIG. 13A).

Figure 13C:
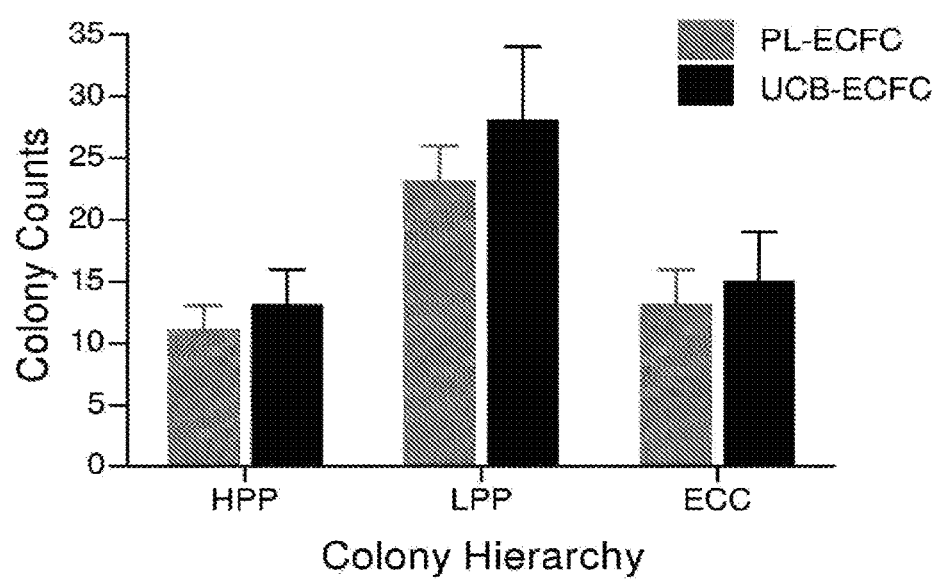

PL-ECFC had the same in vitro hierarchy as described in UCB-ECFC. Indeed, HPP colonies gave rise to HPP colonies and a number of smaller colonies. We replated 15 HPP ECFC colonies from both placenta and UCB at passage 2, which had on average 70-90 cells per HPP colony, and counted 11±2 and 13±3 new HPP colonies for placenta and UCB, respectively. This demonstrates the similar self-renewal capacity of both ECFC populations (FIG. 13C). Similarly, no significant differences were noticed in the number of low proliferative and endothelial cell colonies upon passaging HPP colonies from either placenta or UCB. Notably, the passaging of small colonies did not result in new colonies for either ECFC source.

Figure 13D:
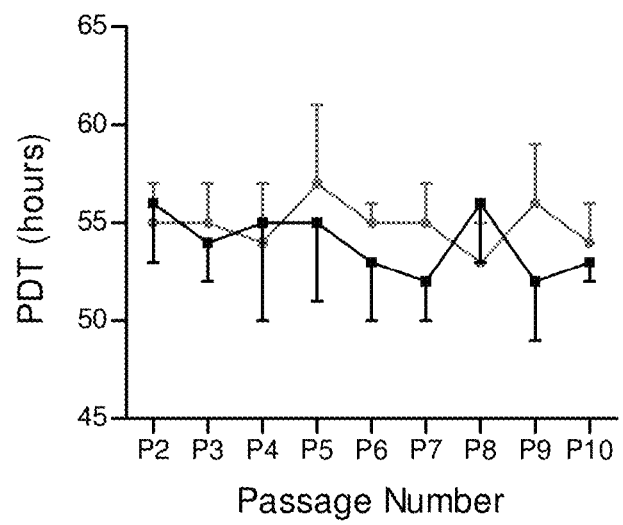
Figure 13E:
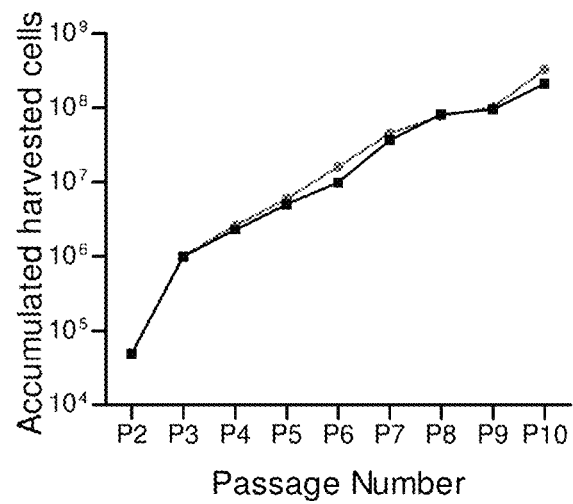
Figure 13F:
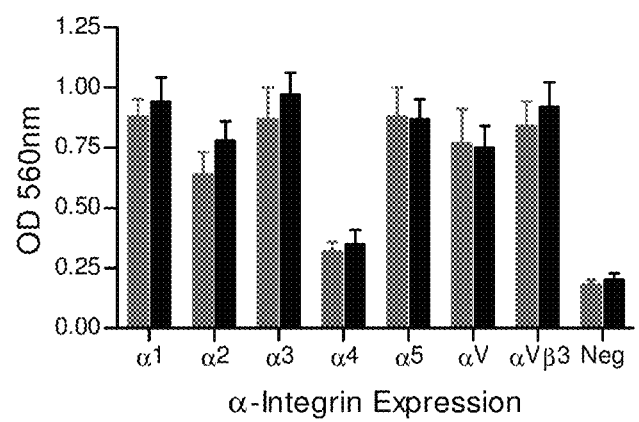
Figure 13G:
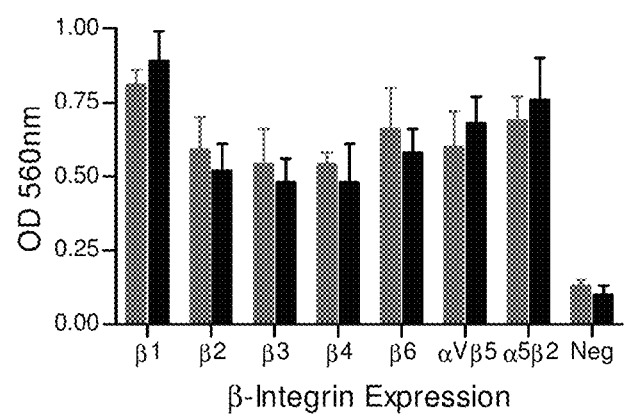

Cell harvest and population doubling time over subsequence passages (passages 2-10) was also commensurate between UCB-ECFC and PL-ECFC (about 55 hours doubling time) (FIG. 13D). Although PL-ECFC are postulated to be blood vessel-resident progenitor cells, in contract to UCB-ECFC, which are circulating progenitors, we observed little or no difference in the cell surface integrin profile of both cell types (FIG. 13E). Furthermore, we observed no immunosuppressive capacity in either PL-ECFC or UCB-ECFC as opposed to placental mesenchymal stem cells (FIG. 13F).

Figure 14:
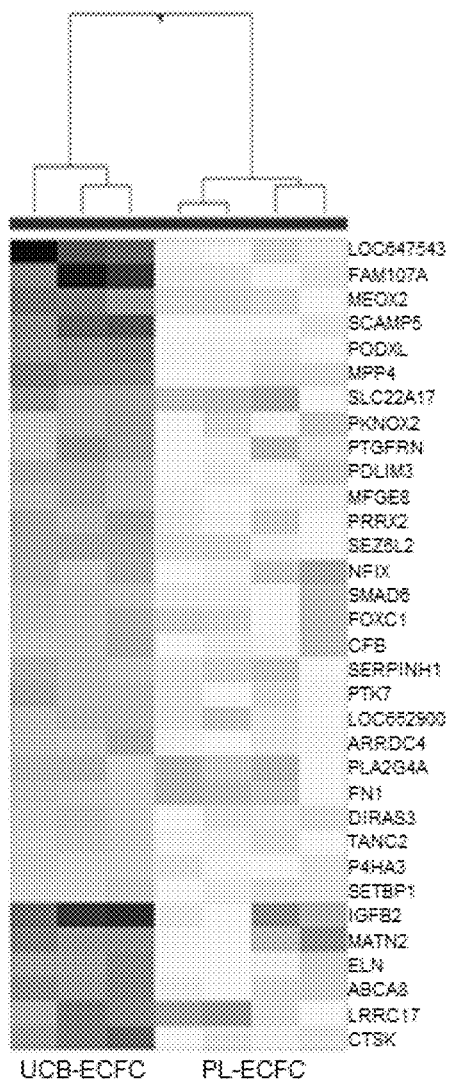
FIG. 14: Microarray hierarchical cluster map of 33 genes differentially expressed between PL-ECFC and UCB-ECFC. RNA was isolated from passage 2 PL-ECFC (n=4) versus UCB-ECFC (n=4) and analyzed for differential gene expression. Using a cutoff p value of 0.05 following normalization, only 33 differentially expressed genes were observed.

To compare molecular phenotypes, Illumina microarray expression profiling was performed on RNA isolated from donor-matched PL-ECFC and UCB-ECFC (n=4 biological replicates). Hierarchical cluster analysis could classify samples according to their origin. Using a cut-off p value of 0.05, only 33 genes were differentially expressed out of more than 40,000 (see, FIG. 14 and Table 1).

The minimal differences observed in genomic profiling further demonstrated the comparative nature of these two ECFC populations. Among these 33 genes, only 23 differed more than two-fold. Some are important in vascular biology, such as MFGE8 (released by apoptotic endothelial cells), SMAD6 (also termed FoxC2; important for vascular development). IGFBP2, a factor known to promote IGF-I signalling in endothelial cells and enhancing their recruitment during angiogenesis, was strongly unregulated in UCB-ECFC in comparison with PL-ECFC.

Other genes of interest included components of the extracellular matrix (SERPINH1, fibronectin, and elastin). Gene ontology pathway analysis of 191 genes differentially expressed at p<0.2 demonstrated differences associated with cell adhesion and migration.

Materials and Methods

In Vitro Culture Assay

All tissue culture plates/flasks (Nunc, Oskilde, Denmark) were initially pre-coated with a rat tail collagen type 1 solution (Sigma Aldrich, St. Louis, Mo., USA) and left to dry in a tissue culture hood for 6 hours before being washed three times with sterile PBS. The cells were then cultures with EGM-2 (Lonza, Mount Waverley, VIC, Australia) supplemented with 10% fetal bovine serum, and the medium was changed every 2 days over a 14 day period. On day 14 of culture, colony numbers and cell numbers within a colony were counted. A colony with more than 50 cells of cobblestone appearance was regarded as an HPP colony.

Microarray Analysis of PL-ECFC and UCB-ECFC Populations

Total RNA was extracted from placental and UCB-ECFC (n=4; passage 3) using the RNASY Mini Kit (Qiagen, Valencia, Calif.). RNA yield was determined using Nanodrop 1000, and quantity and quality validated using the Agilent 2100 Bioanalyzer (Agilent Technologies, Mulgrave, Victoria, Australia). Total RNA (500 ng) was converted to biotinylated cRNA using the TotalPrep RNA Amplification Kit (Illumina Inc., San Diego, Calif.) and hybridized to HumanHT-12 v4 BeadChip (Illumina). The hybridized BeadChip was washed and scanned with the Illumina BeadStation system. Microarray analysis was conducted using GeneSpring (Agilent Technologies) software.

Example 10

Hind Limb Ischemia Injury

The functional capacity of PL-ECFC was assessed in a murine hind limb ischemia (HLI) model. Following arterial ligation, PL-ECFC, UCB-ECFC, or saline was injected, and perfusion was thereafter measured by Doppler analysis.

At days 0 and 2, before delivery of cells, there was no difference in perfusion between groups. However, by day 7, 1.85- and 2.1-fold increases in perfusion were observed in PL-ECFC- and UCB-ECFC-injected animals, respectively, in comparison with matched saline-injected mice (PL-ECFC versus saline, p<0.02; UCB-ECFC versus saline, p<0.007). This improvement in perfusion was also observed at day 14 (1.75-fold increase in PL-ECFC versus saline, p<0.02; 1.9-fold increase in UCB-ECFC versus saline, p<0.009) and day 21 (1.5-fold increase in PL-ECFC versus saline, p<0.05; 1.4-fold increase in UCB-ECFC versus saline, p<0.03). Total loss of perfusion at day 14 was observed in four mice in the saline group versus zero mice in the two other groups (see, FIG. 15).

To track the injected cells, human-specific Lamin A/C staining was performed. Lamin A/C is a nuclear membrane protein observed ubiquitously in all nucleated human cells. As expected, no human Lamin A/C-positive cell was observed in saline injected mice. However, human cells could be observed in both the PL-ECFC-injected mice and the UCB-ECFC-injected animals at similar levels. Co-staining with anti-mouse CD31 confirmed that human-specific Lamin A/C-positive cells engrafted and were incorporated into murine vessels, forming chimeras, although this was not the dominant phenotype (see, FIG. 5).

Hind Limb Ischemia in Atherosclerotic Model

Patients with critical leg ischemia generally have atherosclerotic changes through their vasculature. Although a point of stenosis in the upper femoral artery is a major feature of clinical critical leg ischemia, femoral artery ligation in otherwise healthy animals does not necessarily reflect the clinical scenario. It is thus difficult to appreciate if ECFC have the same efficacy in an ischemic leg with severely atherosclerotic vessels, and whether the host vasculature are able to respond to paracrine signals from ECFC to generate neo-vessels. The ApoE$^{-/-}$ mouse model is known to develop atherosclerotic changes spontaneously in many of its arteries by 9-12 months of age (see, Moghadasian et al, 2001). In this example, hind limb ischemia will be used on this background.

Materials and Methods

Hind Limb Ischemia Reperfusion Assay

A modified protocol based on a previously described murine model of hind limb ischemia was used (Niiyama H., Huang N. F., Rollins, M. D., et al, Murine model of hindlimb ischemia, *J. Vis. Exp.,* 2009; 23:1035).

Specifically, nude (nu/nu) mice aged between 8 and 10 weeks and weighing 17=22 g were anesthetized with 100 mg/kg ketamine and 10 mg/kg xylazine. The proximal and distal portions of the right femoral artery were ligated, followed by isolation and resection of the artery. Two days after the ligation, $5 \times 10^5$ PL-ECFC or UCB-ECFC or saline only were injected intramuscularly. Hind limb blood perfusion was measured with a laser Doppler perfusion imager (LDPI) system (Moor Instruments Ltd., Devon, U.K.) conducted at room temperature (25° C.) immediately before and after the surgery, 2 days post surgery, and weekly thereafter. Results were expressed as the ratio of perfusion in the right (ischemic) limb versus the left (non-ischemic) limb to eliminate confounding effects from the environment and inter-individual variations.

The impact of ECFC administration on therapeutic vascularization was investigated in the hind limb ischemia (HLI) model. Two days after femoral artery resection, stable ischemia was verified by LDPI and identically injected saline in the control group (n=16), or with PL-ECFC (n=8) or UCB-ECFC (n=10) in the treatment groups. Bolus injections of 20 μl were delivered intramuscularly in four divided doses in the vicinity of the proximal ligation site.

Given the intrinsic exhaustion of angiogenesis capacity in ApoE$^{-/-}$ mice, we expect that ECFC therapy will have a larger impact on this background.

Hind Limb Ischemia Apo$^{-/-}$ Mouse

Three groups of Apo-/- mice and C57Bl/6 controls are used. Animals will be subjected femoral artery ligation at 9 months of age. They will be injected with either ECFC alone, ECFC and cyclosporine (limited to the first 3 weeks), or vehicle. Evaluation will be performed over 42 days for leg perfusion using bioluminescence imaging (BLI), laser Doppler imaging engraftment and finally host and donor derived vessel formation.

Example 11

Vascular Prosthesis

Prostheses are playing an increasing role in vascular interventions for major arteries. Vascular surgery often relies on prostheses developed and applied in a range of vascular interventions such as coronary artery dilatation, carotid artery endarterectomy, renal, femoral artery bypass or aortic aneurysm surgery. A major complication is thrombosis and restenosis while the synthetic vascular prosthesis is being re-colonized by host endothelial cells. The inventors clearly envisage that the present technology will be effective in the pre-endothelialization in vitro of vascular prostheses and stents.

The inventors envisage that 6 animals per group should provide sufficient power to observe the reported 60% reduction in neo-intimal thickness and the 65% increase in endothelialization.

Materials and Methods

Preparation of Vascular Prostheses

Dacron and polytetrafluoroethylene (PTFE) grafts (ATRIUM®), which are currently the most commonly used material for vascular prostheses, have been obtained and coated with collagen type I so that they are suitable for ECFC culture. Coated material in 1 cm$^2$ surfaces will be first seeded with GFP-tagged ECFC at passage 2 in EGM2 media as per standard culture condition. Seeding density will vary between 10$^4$, 10$^5$ or 10$^6$ cells/cm$^2$. Using a live imaging microscope (IncuCyte) the population doubling time and confluency will be examined and compared on each type of material at each seeding density to choose the best conditions. These experiments will be conducted with ECFC from 6 different donors.

In two groups of 6 sheep, a femorotibial bypass surgery will be performed using either an ECFC coated vascular graft of a non-coated graft kept in EGM2 for the same amount of time. Animals will receive 100 Ui/kg of heparin on a daily basis, as well as 10 mg/kg of cyclosporin. After 4 weeks, animals will be sacrificed and the grafts and the immediate adjacent arteries collected for histological analysis. Patency (% of lumen open), intimal diameter in transversal section, percentage of coverage by CD31$^+$ cells and human GFP$^+$ cells in en face whole mounts will be measured and compared between both groups.

Alternatively, in two groups of 6 sheep, a femoral stent coated with human anti-CD34 antibodies will be deployed percutaneously. One group will immediately receive around 10 million CD34 enriched ECFC versus vehicle alone, through the same catheterization route and by interrupting the circulation for 2 minutes proximal to the stent. Animals will be evaluated for endothelialization and restenosis as described above.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Assmus, B., et al., Transplantation of Progenitor Cells and Regeneration Enhancement in Acute Myocardial Infarction (TOPCARE-AMI), *Circulation* 106: 3009-3017 (2002)

Bartunek, J., et al., Intracoronary injection of CD133-positive enriched bone marrow progenitor cells promotes cardiac recovery after recent myocardial infarction: feasibility and safety. *Circulation* 112: 1178-183 (2005)

Case, J., et al., Human CD34+AC133+VEGFR-2+ cells are not endothelial progenitor cells but distinct, primitive hematopoietic progenitors, *Exp Hematol* 35: 1109-1118 (2007)

Fisk, N. M. & Atun, R., Public-private partnership in cord blood banking, BMJ 336, 642-644 (2008)

Flamme, I., Frolich, T. & Risau, W., Molecular mechanisms of vasculogenesis and embryonic angiogenesis, *J Cell Physiol* 173: 206-210 (1997)

Ingram, D. A., et al., Identification of a novel hierarchy of endothelial progenitor cells using human peripheral and umbilical cord blood, *Blood* 104: 2752-2760 (2004)

Kawamoto, A., et al., Intramuscular transplantation of G-CSF-mobilized CD34(+) cells in patients with critical limb ischemia: a phase I/IIa, multicenter, single-blinded, doseescalation clinical trial, *Stem Cells* 27: 2857-2864 (2009)

Kumar, A. H. & Caplice, N. M., Clinical potential of adult vascular progenitor cells, *Arterioscler Thromb Vasc Biol* 30: 1080-1087 (2010)

Lin, Y., Weisdorf, D. J., Solovey, A. & Hebbel, R. P., Origins of circulating endothelial cells and endothelial outgrowth from blood, *J Clin Invest* 105: 71-77 (2000)

Minamino, T. & Komuro, I., Vascular aging: insights from studies on cellular senescence, stem cell aging, and progeroid syndromes, *Nat Clin Pract Cardiovasc Med* 5; 637-648 (2008)

Op den Buijs, J., et al., Mathematical modeling of vascular endothelial layer maintenance: the role of endothelial cell division, progenitor cell homing, and telomere shortening. *Am J Physiol Heart Circ Physiol* 287: H2651-2658 (2004)

Patan, S., Vasculogenesis and angiogenesis, *Cancer Treat Res* 117: 3-32 (2004)

Rafii, S., et al., Characterization of hematopoietic cells arising on the textured surface of left ventricular assist devices, *Ann Thorac Surg* 60: 1627-1632 (1995)

Rohde, E., et al., Blood monocytes mimic endothelial progenitor cells. *Stem Cells* 24: 357-367 (2006)

Schwartz, S. M. & Benditt, E. P., Clustering of replicating cells in aortic endothelium, *Proc Natl Acad Sci USA* 73: 651-653 (1976)

Stamm, C., et al., Autologous bone-marrow stem-cell transplantation for myocardial regeneration. *Lancet* 361: 45-46 (2003)

Tateishi-Yuyama, E., et al., Therapeutic angiogenesis for patients with limb ischaemia by autologous transplantation of bone-marrow cells: a pilot study and a randomised controlled trial. *Lancet* 360: 427-435 (2002)

Tendera, M., et al., Intracoronary infusion of bone marrow-derived selected CD34+CXCR4+ cells and non-selected mononuclear cells in patients with acute STEMI and reduced left ventricular ejection fraction: results of randomized, multicentre Myocardial Regeneration by Intracoronary Infusion of Selected Population of Stem Cells in Acute Myocardial Infarction (REGENT) Trial, *Eur Heart J* 30: 1313-1321 (2009)

Woywodt, A., et al., Isolation and enumeration of circulating endothelial cells by immunomagnetic isolation: proposal of a definition and a consensus protocol, *J Thromb Haemost* 4: 671-677 (2006)

Xu, Q, The impact of progenitor cells in atherosclerosis. *Nat Clin Pract Cardiovasc Med* 3: 94-101 (2006)

Yoder, M. C., Defining human endothelial progenitor cells. *J Thromb Haemost* 7 Suppl 1: 49-52 (2009)

The invention claimed is:

1. A method of isolating mammalian fetal mesenchymal stem cells (MSC) said method comprising the steps of:
   (i) isolating a mammalian cellular population, wherein the mammalian cellular population is a placenta-derived cellular population;
   (ii) enriching for a subpopulation of the cells of step (i), which subpopulation expresses a $CD45^-$ phenotypic profile;
   (iii) enriching for a subpopulation of the $CD45^-$ cells derived from step (ii), which subpopulation express a $CD34^+$ phenotypic profile; and
   (iv) isolating the subpopulation of said $CD34^+$ cells which express a $CD31^-$ phenotypic profile;
   to thereby isolate the fetal MSC.

2. A method of facilitating the generation of a mammalian MSC-derived cell, said method comprising contacting the mesenchymal stem cells isolated in accordance with the method of claim 1 with a stimulus to direct the differentiation of said mesenchymal stem cells to a mesenchymal phenotype.

3. A method of repairing or regenerating a tissue in a mammal, said method comprising administering to said mammal an effective number of mesenchymal stem cells, which mesenchymal stem cells have been isolated according to the method of claim 1.

4. A method for producing a biocompatible implant, comprising seeding a cell support substrate, or coating a surface of a medical device, with the isolated mammalian mesenchymal stem cells isolated by the method of claim 1.

5. The method biocompatible implant of claim 4, wherein the cell support substrate is a polymer matrix.

\* \* \* \* \*